(12) United States Patent
Tang et al.

(10) Patent No.: US 9,234,181 B2
(45) Date of Patent: Jan. 12, 2016

(54) RNA EXPRESSION CASSETTE AND CELLS FOR MAKING ALPHAVIRUS PARTICLES

(75) Inventors: Zequn Tang, Corning, NY (US); Jan zur Megede, San Francicso, CA (US)

(73) Assignee: Novartis AG (CH)

( * ) Notice: Subject to any disclaimer, the term of this patent is extended or adjusted under 35 U.S.C. 154(b) by 584 days.

(21) Appl. No.: 12/744,878

(22) PCT Filed: Nov. 26, 2008

(86) PCT No.: PCT/US2008/084848
§ 371 (c)(1),
(2), (4) Date: Mar. 25, 2011

(87) PCT Pub. No.: WO2009/079185
PCT Pub. Date: Jun. 25, 2009

(65) Prior Publication Data
US 2011/0207223 A1   Aug. 25, 2011

Related U.S. Application Data

(60) Provisional application No. 60/990,088, filed on Nov. 26, 2007.

(51) Int. Cl.
*A01N 63/00*    (2006.01)
*C12N 7/00*    (2006.01)

(52) U.S. Cl.
CPC ........ *C12N 7/00* (2013.01); *C12N 2770/36143* (2013.01); *C12N 2770/36152* (2013.01)

(58) Field of Classification Search
USPC ....................................................... 424/93.2
See application file for complete search history.

(56) References Cited

U.S. PATENT DOCUMENTS

| | | | | |
|---|---|---|---|---|
| 6,524,792 | B1 * | 2/2003 | Renner et al. | 435/5 |
| 2003/0232324 | A1 * | 12/2003 | Polo et al. | 435/5 |
| 2006/0160150 | A1 * | 7/2006 | Seilhamer et al. | 435/7.2 |
| 2006/0292175 | A1 * | 12/2006 | Polo et al. | 424/204.1 |

FOREIGN PATENT DOCUMENTS

WO   WO 2006076032    *   7/2006

OTHER PUBLICATIONS

Polo et al., 1999, PNAS, vol. 96(8), pp. 4598-4603.*
Hahn et al, J Virol, 1990, 64:3069-3073.*
Hahn et al, PNAS, 1992, 89:2679-2683.*
Li et al, PNAS, 2004, 101:9429-9434.*
Perri et al, J Virol, 2003, 77:10394-10403.*
Polo et al, PNAS, 1999, 96:4598-4603.*
DiCiommo et al, J Biol Chem, 1998, 273:18060-18066.*
Lulla et al, J Virol, 2006, 80:3108-3111.*
Rayner et al, Rev Med Virol, 2002, 12:279-296.*
Frolov, et al. "Alphavirus-based expression vectors: Strategies and applications" Proceedings of the National Academy of Science, 93, 11371-11377 (1996).
Schlesinger, Sondra, "Alphaviruses—vectors for the expression of heterologous genes" TBTECH, 11, 8-22 (1993).
Strauss, et al., "Budding of alphaviruses", Trends in Microbiology, 3(9) (1995).
Greer et al., "Long-term Protection in Hamsters against Human Parainfluenza Virus Type 3 Following Mucosal or Combinations of Mucosal and Systemic Immunizations with Chimeric Alphavirus-based Replicon Particles", Scandinavian Journal of Immunology 66(6), 645-653 (2007).
Strauss et al. "Complete Nucleotide Sequence of the Genomic RNA of Sindbis Virus", Virology 133, 92-110, (1984).
Zhang, et al. "Identification and Characterization of Interferon-Induced Proteins That Inhibit Alphavirus Replication", Journal of Virology, 1246-11255, (2007).
Vander Veen, et al. "Alphavirus replicon vaccines", Animal Health Research Reviews, p. 1-9 (2012).

* cited by examiner

*Primary Examiner* — Michael Wilson
(74) *Attorney, Agent, or Firm* — Laurence Shumway; Helen Lee

(57) ABSTRACT

Strategies for increasing the productivity of alphavirus packaging cell lines and of reducing the possibility that replication competent virus may be generated during large scale production of recombinant alphavirus particles.

13 Claims, 15 Drawing Sheets

FIG. 3

3' end DH-Scap:    KGKTIKTTPEGTEEW↓
5' end of DH-Sgly:                MSAAPLVTAMCLLGNVSF
RCV:               KGKTIKTTPEGTEEW↓SAAPLVTAMCLLGNVSF

FIG. 4

```
                      (1) 1        10        20        30        40        50        60        76
Sindbis Virus Capsid  (1) -MNRGFFNMLGRRPFPAPTAMWRPRRRRQAAPMPARNGLASCIQQLTTAVSALVIGQATRPCFFRPRPPPR-----
SFV Capsid            (1) MNYIPTQTFYGRRWRPFPAARPWPLQATPVAPVVP-DFQAQQMQQLISAVNALTMRQNAIAFAPPPKPKKKK----
EEE Capsid            (1) MFPYPTLNYPPMAPINPMAYRDPNPPRRRWRPFRP--PLAAQIEDLRRSIANLTLKQPAPNPPAGPPAKRK-----
VEE Capsid            (1) -----MFPFQPMYPMQPMFYRNPFAAPRRFWFPRTDPFLAMQVQELTRSMANLTFKQRRDAFPEGPPAKKPKREAP
Consensus             (1) M   PTFNF PRRPIPPPAYR FP  RRR AFMRP  FLAAQIQQLTRAVANLTIKQPA AFF GPPPKKKK

(77) 77         90       100       110       120       130       140       152
Sindbis Virus Capsid (71) -------QKKQAPKQFPRPKKPKTQEKKKKQPAKPK----PGKRQRMALKLEADRLFDVKNEDGDVIGHALAMEGK
SFV Capsid           (72) -------TTKFKPKTQPRKINGKTQQQKKKDKQADKKKKKPGKRERMCMKIENDCIFEVKHEG-KVTGYACLVGDK
EEE Capsid           (70) ---------KFAPSLSLRRKKKRPFPPAKKQKRKPK----PGKRQPMCMKLESDKTFPIMLNG-QVNGYACVVGGR
VEE Capsid           (72) QKQKGGGQGKKKKNQGKKKAKTGPPNPKAQSGNKKKPNKKPGKRQRMVMKLESDKTFPIMLEG-KINGYACVVGGK
Consensus            (77)          Q KEKPKQ PKKKK KTQNFKKKQKNKPK   KKPGKRQPMCMKLESDKTFPIMLEG KVNGYACVVGGK H141  D147                   D163
                    (153) 153    160        170        180       190       200       210       228
Sindbis Virus Capsid(136) VMKPLHVKGTIDHPVLSKLKFTKSSAYDMEFAQLPVNMRSEAFTYTSEHPEGFYNWHHGAVQYSGGRFTIPRGVGG
SFV Capsid(140)           VMKPAHVKGVIDNADLAKLAFKRSSKYDLECAQIPVHMRSDASKYTHEKPEGHYNWHHGAVQYSGGRFTIPTGAGK
EEE Capsid(132)           VFKPLHVEGRIDNEQLAAIKLKKASIYDLEYGDVPQCMKSDTLQYTSDKPPGFYNWHHGAVQYENNPFTVPRGVGG
VEE Capsid(147)           LFRPMHVEGKIDNDVLAALRKTKKASKYDLEYADVPQNMRADTFKYTHEKPQGYYSWHHGAVQYENGRFTVPKGVGA
Consensus(153)            VMKPLHVKGKIDNDVLAKLKFKKASKYDLEYAQVPVNMRSDTFKYTSEKPEGFYNWHHGAVQYSNGRFTIPRGVGG S215                                              W264
                         229           ↓                                        281     ↓
Sindbis Virus Capsid (212) KGDSGRPIMDNSGRVVAIVLGGADEGTRTALSVVTWNSKGKTIKTTPEGTEEW
SFV Capsid           (216) KGDSGRPIFDNKGRVVAIVLGGANEGSRTALSVVTWN-KDMVTRVTPEGSEEW
EEE Capsid           (208) KGDSGRPILDNKGRVVAIVLGGVNEGSRTALSVVTWNQKGVTVKDTPEGSEPW
VEE Capsid           (223) KGDSGRPILDNQGRVVAIVLGGVNEGSRTALSVVMWNEKGVTVKITPENCEQW
Consensus            (229) KGDSGRPILDNKGRVVAIVLGGVNEGSRTALSVVTWN KGVTVK TPEGSEEW
```

FIG. 5A

| | | |
|---|---|---|
| VEE Nsp1-4 Codon Opti | (23) | TTGAAGAGGATTCACCATTTCTGCGGGCTCTCCAGCGCTCCTTTCCTCCAGTTCGAAGTTGAGCTAAACAGGTGACTGATCACGCCAACGCAAGAGC |
| VEE Nsp1-4 | (23) | TCGAGGAAGACAGCCCATTCCTCAGAGCTTTGCAGCGAGCTTCCCGCAGTTTGAGGTAGAAGCCAAGCCAGTCACTGATAATGACCATGCTAATGCCAGAGC |
| Consensus | (23) | T GA GA GA     CCATT CT G GCT T CAGCG  CTT CC CAGTT GA GT GA GC AA CAGGT ACTGA AATGA CA GC AA GC AGAGC |
| | (126) | 126         140         150         160         170         180         190         200         210         228 |
| VEE Nsp1-4 Codon Opti | (126) | ATTCAGCCATCTCGCCTCAAAGCTCATTGAGACAGAAGTCGATCCCTTGACACCATCTGGATATCGGTAGCGCCCGGCGAGGCCATGTACAGCAAACAC |
| VEE Nsp1-4 | (126) | GTTTTCGCATCTGGCTTCAAAACTGATCGAAAACGGAGGTGGACCATCCGACACAGATCCTTGACATTGGAAGTGCGCCCGCAGAATGTATTCTAAGCAC |
| Consensus | (126) | TT      CATCT GC TCAAA CT AT GA AC GA GT GA CC TC GACAC ATCCT GA AT GG AG GC CC GC  G G ATGTA     AA CAC |
| | (229) | 229         240         250         260         270         280         290         300         310         331 |
| VEE Nsp1-4 Codon Opti | (229) | AAATACCACTGCCTATGCCCTATGCGCTCGGCCGCAGAGGACCCCAGATAGGCTATACAAATACGCCACGAAACTCAAGAAGAATTGCAAAGAGATCACCGACAAAG |
| VEE Nsp1-4 | (229) | AAGTATCATTGTATCTGTCCGATGAGATGTGCCGAAGATCCGGACAGATTGTATAAGTATGCAACTAAGCTGAAGAAAAACTGTAAGGAAATAACTGATAAGG |
| Consensus | (229) | AA TA CA TG AT TG CC ATG G TG GC GA CC GA AG  T TA AA TA GC AC AA CT AAGAA AA TG AA GA AT AC GA AA G |
| | (332) | 332         340         350         360         370         380         390         400         410         434 |
| VEE Nsp1-4 Codon Opti | (332) | AGCTCGATAAAAAGATGAAAGAACTTGCGGCTGCGTGCTTGAGACAGAGACGATGTCTTGCACGATGATGAGAGTTGCCGCTATGAGGG |
| VEE Nsp1-4 | (332) | AATTGGACAAGAAAATGAAGGAGTCGCCGTCATGATGAACCTGACCTGAAACTGAGACTATGTGCCTCCACGACGAGTCGTTGCCTACGAAGG |
| Consensus | (332) | A    T GA AA AA ATGAA GA CT GC GC GT GA AC GAGAC ATGTGC T CACGA GA GAG     TG CGCTA GA GG |
| | (435) | 435         440         450         460         470         480         490         500         510         537 |
| VEE Nsp1-4 Codon Opti | (435) | CCAGGTGGCGGTGTACCAGGAGACTCTATGCAGGATAGTAGTAGATGGGCCAACTTCTCTTTACCATCAAGCTAACAAGGTGTGCGGGTCGCTTATTGGATCGGGTTTGAT |
| VEE Nsp1-4 | (435) | GCAAGTCGCTGTTTACCAGGATGTATACGGGTTGACGGACCGACAAGTCTTATCACCAAGCTCTATCACCAAGCCAATAAGGAGTTAGAGTGCCTACTGGATAGGCTTTGAC |
| Consensus | (435) | CA GT GC GT TACCAGGA GT TA GC GT GA GT GA GG CC AC     TCT TA CA CAAGC AA AA GG GT  G GTCGC TA TGGAT GG TTTGA |
| | (538) | 538         550         560         570         580         590         600         610         620         640 |
| VEE Nsp1-4 Codon Opti | (538) | ACTACACCATTCATGTTCAAGAATCATGGCAGGGCCTACCAAGCTACAGCACAGAGCACAAATTGGGCACAGACGAGAGGTGTTAACGGCACCGAATATCGGGCTGTTT |
| VEE Nsp1-4 | (538) | ACCACCCCTTTTATGTTAAGAACTTGGCTGAGCATATCCATCATATCTACCATGATACTCTCCAACTGTTAACCGTTAACGGCTCGTAACATAGGCCTATGCA |
| Consensus | (538) | AC AC CC TT ATGTT AAGAA  TGGC GG GC TA CCA     TAC    AC AA TGGGC GACGA AC GTGTTAACGGC CG AA AT GG CT TG |

|  | 1262 | 1270 | 1280 | 1290 | 1300 | 1310 | 1320 | 1330 | 1340 | 1350 | 1364 |
VEE Nsp1-4 Codon Opt(1262) GGGCCTTCAGGCGCCACAAAATCACAAGTATCTACAAAAGGCCTGACACGCAAACAATAATAAAGTGAATTCCGACTTTCACTCTTTTGTTCTGCCAAGAAT
VEE Nsp1-4(1262) GGGCTTTTAGAAGGCACAAGATAACATCTATTTATAGCGCCCGGATACCCAAACCATCATCAAAGTGAACAGCGATTTCCACTCATTCGTCGTCGCCAGGAT
Consensus(1262) GGGC TT AG G CACACA AT ACA  TAT TA AA  G CC GA AC CAAAC AT AT AAGTGAA    CGA TT CACTC TT GT CTGCC AG AT

|  | 1365 | 1370 | 1380 | 1390 | 1400 | 1410 | 1420 | 1430 | 1440 | 1450 | 1467 |
VEE Nsp1-4 Codon Opt(1365) AGGTAGCAACACTCTGGAAATCGGGCTCAGGACCAGAATACCAGAGACCACCAAGGAACCCTCTCCTTTGATCACGGCAGGAGGACGTGCAGGAA
VEE Nsp1-4(1365) AGGCAGTAACACATTGGAGATCGGGCTGAGAACAAGAATCAGGAGAACATGTTAGAGGAGCACAAGGAGCCGTCACCTCTCATTACCGCCGAGGACGTACAAGAA
Consensus(1365) AGG AG AACAC  TGGA ATCGGGCT AG AC AGAAT  G AAAATG T GA GA CACAAGGA CC TC CCT T AT AC GC GAGGACGT CA GAA

|  | 1468 | 1480 | 1490 | 1500 | 1510 | 1520 | 1530 | 1540 | 1550 | 1560 | 1570 |
VEE Nsp1-4 Codon Opt(1468) GCAAAATGCGCCGCAGACGAAGCTAAAGAAGTTCCGGAGCGGAGAACTGCGAGCGGCTCTGCCACCCTGGCGGCTGACGTCGAGGAACCCACCTGGAGG
VEE Nsp1-4(1468) GCTAAGTGCGCAGCCGATGAGCTGAAGGAGTTGCGTGAAGCCGAGGAGTTGCGCGAAGAGGCCTGACCTCTGCCTGCAGCTGATGTTGAGGAGCCCACTCTGAAG
Consensus(1468) GC AA  TGCGC GC GA GA GCTAA GA GT CG GA GA GA  TGCG GC GCTCT CCACC  TGGC GCTGA GT GAGGA CCCAC CTGA G

|  | 1571 | 1580 | 1590 | 1600 | 1610 | 1620 | 1630 | 1640 | 1650 | 1660 | 1673 |
VEE Nsp1-4 Codon Opt(1571) CAGATGTGGATCTGATGCTTCAGGAAGCGGGAGCCGGGCTCCGTCGAGACCCCCAGAGGGTTGATCAAAGTGACATCCTATGCAGGAGAAGACAAAATCGGGAG
VEE Nsp1-4(1571) CCGATGTCGACTTGATGTTACAAGAGCGTGGGGCCCGGCCTGGGGCCGCTCAGTGGAGACACCTCTGGCTTGATAAAGGTTACCAGCTACGCTGGCGAGGACAAGATCGGCTC
Consensus(1571) C GATGT GA  TGATG T CA GA GC GG GCCGG TC GTGGAGAC CC  G GG TTGAT AA GT AC   CTA GC GG GA GACAA ATCGG

|  | 1674 | 1680 | 1690 | 1700 | 1710 | 1720 | 1730 | 1740 | 1750 | 1760 | 1776 |
VEE Nsp1-4 Codon Opt(1674) CTATGCCGTTTTGTCCCCACAGGCTGTCTTAAATCTGAGAAACTCTGCCGACATCTCCGCCGAACAGGTCATTGATCACATAGCGGACGGAAG
VEE Nsp1-4(1674) TTACGCTGTGCTTTCTGCCTCCCGCAGGCTGTACTCAAGAGTGAAAAAATTATCTTGCATCCACCCTTCTGCTGAACAAGTCATATAGTGATAACACACTCTGCCGAAAA
Consensus(1674) TA GC GT  T TC CC CAGGCTGT CT AA    TGA AAA T TC TGCAT CA CC CTCGC GAACA GTCAT GTGAT ACACA    GG CG AA

|  | 1777 | 1790 | 1800 | 1810 | 1820 | 1830 | 1840 | 1850 | 1860 | 1879 |
VEE Nsp1-4 Codon Opt(1777) GGCAGGTATGCTGTGAACCCTATCACGGCAAAGTAGTCGTGCCCGAGGGACACGCCATTCCGGTGCAAGATTTCCAGGCACTCAGCGAATCCGCCACAATCG
VEE Nsp1-4(1777) GGGCGTTATGCCGTGAACCATACCATGGTGTGCCAGAGGAGTAGTGTGCCAGAGGGACATGCAATACCGTCCAGACTTTCAAGCTCTGAGTGAACTCTGAGTGAAGTGCCACCATTG
Consensus(1777) GG  G TATGC GTGGAACC TA CA GG AAAGTAGT GTGCC GAGGGACA GC AT CC GT CA GA TT CA GC CT AG GAA    GCCAC AT G

FIG. 5D

```
                     (1880) 1880         1890        1900        1910        1920        1930        1940        1950        1960        1970      1982
VEE Nsp1-4 Codon Opt(1880) TATACAATGAACGCGAGTTTGTGAACAGGTACCTC

```
                    (7431) 7431        7440        7450        7460        7470        7480        7490        7500        7510        7520        7533
VEE Nsp1-4 Codon Opt(7430) CATCCATCATCGTCATGGCAATGACCACCTTGGCCAGTCAGTCAAATCTTTTTCTTAT

SEQUENCE LISTING

<160> NUMBER OF SEQ ID NOS: 39

<210> SEQ ID NO 1
<211> LENGTH: 264
<212> TYPE: PRT
<213> ORGANISM: Sindbis virus

<400> SEQUENCE: 1

Met Asn Arg Gly Phe Phe Asn Met Leu Gly Arg Arg Pro Phe Pro Ala
1               5                   10                  15

Pro Thr Ala Met Trp Arg Pro Arg Arg Arg Gln Ala Ala Pro Met
            20                  25                  30

Pro Ala Arg Asn Gly Leu Ala Ser Gln Ile Gln Gln Leu Thr Thr Ala
            35                  40                  45

Val Ser Ala Leu Val Ile Gly Gln Ala Thr Arg Pro Gln Pro Pro Arg
        50                  55                  60

Pro Arg Pro Pro Pro Arg Gln Lys Lys Gln Ala Pro Lys Gln Pro Pro
65                  70                  75                  80

-continued

```
Lys Pro Lys Lys Pro Lys Thr Gln Glu Lys Lys Lys Gln Pro Ala
                85                  90                  95
Lys Pro Lys Pro Gly Lys Arg Gln Arg Met Ala Leu Lys Leu Glu Ala
            100                 105                 110
Asp Arg Leu Phe Asp Val Lys Asn Glu Asp Gly Asp Val Ile Gly His
            115                 120                 125
Ala Leu Ala Met Glu Gly Lys Val Met Lys Pro Leu His Val Lys Gly
130                 135                 140
Thr Ile Asp His Pro Val Leu Ser Lys Leu Lys Phe Thr Lys Ser Ser
145                 150                 155                 160
Ala Tyr Asp Met Glu Phe Ala Gln Leu Pro Val Asn Met Arg Ser Glu
                165                 170                 175
Ala Phe Thr Tyr Thr Ser Glu His Pro Glu Gly Phe Tyr Asn Trp His
            180                 185                 190
His Gly Ala Val Gln Tyr Ser Gly Gly Arg Phe Thr Ile Pro Arg Gly
            195                 200                 205
Val Gly Gly Arg Gly Asp Ser Gly Arg Pro Ile Met Asp Asn Ser Gly
            210                 215                 220
Arg Val Val Ala Ile Val Leu Gly Gly Ala Asp Glu Gly Thr Arg Thr
225                 230                 235                 240
Ala Leu Ser Val Val Thr Trp Asn Ser Lys Gly Lys Thr Ile Lys Thr
                245                 250                 255
Thr Pro Glu Gly Thr Glu Glu Trp
                260

<210> SEQ ID NO 2
<211> LENGTH: 267
<212> TYPE: PRT
<213> ORGANISM: Semliki Forest virus

<400> SEQUENCE: 2

Met Asn Tyr Ile Pro Thr Gln Thr Phe Tyr Gly Arg Arg Trp Arg Pro
 1                5                  10                  15
Arg Pro Ala Ala Arg Pro Trp Pro Leu Gln Ala Thr Pro Val Ala Pro
            20                  25                  30
Val Val Pro Asp Phe Gln Ala Gln Gln Met Gln Gln Leu Ile Ser Ala
            35                  40                  45
Val Asn Ala Leu Thr Met Arg Gln Asn Ala Ile Ala Pro Ala Arg Pro
50                  55                  60
Pro Lys Pro Lys Lys Lys Thr Thr Lys Pro Lys Pro Lys Thr Gln
65                  70                  75                  80
Pro Lys Lys Ile Asn Gly Lys Thr Gln Gln Gln Lys Lys Lys Asp Lys
                85                  90                  95
Gln Ala Asp Lys Lys Lys Lys Pro Gly Lys Arg Glu Arg Met Cys
            100                 105                 110
Met Lys Ile Glu Asn Asp Cys Ile Phe Glu Val Lys His Glu Gly Lys
            115                 120                 125
Val Thr Gly Tyr Ala Cys Leu Val Gly Asp Lys Val Met Lys Pro Ala
130                 135                 140
His Val Lys Gly Val Ile Asp Asn Ala Asp Leu Ala Lys Ile Ala Phe
145                 150                 155                 160
Lys Lys Ser Ser Lys Tyr Asp Leu Glu Cys Ala Gln Ile Pro Val His
                165                 170                 175
Met Arg Ser Asp Ala Ser Lys Tyr Thr His Glu Lys Pro Glu Gly His
```

```
                  180                 185                 190

Tyr Asn Trp His His Gly Ala Val Gln Tyr Ser Gly Gly Arg Phe Thr
            195                 200                 205

Ile Pro Thr Gly Ala Gly Lys Pro Gly Asp Ser Gly Arg Pro Ile Phe
    210                 215                 220

Asp Asn Lys Gly Arg Val Val Ala Ile Val Leu Gly Gly Ala Asn Glu
225                 230                 235                 240

Gly Ser Arg Thr Ala Leu Ser Val Val Thr Trp Asn Lys Asp Met Val
            245                 250                 255

Thr Arg Val Thr Pro Glu Gly Ser Glu Glu Trp
            260                 265

<210> SEQ ID NO 3
<211> LENGTH: 131
<212> TYPE: PRT
<213> ORGANISM: Eastern equine encephalitis virus

<400> SEQUENCE: 3

Met Phe Pro Tyr Pro Thr Leu Asn Tyr Pro Pro Met Ala Pro Ile Asn
1               5                   10                  15

Pro Met Ala Tyr Arg Asp Pro Asn Pro Pro Arg Arg Arg Trp Arg Pro
            20                  25                  30

Phe Arg Pro Pro Leu Ala Ala Gln Ile Glu Asp Leu Arg Arg Ser Ile
        35                  40                  45

Ala Asn Leu Thr Leu Lys Gln Arg Ala Pro Asn Pro Pro Ala Gly Pro
    50                  55                  60

Pro Ala Lys Arg Lys Lys Pro Ala Pro Ser Leu Ser Leu Arg Arg Lys
65                  70                  75                  80

Lys Lys Arg Pro Pro Pro Ala Lys Lys Gln Lys Arg Lys Pro Lys Pro
            85                  90                  95

Pro Gly Lys Arg Gln Arg Met Cys Met Lys Leu Glu Ser Asp Lys Thr
        100                 105                 110

Phe Pro Ile Met Leu Asn Gly Gln Val Asn Gly Tyr Ala Cys Val Val
    115                 120                 125

Gly Gly Arg
    130

<210> SEQ ID NO 4
<211> LENGTH: 129
<212> TYPE: PRT
<213> ORGANISM: Venezuelan encephalitis virus

<400> SEQUENCE: 4

Val Phe Lys Pro Leu His Val Glu Gly Arg Ile Asp Asn Glu Gln Leu
1               5                   10                  15

Ala Ala Ile Lys Leu Lys Lys Ala Ser Ile Tyr Asp Leu Glu Tyr Gly
            20                  25                  30

Asp Val Pro Gln Cys Met Lys Ser Asp Thr Leu Gln Tyr Thr Ser Asp
        35                  40                  45

Lys Pro Pro Gly Phe Tyr Asn Trp His His Gly Ala Val Gln Tyr Glu
    50                  55                  60

Asn Asn Arg Phe Thr Val Pro Arg Gly Val Gly Lys Gly Asp Ser
65                  70                  75                  80

Gly Arg Pro Ile Leu Asp Asn Lys Gly Arg Val Val Ala Ile Val Leu
            85                  90                  95

Gly Gly Val Asn Glu Gly Ser Arg Thr Ala Leu Ser Val Val Thr Trp
```

```
                    100                 105                 110
Asn Gln Lys Gly Val Thr Val Lys Asp Thr Pro Glu Gly Ser Glu Pro
            115                 120                 125

Trp

<210> SEQ ID NO 5
<211> LENGTH: 281
<212> TYPE: PRT
<213> ORGANISM: Artificial Sequence
<220> FEATURE:
<223> OTHER INFORMATION: consensus sequence
<221> NAME/KEY: VARIANT
<222> LOCATION: (1)...(281)
<223> OTHER INFORMATION: Xaa = Any Amino Acid
<221> NAME/KEY: VARIANT
<222> LOCATION: (1)...(281)
<223> OTHER INFORMATION: Xaa = Any Amino Acid

<400> SEQUENCE: 5

Met Xaa Xaa Xaa Pro Thr Phe Asn Phe Xaa Pro Arg Arg Pro Ile Pro
  1               5                  10                  15

Pro Pro Ala Tyr Arg Xaa Pro Pro Xaa Xaa Arg Arg Arg Xaa Ala Pro
             20                  25                  30

Met Arg Pro Xaa Xaa Phe Leu Ala Ala Gln Ile Gln Gln Leu Thr Arg
         35                  40                  45

Ala Val Ala Asn Leu Thr Ile Lys Gln Arg Ala Xaa Ala Pro Pro Xaa
     50                  55                  60

Gly Pro Pro Pro Lys Lys Lys Xaa Xaa Xaa Xaa Xaa Xaa Xaa Xaa Xaa
 65                  70                  75                  80

Xaa Xaa Xaa Gln Xaa Lys Pro Lys Pro Lys Gln Xaa Pro Lys Lys Lys
                 85                  90                  95

Lys Xaa Lys Thr Gln Asn Pro Lys Lys Gln Lys Asn Lys Pro Lys
            100                 105                 110

Xaa Xaa Lys Lys Pro Gly Lys Arg Gln Arg Met Cys Met Lys Leu Glu
            115                 120                 125

Ser Asp Lys Thr Phe Pro Ile Met Leu Glu Gly Xaa Lys Val Asn Gly
    130                 135                 140

Tyr Ala Cys Val Val Gly Gly Lys Val Met Lys Pro Leu His Val Lys
145                 150                 155                 160

Gly Lys Ile Asp Asn Asp Val Leu Ala Lys Leu Lys Phe Lys Lys Ala
                165                 170                 175

Ser Lys Tyr Asp Leu Glu Tyr Ala Gln Val Pro Val Asn Met Arg Ser
            180                 185                 190

Asp Thr Phe Lys Tyr Thr Ser Glu Lys Pro Glu Gly Phe Tyr Asn Trp
        195                 200                 205

His His Gly Ala Val Gln Tyr Ser Asn Gly Arg Phe Thr Ile Pro Arg
    210                 215                 220

Gly Val Gly Gly Lys Gly Asp Ser Gly Arg Pro Ile Leu Asp Asn Lys
225                 230                 235                 240

Gly Arg Val Val Ala Ile Val Leu Gly Gly Val Asn Glu Gly Ser Arg
                245                 250                 255

Thr Ala Leu Ser Val Val Thr Trp Asn Xaa Lys Gly Val Thr Val Lys
            260                 265                 270

Xaa Thr Pro Glu Gly Ser Glu Glu Trp
        275                 280

<210> SEQ ID NO 6
```

```
<211> LENGTH: 535
<212> TYPE: PRT
<213> ORGANISM: Alphavirus

<400> SEQUENCE: 6

Met Glu Lys Val His Val Asp Ile Glu Glu Ser Pro Phe Leu Arg
 1               5                  10                  15

Ala Leu Gln Arg Ser Phe Pro Gln Phe Glu Val Glu Ala Lys Gln Val
            20                  25                  30

Thr Asp Asn Asp His Ala Asn Ala Arg Ala Phe Ser His Leu Ala Ser
            35                  40                  45

Lys Leu Ile Glu Thr Glu Val Asp Pro Ser Thr Ile Leu Asp Ile
 50                  55                  60

Gly Ser Ala Pro Ala Arg Arg Met Tyr Ser Lys His Lys Tyr His Cys
 65                  70                  75                  80

Ile Cys Pro Met Arg Cys Ala Glu Asp Pro Asp Arg Leu Tyr Lys Tyr
                85                  90                  95

Ala Thr Lys Leu Lys Lys Asn Cys Lys Glu Ile Thr Asp Lys Glu Leu
            100                 105                 110

Asp Lys Lys Met Lys Glu Leu Ala Ala Val Met Ser Asp Pro Asp Leu
            115                 120                 125

Glu Thr Glu Thr Met Cys Leu His Asp Asp Glu Ser Cys Arg Tyr Glu
            130                 135                 140

Gly Gln Val Ala Val Tyr Gln Asp Val Tyr Ala Val Asp Gly Pro Thr
145                 150                 155                 160

Ser Leu Tyr His Gln Ala Asn Lys Gly Val Arg Val Ala Tyr Trp Ile
                165                 170                 175

Gly Phe Asp Thr Thr Pro Phe Met Phe Lys Asn Leu Ala Gly Ala Tyr
            180                 185                 190

Pro Ser Tyr Ser Thr Asn Trp Ala Asp Glu Thr Val Leu Thr Ala Arg
        195                 200                 205

Asn Ile Gly Leu Cys Ser Ser Asp Val Met Glu Arg Ser Arg Arg Gly
    210                 215                 220

Met Ser Ile Leu Arg Lys Lys Tyr Leu Lys Pro Ser Asn Asn Val Leu
225                 230                 235                 240

Phe Ser Val Gly Ser Thr Ile Tyr His Glu Lys Arg Asp Leu Leu Arg
                245                 250                 255

Ser Trp His Leu Pro Ser Val Phe His Leu Arg Gly Lys Gln Asn Tyr
            260                 265                 270

Thr Cys Arg Cys Glu Thr Ile Val Ser Cys Asp Gly Tyr Val Val Lys
            275                 280                 285

Arg Ile Ala Ile Ser Pro Gly Leu Tyr Gly Lys Pro Ser Gly Tyr Ala
    290                 295                 300

Ala Thr Met His Arg Glu Gly Phe Leu Cys Cys Lys Val Thr Asp Thr
305                 310                 315                 320

Leu Asn Gly Glu Arg Val Ser Phe Pro Val Cys Thr Tyr Val Pro Ala
                325                 330                 335

Thr Leu Cys Asp Gln Met Thr Gly Ile Leu Ala Thr Asp Val Ser Ala
            340                 345                 350

Asp Asp Ala Gln Lys Leu Leu Val Gly Leu Asn Gln Arg Ile Val Val
        355                 360                 365

Asn Gly Arg Thr Gln Arg Asn Thr Asn Thr Met Lys Asn Tyr Leu Leu
    370                 375                 380

Pro Val Val Ala Gln Ala Phe Ala Arg Trp Ala Lys Glu Tyr Lys Glu
```

```
                    385                 390                 395                 400
Asp Gln Glu Asp Glu Arg Pro Leu Gly Leu Arg Asp Arg Gln Leu Val
                        405                 410                 415

Met Gly Cys Cys Trp Ala Phe Arg Arg His Lys Ile Thr Ser Ile Tyr
                420                 425                 430

Lys Arg Pro Asp Thr Gln Thr Ile Ile Lys Val Asn Ser Asp Phe His
                435                 440                 445

Ser Phe Val Leu Pro Arg Ile Gly Ser Asn Thr Leu Glu Ile Gly Leu
        450                 455                 460

Arg Thr Arg Ile Arg Lys Met Leu Glu Glu His Lys Glu Pro Ser Pro
465                 470                 475                 480

Leu Ile Thr Ala Glu Asp Val Gln Glu Ala Lys Cys Ala Ala Asp Glu
                485                 490                 495

Ala Lys Glu Val Arg Glu Ala Glu Leu Arg Ala Ala Leu Pro Pro
                500                 505                 510

Leu Ala Ala Asp Val Glu Glu Pro Thr Leu Glu Ala Asp Val Asp Leu
        515                 520                 525

Met Leu Gln Glu Ala Gly Ala
        530                 535

<210> SEQ ID NO 7
<211> LENGTH: 794
<212> TYPE: PRT
<213> ORGANISM: Alphavirus

<400> SEQUENCE: 7

Gly Ser Val Glu Thr Pro Arg Gly Leu Ile Lys Val Thr Ser Tyr Ala
  1               5                  10                  15

Gly Glu Asp Lys Ile Gly Ser Tyr Ala Val Leu Ser Pro Gln Ala Val
                 20                  25                  30

Leu Lys Ser Glu Lys Leu Ser Cys Ile His Pro Leu Ala Glu Gln Val
             35                  40                  45

Ile Val Ile Thr His Ser Gly Arg Lys Gly Arg Tyr Ala Val Glu Pro
     50                  55                  60

Tyr His Gly Lys Val Val Pro Glu Gly His Ala Ile Pro Val Gln
65                   70                  75                  80

Asp Phe Gln Ala Leu Ser Glu Ser Ala Thr Ile Val Tyr Asn Glu Arg
                 85                  90                  95

Glu Phe Val Asn Arg Tyr Leu His His Ile Ala Thr His Gly Gly Ala
                100                 105                 110

Leu Asn Thr Asp Glu Glu Tyr Tyr Lys Thr Val Lys Pro Ser Glu His
            115                 120                 125

Asp Gly Glu Tyr Leu Tyr Asp Ile Asp Arg Lys Gln Cys Val Lys Lys
        130                 135                 140

Glu Leu Val Thr Gly Leu Gly Leu Thr Gly Glu Leu Val Asp Pro Pro
145                 150                 155                 160

Phe His Glu Phe Ala Tyr Glu Ser Leu Arg Thr Arg Pro Ala Ala Pro
                165                 170                 175

Tyr Gln Val Pro Thr Ile Gly Val Tyr Gly Val Pro Gly Ser Gly Lys
            180                 185                 190

Ser Gly Ile Ile Lys Ser Ala Val Thr Lys Lys Asp Leu Val Val Ser
        195                 200                 205

Ala Lys Lys Glu Asn Cys Ala Glu Ile Ile Arg Asp Val Lys Lys Met
    210                 215                 220
```

-continued

Lys Gly Leu Asp Val Asn Ala Arg Thr Val Asp Ser Val Leu Leu Asn
225                 230                 235                 240

Gly Cys Lys His Pro Val Glu Thr Leu Tyr Ile Asp Glu Ala Phe Ala
            245                 250                 255

Cys His Ala Gly Thr Leu Arg Ala Leu Ile Ala Ile Arg Pro Lys
                260                 265                 270

Lys Ala Val Leu Cys Gly Asp Pro Lys Gln Cys Gly Phe Phe Asn Met
        275                 280                 285

Met Cys Leu Lys Val His Phe Asn His Glu Ile Cys Thr Gln Val Phe
    290                 295                 300

His Lys Ser Ile Ser Arg Arg Cys Thr Lys Ser Val Thr Ser Val Val
305                 310                 315                 320

Ser Thr Leu Phe Tyr Asp Lys Lys Met Arg Thr Thr Asn Pro Lys Glu
                325                 330                 335

Thr Lys Ile Val Ile Asp Thr Thr Gly Ser Thr Lys Pro Lys Gln Asp
                340                 345                 350

Asp Leu Ile Leu Thr Cys Phe Arg Gly Trp Val Lys Gln Leu Gln Ile
            355                 360                 365

Asp Tyr Lys Gly Asn Glu Ile Met Thr Ala Ala Ser Gln Gly Leu
370                 375                 380

Thr Arg Lys Gly Val Tyr Ala Val Arg Tyr Lys Val Asn Glu Asn Pro
385                 390                 395                 400

Leu Tyr Ala Pro Thr Ser Glu His Val Asn Val Leu Leu Thr Arg Thr
                405                 410                 415

Glu Asp Arg Ile Val Trp Lys Thr Leu Ala Gly Asp Pro Trp Ile Lys
            420                 425                 430

Thr Leu Thr Ala Lys Tyr Pro Gly Asn Phe Thr Ala Thr Ile Glu Glu
        435                 440                 445

Trp Gln Ala Glu His Asp Ala Ile Met Arg His Ile Leu Glu Arg Pro
    450                 455                 460

Asp Pro Thr Asp Val Phe Gln Asn Lys Ala Asn Val Cys Trp Ala Lys
465                 470                 475                 480

Ala Leu Val Pro Val Leu Lys Thr Ala Gly Ile Asp Met Thr Thr Glu
                485                 490                 495

Gln Trp Asn Thr Val Asp Tyr Phe Glu Thr Asp Lys Ala His Ser Ala
            500                 505                 510

Glu Ile Val Leu Asn Gln Leu Cys Val Arg Phe Phe Gly Leu Asp Leu
        515                 520                 525

Asp Ser Gly Leu Phe Ser Ala Pro Thr Val Pro Leu Ser Ile Arg Asn
    530                 535                 540

Asn His Trp Asp Asn Ser Pro Ser Pro Asn Met Tyr Gly Leu Asn Lys
545                 550                 555                 560

Glu Val Val Arg Gln Leu Ser Arg Arg Tyr Pro Gln Leu Pro Arg Ala
                565                 570                 575

Val Ala Thr Gly Arg Val Tyr Asp Met Asn Thr Gly Thr Leu Arg Asn
            580                 585                 590

Tyr Asp Pro Arg Ile Asn Leu Val Pro Val Asn Arg Arg Leu Pro His
        595                 600                 605

Ala Leu Val Leu His His Asn Glu His Pro Gln Ser Asp Phe Ser Ser
    610                 615                 620

Phe Val Ser Lys Leu Lys Gly Arg Thr Val Leu Val Val Gly Glu Lys
625                 630                 635                 640

Leu Ser Val Pro Gly Lys Met Val Asp Trp Leu Ser Asp Arg Pro Glu

```
                    645                 650                 655
Ala Thr Phe Arg Ala Arg Leu Asp Leu Gly Ile Pro Gly Asp Val Pro
            660                 665                 670

Lys Tyr Asp Ile Ile Phe Val Asn Val Arg Thr Pro Tyr Lys Tyr His
        675                 680                 685

His Tyr Gln Gln Cys Glu Asp His Ala Ile Lys Leu Ser Met Leu Thr
    690                 695                 700

Lys Lys Ala Cys Leu His Leu Asn Pro Gly Gly Thr Cys Val Ser Ile
705                 710                 715                 720

Gly Tyr Gly Tyr Ala Asp Arg Ala Ser Glu Ser Ile Ile Gly Ala Ile
            725                 730                 735

Ala Arg Gln Phe Lys Phe Ser Arg Val Cys Lys Pro Lys Ser Ser Leu
        740                 745                 750

Glu Glu Thr Glu Val Leu Phe Val Phe Ile Gly Tyr Asp Arg Lys Ala
    755                 760                 765

Arg Thr His Asn Pro Tyr Lys Leu Ser Ser Thr Leu Thr Asn Ile Tyr
770                 775                 780

Thr Gly Ser Arg Leu His Glu Ala Gly Cys
785                 790

<210> SEQ ID NO 8
<211> LENGTH: 563
<212> TYPE: PRT
<213> ORGANISM: Alphavirus

<400> SEQUENCE: 8

Ala Pro Ser Tyr His Val Val Arg Gly Asp Ile Ala Thr Ala Thr Glu
 1               5                  10                  15

Gly Val Ile Ile Asn Ala Ala Asn Ser Lys Gly Gln Pro Gly Gly Gly
            20                  25                  30

Val Cys Gly Ala Leu Tyr Lys Lys Phe Pro Glu Ser Phe Asp Leu Gln
        35                  40                  45

Pro Ile Glu Val Gly Lys Ala Arg Leu Val Lys Gly Ala Ala Lys His
    50                  55                  60

Ile Ile His Ala Val Gly Pro Asn Phe Asn Lys Val Ser Glu Val Glu
65                  70                  75                  80

Gly Asp Lys Gln Leu Ala Glu Ala Tyr Glu Ser Ile Ala Lys Ile Val
            85                  90                  95

Asn Asp Asn Asn Tyr Lys Ser Val Ala Ile Pro Leu Leu Ser Thr Gly
            100                 105                 110

Ile Phe Ser Gly Asn Lys Asp Arg Leu Thr Gln Ser Leu Asn His Leu
        115                 120                 125

Leu Thr Ala Leu Asp Thr Thr Asp Ala Asp Val Ala Ile Tyr Cys Arg
    130                 135                 140

Asp Lys Lys Trp Glu Met Thr Leu Lys Glu Ala Val Ala Arg Arg Glu
145                 150                 155                 160

Ala Val Glu Glu Ile Cys Ile Ser Asp Asp Ser Ser Val Thr Glu Pro
            165                 170                 175

Asp Ala Glu Leu Val Arg Val His Pro Lys Ser Ser Leu Ala Gly Arg
        180                 185                 190

Lys Gly Tyr Ser Thr Ser Asp Gly Lys Thr Phe Ser Tyr Leu Glu Gly
    195                 200                 205

Thr Lys Phe His Gln Ala Ala Lys Asp Ile Ala Glu Ile Asn Ala Met
    210                 215                 220
```

```
Trp Pro Val Ala Thr Glu Ala Asn Glu Gln Val Cys Met Tyr Ile Leu
225                 230                 235                 240

Gly Glu Ser Met Ser Ser Ile Arg Ser Lys Cys Pro Val Glu Glu Ser
            245                 250                 255

Glu Ala Ser Ser Pro Ser Thr Leu Pro Cys Leu Cys Ile His Ala
        260                 265                 270

Met Thr Pro Glu Arg Val Gln Arg Leu Lys Ala Ser Arg Pro Glu Gln
        275                 280                 285

Ile Thr Val Cys Ser Ser Phe Pro Leu Pro Lys Tyr Arg Ile Thr Gly
        290                 295                 300

Val Gln Lys Ile Gln Cys Ser Gln Pro Ile Leu Phe Ser Pro Lys Val
305                 310                 315                 320

Pro Ala Tyr Ile His Pro Arg Lys Tyr Leu Val Glu Thr Pro Pro Val
                325                 330                 335

Asp Glu Thr Pro Glu Pro Ser Ala Glu Asn Gln Ser Thr Glu Gly Thr
        340                 345                 350

Pro Glu Gln Pro Pro Leu Ile Thr Glu Asp Glu Thr Arg Thr Arg Thr
        355                 360                 365

Pro Glu Pro Ile Ile Ile Glu Glu Glu Glu Asp Ser Ile Ser Leu
370                 375                 380

Leu Ser Asp Gly Pro Thr His Gln Val Leu Gln Val Glu Ala Asp Ile
385                 390                 395                 400

His Gly Pro Pro Ser Val Ser Ser Ser Trp Ser Ile Pro His Ala
                405                 410                 415

Ser Asp Phe Asp Val Asp Ser Leu Ser Ile Leu Asp Thr Leu Glu Gly
            420                 425                 430

Ala Ser Val Thr Ser Gly Ala Thr Ser Ala Glu Thr Asn Ser Tyr Phe
        435                 440                 445

Ala Lys Ser Met Glu Phe Leu Ala Arg Pro Val Pro Ala Pro Arg Thr
        450                 455                 460

Val Phe Arg Asn Pro Pro His Pro Ala Pro Arg Thr Arg Thr Pro Ser
465                 470                 475                 480

Leu Ala Pro Ser Arg Ala Cys Ser Arg Gly Ile Thr Gly Glu Thr Val
                485                 490                 495

Gly Tyr Ala Val Thr His Asn Ser Glu Gly Phe Leu Leu Cys Lys Val
            500                 505                 510

Thr Asp Thr Val Lys Gly Glu Arg Val Ser Phe Pro Val Cys Thr Tyr
        515                 520                 525

Ile Pro Ala Thr Ile Asn Ser Arg Thr Ser Leu Val Ser Asn Pro Pro
        530                 535                 540

Gly Val Asn Arg Val Ile Thr Arg Glu Glu Phe Glu Ala Phe Val Ala
545                 550                 555                 560

Gln Gln Gln

<210> SEQ ID NO 9
<211> LENGTH: 606
<212> TYPE: PRT
<213> ORGANISM: Alphavirus

<400> SEQUENCE: 9

Tyr Ile Phe Ser Ser Asp Thr Gly Gln Gly His Leu Gln Gln Lys Ser
1               5                   10                  15

Val Arg Gln Thr Val Leu Ser Glu Val Val Leu Glu Arg Thr Glu Leu
            20                  25                  30
```

```
Glu Ile Ser Tyr Ala Pro Arg Leu Asp Gln Lys Glu Leu Leu
        35                  40                  45

Arg Lys Lys Leu Gln Leu Asn Pro Thr Pro Ala Asn Arg Ser Arg Tyr
 50                  55                  60

Gln Ser Arg Lys Val Glu Asn Met Lys Ala Ile Thr Ala Arg Arg Ile
 65              70                  75                      80

Leu Gln Gly Leu Gly His Tyr Leu Lys Ala Glu Gly Lys Val Glu Cys
                    85                  90                  95

Tyr Arg Thr Leu His Pro Val Pro Leu Tyr Ser Ser Val Asn Arg
                100             105                 110

Ala Phe Ser Ser Pro Lys Val Ala Val Glu Ala Cys Asn Ala Met Leu
            115                 120                 125

Lys Glu Asn Phe Pro Thr Val Ala Ser Tyr Cys Ile Ile Pro Glu Tyr
    130                 135                 140

Asp Ala Tyr Leu Asp Met Val Asp Gly Ala Ser Cys Cys Leu Asp Thr
145                 150                 155                 160

Ala Ser Phe Cys Pro Ala Lys Leu Arg Ser Phe Pro Lys Lys His Ser
                165                 170                 175

Tyr Leu Glu Pro Thr Ile Arg Ser Ala Val Pro Ser Ala Ile Gln Asn
            180                 185                 190

Thr Leu Gln Asn Val Leu Ala Ala Thr Lys Arg Asn Cys Asn Val
        195                 200                 205

Thr Gln Met Arg Glu Leu Pro Val Leu Asp Ser Ala Ala Phe Asn Val
    210                 215                 220

Glu Cys Phe Lys Lys Tyr Ala Cys Asn Asn Glu Tyr Trp Glu Thr Phe
225                 230                 235                 240

Lys Glu Asn Pro Ile Arg Leu Thr Glu Glu Asn Val Val Asn Tyr Ile
                245                 250                 255

Thr Lys Leu Lys Gly Pro Lys Ala Ala Ala Leu Phe Ala Lys Thr His
            260                 265                 270

Asn Leu Asn Met Leu Gln Asp Ile Pro Met Asp Arg Phe Val Met Asp
    275                 280                 285

Leu Lys Arg Asp Val Lys Val Thr Pro Gly Thr Lys His Thr Glu Glu
290                 295                 300

Arg Pro Lys Val Gln Val Ile Gln Ala Ala Asp Pro Leu Ala Thr Ala
305                 310                 315                 320

Tyr Leu Cys Gly Ile His Arg Glu Leu Val Arg Arg Leu Asn Ala Val
                325                 330                 335

Leu Leu Pro Asn Ile His Thr Leu Phe Asp Met Ser Ala Glu Asp Phe
            340                 345                 350

Asp Ala Ile Ile Ala Glu His Phe Gln Pro Gly Asp Cys Val Leu Glu
            355                 360                 365

Thr Asp Ile Ala Ser Phe Asp Lys Ser Glu Asp Ala Met Ala Leu
    370                 375                 380

Thr Ala Leu Met Ile Leu Glu Asp Leu Gly Val Asp Ala Glu Leu Leu
385                 390                 395                 400

Thr Leu Ile Glu Ala Ala Phe Gly Glu Ile Ser Ser Ile His Leu Pro
            405                 410                 415

Thr Lys Thr Lys Phe Lys Phe Gly Ala Met Met Lys Ser Gly Met Phe
            420                 425                 430

Leu Thr Leu Phe Val Asn Thr Val Ile Asn Ile Val Ile Ala Ser Arg
            435                 440                 445

Val Leu Arg Glu Arg Leu Thr Gly Ser Pro Cys Ala Ala Phe Ile Gly
```

```
                450             455             460
Asp Asp Asn Ile Val Lys Gly Val Lys Ser Asp Lys Leu Met Ala Asp
465                 470                 475                 480

Arg Cys Ala Thr Trp Leu Asn Met Glu Val Lys Ile Ile Asp Ala Val
                485                 490                 495

Val Gly Glu Lys Ala Pro Tyr Phe Cys Gly Gly Phe Ile Leu Cys Asp
            500                 505                 510

Ser Val Thr Gly Thr Ala Cys Arg Val Ala Asp Pro Leu Lys Arg Leu
        515                 520                 525

Phe Lys Leu Gly Lys Pro Leu Ala Ala Asp Asp Glu His Asp Asp Asp
    530                 535                 540

Arg Arg Arg Ala Leu His Glu Glu Ser Thr Arg Trp Asn Arg Val Gly
545                 550                 555                 560

Ile Leu Ser Glu Leu Cys Lys Ala Val Glu Ser Arg Tyr Glu Thr Val
                565                 570                 575

Gly Thr Ser Ile Ile Val Met Ala Met Thr Thr Leu Ala Ser Ser Val
            580                 585                 590

Lys Ser Phe Ser Tyr Leu Arg Gly Ala Pro Ile Thr Leu Tyr
        595                 600                 605

<210> SEQ ID NO 10
<211> LENGTH: 7518
<212> TYPE: DNA
<213> ORGANISM: Artificial Sequence
<220> FEATURE:
<223> OTHER INFORMATION: codon optimized sequence

<400> SEQUENCE: 10
ttgaagagga ttcaccattt ctgcgggctc tccagcgctc ctttcctcag ttcgaagttg      60
aggctaaaca ggtgactgac aatgatcacg ccaacgcaag agcattcagc catctcgcct     120
caaagctcat tgagacagaa gtcgatccct ctgacaccat cctggatatc ggtagcgccc     180
cggcgaggcg catgtacagc aaacacaaat accactgcat atgccctatg cgctgcgcag     240
aggacccaga taggctatac aaatacgcca cgaaactcaa gaagaattgc aaagagatca     300
ccgacaaaga gctcgataaa aagatgaaag aacttgcggc tgtgatgtcc gatcccgatc     360
ttgagacaga gacgatgtgc ttgcacgatg atgagagttg ccgctatgag gccaggtgg      420 cggtgtacca ggacgtctat gcagtagatg gccaacttc tctttaccat caagctaaca     480
aaggtgtgcg ggtcgcttat tggatcgggt ttgatactac accattcatg ttcaagaatc     540
tggcaggggc ctacccaagc tacagcacaa attgggcaga cgagacggtg ttaacggcac     600
ggaatatcgg gctgtgttca tctgacgtaa tggaacgaag cagacgagga atgagtatct     660
tgcgcaaaaa atacctcaag ccctcaaata atgtgctgtt ttctgtgggg tcaaccatct     720
atcatgagaa gagagacctg ctccggagtt ggcacctgcc cagcgtcttt cacctgcgcg     780
gcaagcagaa ttatacgtgt aggtgcgaaa ccatcgtctc ttgtgacgga tacgtggtga     840
agcggattgc catctccccc gggctgtacg ggaagccgag cgggtatgct gcgacaatgc     900
atcgggaggg attcctttgc tgtaaggtca ccgatacgtt gaatggtgag agggtgtcct     960
ttcctgtatg cacatatgtc cccgcaaccc tctgcgatca gatgaccggt atcctggcca    1020
ccgacgtgtc cgccgatgac gcccaaaagc tgctcgtggg ccttaatcag aggatcgtgg    1080
taaacgggag aacccaaaga aacacaaata ctatgaaaaa ctatctgctt ccagtcgtcg    1140
cccaagcctt cgcaagatgg gctaaggaat acaaagagga ccaggaagat gagcgacctc    1200
```

```
tcggtctcag ggatcgacag ttggttatgg gctgctgggc cttcaggcgc cacaaaatca    1260
caagtatcta caaaaggcct gacacgcaaa caataataaa agtgaattcc gactttcact    1320
cttttgttct gccaagaata ggtagcaaca ctctggaaat cgggctcagg accagaatac    1380 gaaaatgct cgaagaacac aaggaaccct ctcctttgat cacggcagag gacgtgcagg    1440
aagcaaaatg cgccgcagac gaagctaaag aagtccggga ggcggaagaa ctgcgagcgg    1500
ctctgccacc cctggcggct gacgtcgagg aacccaccct ggaggcagat gtggatctga    1560
tgcttcagga agcgggagcc gggtccgtgg agacccccag agggttgatc aaagtgacat    1620
cctatgcagg agaagacaaa atcgggagct atgccgtttt gtccccacag gctgtgctta    1680
aatctgagaa actctcctgc atacatcccc tcgccgaaca ggtcattgtg atcacacata    1740
gcggacggaa gggcaggtat gctgtggaac cctatcacgg caaagtagtc gtgcccgagg    1800
gacacgccat tccggtgcaa gatttccagg cactcagcga atccgccaca atcgtataca    1860
atgaacgcga gtttgtgaac aggtacctcc atcacatagc cacacatggg ggggcgctta    1920
atacagacga ggagtactat aagacagtga aacctagtga gcatgacggg gagtacttgt    1980
acgatataga tagaaagcaa tgcgtgaaga aggagctcgt gaccggggttg gggctgacag    2040 gggaactggt cgacccacca ttccacgagt ttgcgtatga atctcttagg accagaccag    2100
cagccccata ccaggtacct actattggcg tttacggggt acccggaagt ggcaaatctg    2160
ggattataaa atctgcagtg actaagaaag accttgttgt ttccgctaag aaggaaaact    2220
gtgccgagat cattcgagac gtgaaaaaaa tgaagggcct ggatgttaat gccagaaccg    2280
tcgattccgt cctgctgaat ggctgcaagc acccagtgga aacgctttac atcgatgagg    2340
catttgcatg tcacgccggg acactgaggg cactcattgc cattattaga ccaaagaagg    2400
cagtgctgtg tggtgacccc aagcaatgcg gcttttttcaa tatgatgtgt ctaaaggtcc    2460
actttaatca tgaaatatgt acgcaggttt tccacaaaag tatctcaaga cggtgcacaa    2520
agtctgttac gtctgtcgtc agtacccctct tctatgataa aagatgagg acgactaacc    2580 ccaaagaaac caagatcgtg attgacacca ctgggagtac aaaacctaaa caggatgacc    2640
tgattctgac ctgctttagg ggctgggtta agcaacttca gatcgattat aaaggaaacg    2700
agattatgac tgccgctgcc agccagggcc tgacacggaa aggtgtgtac gctgtgcgat    2760
acaaagtgaa cgagaacccc ctctatgccc tacgtctga gcacgtcaat gtgctgttga    2820
caaggactga ggatcgaatc gtgtggaaga cattggccgg ggatccctgg attaagactc    2880
tcaccgctaa gtatccaggc aactttactg caaccatcga ggagtggcag gccgagcacg    2940
atgctattat gcgacacatt cttgagcgcc ccgaccctac ggatgtgttt caaaacaagg    3000
ccaatgtctg ctgggcgaag gcactggtgc ctgtcctgaa gactgccggc attgacatga    3060
ccaccgagca gtggaatacg gttgactact ttgagactga taaggcccac agtgcagaga    3120
ttgttttgaa tcagctgtgt gtgagattct cggactgga tctggatagt ggcctgttt    3180 ctgcacctac cgttccgctg tccatcagaa acaatcattg gacaacagt ccatccccca    3240 atatgtatgg tctgaataag gaggtggtgc ggcagctgtc ccggcggtat ccacagctgc    3300
ctcgcgctgt cgccaccggc cgcgtctacg acatgaacac aggaacccct cgaaattatg    3360
accctagaat taacttggtg cctgtgaatc ggcggctgcc tcatgccctc gtgctgcatc    3420
acaacgagca tcctcagagc gatttctcat cttttcgtatc aaagctgaag gccggactg    3480 ttctcgtagt gggcgagaaa ctgtcagttc ctggaaagat ggtggactgg ctcagtgatc    3540
ggcctgaggc gacttttcgg gcgcgtctgg acctgggaat ccctggcgat gtgcctaagt    3600
```

```
acgatatcat ctttgtcaat gttaggaccc cttataaata ccaccattac cagcagtgcg   3660
aagatcacgc tatcaagttg tctatgctta caaagaaggc atgcctccac ttgaacccag   3720
gtggcacatg tgtcagtatc gggtacggct atgctgaccg cgcttctgaa tcaattattg   3780
gtgccatcgc taggcagttc aaattcagta gagtgtgcaa gccaaagagc tcattggagg   3840
aaaccgaggt tctgtttgtg ttcataggat atgaccgaaa agcgcgaacc cataacccat   3900
ataagctgtc atccacactg accaatattt acacgggaag ccgccttcat gaggctgggt   3960
gtgctcccag ttatcacgtg gtgaggggag atattgcaac tgcaactgag ggggtcatta   4020
taaacgccgc caactccaag ggccaaccgg gcggtggagt gtgcggtgca ctctacaaaa   4080
agtttccaga gagtttcgac cttcagccta ttgaggtagg caaagcccgc ctggtgaaag   4140
gcgctgcaaa gcacataatc catgcagtgg gaccgaactt caacaaggtt agcgaggtgg   4200
agggtgataa acagctcgcc gaggcgtatg aatccattgc caagatagtt aatgacaata   4260
actataaatc cgtagctata cctttgctct ctacgggtat attcagcggt aataaagatc   4320
gcctgaccca agcctgaac catctgctta ccgctctgga cacaaccgat gcagatgtgg   4380
ccatttattg ccgcgacaaa aagtgggaga tgacactgaa ggaggccgtt gccagacggg   4440
aggccgtaga ggagatctgt atcagtgatg acagttctgt gaccgagcca gacgctgaac   4500
tagttcgagt tcaccctaaa tctagtctgg ccggaagaaa gggctactct accagcgacg   4560
gaaagacctt ttcttacctg gagggaacaa agttccacca ggcggcgaag gacatcgccg   4620
agatcaacgc aatgtggcct gtggctactg aagcaaacga acaagtctgt atgtatatat   4680
tgggcgaatc tatgagctcc atcaggagta agtgtcccgt ggaagagagc gaggcctcat   4740
caccgccaag cactctgccc tgcctgtgta tccatgctat gacccctgag agagtccaga   4800
gactcaaggc ctctcgcccc gaacagatca cggtgtgcag ctcctttccc ctgccaaaat   4860
acagaatcac cggagtccag aagatacaat gttcccagcc gatccttttt agcccgaagg   4920
tgcccgccta catccatccc aggaaatacc ttgtggagac tccgccagtt gatgaaacac   4980
ccgagccctc tgccgaaaac caaagcacag agggcacccc cgagcagcct cctctcatta   5040
ccgaggacga aacacggact cgaacccccg aaccgattat cattgaggaa gaggaagagg   5100
acagcatctc tcttctctcc gatggcccca cccaccaagt tttgcaggtc gaagcggata   5160
tccacggccc cccttccgtc tcaagtagca gctggagtat cccacacgcc agcgactttg   5220
acgtggacag cctgtctatt ctggacaccc ttgagggtgc ctccgtaacc tctggcgcca   5280
ccagtgccga gaccaacagc tatttcgcca aatcaatgga atttctggca aggccagtgc   5340
ctgctccccg gaccgtcttc agaaaccctc cgcatcccgc acctcggacc cgcacaccaa   5400
gcttggcacc atcccgggcc tgttctcgcg gaataactgg cgagacagtc ggttacgccg   5460
taactcacaa ttccgaaggg ttttgctttt gcaaggtgac cgacactgtg aagggcgaga   5520
gagtgtcatt tcccgtgtgt acttatatcc cagccaccat taactccaga accagcctgg   5580
tctccaaccc gccaggcgta ataggggtga ttacaagaga ggagtttgag gcgttcgtag   5640
cacaacaaca atgacggttt gatgcgggtg catacatctt ttcctccgac accggtcaag   5700
ggcatttaca acaaaaatca gtaaggcaaa cggtcctgtc cgaggttgta ctggagagga   5760
cagaactcga aatctcatac gcacccaggc tggaccagga aaggaagaa ctcttgcgaa   5820 aaaagctcca gctcaaccca actcctgcca atagagtcg ctatcaaagt cgaaaagttg   5880
aaaatatgaa ggctattaca gctcgacgaa ttttgcaagg cctcgggcac tacctcaagg   5940
```

```
ccgagggcaa ggttgaatgt tatagaacac ttcacccagt cccactctat agcagctctg    6000
taaaccgggc tttttccagc cctaaagtgg cagtcgaggc ttgcaatgcg atgctgaagg    6060
agaatttccc tactgtggcg tcatactgca ttataccgga gtatgatgct tacttggaca    6120
tggtggacgg cgcaagttgc tgcctcgaca ctgctagttt ctgtcccgcc aagctccgct    6180
cattccctaa aaagcatagt tacttagagc caactattag gtctgcggta ccttctgcta    6240
ttcagaacac actgcagaat gtgttggcgg cggctaccaa gagaaactgc aatgtgacac    6300
agatgaggga acttcctgtt ctcgactccg cagccttcaa cgttgagtgt ttcaagaagt    6360
acgcctgcaa taacgaatac tgggagactt caaggagaa tcccatccgc ctgacagaag    6420
agaacgttgt gaattacatc actaaactga agggccccaa agccgccgca ttgttcgcta    6480
aaactcacaa ccttaacatg ctgcaagata ttcccatgga tcggttcgtg atggatctca    6540
aacgagacgt caaggttaca cctggcacca acatacgga ggaacgcccg aaggtacagg    6600
tcattcaggc agccgacccc cttgccaccg cttatctctg cgggattcac agagagctgg    6660
ttagacgact caacgcagtt cttctgccga atatacacac tctcttcgac atgtcagccg    6720
aggatttcga tgccatcatc gccgagcact tcaaccagg agattgtgtc ctggagacgg    6780
atatagcatc atttgataag agtgaggacg atgcgatggc ccttaccgcc ttatgatac    6840
tggaagacct gggtgtcgat gccgagcttc tgactctcat cgaggctgcc ttcggagaaa    6900
tcagctccat ccacctgccc acgaagacaa agttcaagtt tggtgcgatg atgaagtccg    6960
gaatgtttct gacgctgttc gttaatacag taatcaatat agttatagct tcacgggtcc    7020
tgcgcgagag actcactgga agtccctgcg ccgctttcat cggggacgat aacattgtta    7080
agggtgttaa gtcagataaa cttatggcgg accgctgtgc tacatggctg aacatggagg    7140
tgaaaataat tgacgcagtc gtcggcgaga aggcaccgta cttctgtggt ggatttatcc    7200
tctgcgattc cgtcacaggc acggcatgcc gggtcgccga tccctcaag aggctgttca    7260
agctgggcaa gcctctcgct gcagatgatg aacacgacga cgaccggcgg cgcgcactgc    7320
acgaggaatc aactaggtgg aacagagtgg gaatcctgtc tgaactgtgc aaggctgtcg    7380
aatccagata cgaaactgtg gggacatcca tcatccatcc atcatcgtca tgcaatgac    7440
caccttggcc agctcagtca aatcttttc ttatctgcgc ggcgctccca ttactttgta    7500
cggatgacac gtgccagc                                                  7518
```

<210> SEQ ID NO 11
<211> LENGTH: 15
<212> TYPE: PRT
<213> ORGANISM: Sindbis virus

<400> SEQUENCE: 11

Lys Gly Lys Thr Ile Lys Thr Thr Pro Glu Gly Thr Glu Glu Trp
1               5                   10                  15

<210> SEQ ID NO 12
<211> LENGTH: 18
<212> TYPE: PRT
<213> ORGANISM: Sindbis virus

<400> SEQUENCE: 12

Met Ser Ala Ala Pro Leu Val Thr Ala Met Cys Leu Leu Gly Asn Val
1               5                   10                  15

Ser Phe

-continued

<210> SEQ ID NO 13
<211> LENGTH: 32
<212> TYPE: PRT
<213> ORGANISM: Sindbis virus

<400> SEQUENCE: 13

```
Lys Gly Lys Thr Ile Lys Thr Thr Pro Glu Gly Thr Glu Glu Trp Ser
 1               5                  10                  15

Ala Ala Pro Leu Val Thr Ala Met Cys Leu Leu Gly Asn Val Ser Phe
            20                  25                  30
```

<210> SEQ ID NO 14
<211> LENGTH: 111
<212> TYPE: PRT
<213> ORGANISM: Semliki Forest virus

<400> SEQUENCE: 14

```
His Ala Gly Ala Gly Val Val Glu Thr Pro Arg Ser Ala Ile Lys Val
 1               5                  10                  15

Thr Ala Gln Pro Asn Asp Val Leu Leu Gly Asn Tyr Val Val Ile Ser
            20                  25                  30

Pro Gln Thr Val Leu Lys Ser Ser Lys Leu Ala Pro Val His Glu Leu
        35                  40                  45

Ala Glu Gln Val Lys Ile Ile Thr His Asn Gly Arg Ala Gly Gly Tyr
    50                  55                  60

Gln Val Asp Gly Tyr Asp Gly Arg Val Ile Ile Phe Cys Gly Ser Ala
65                  70                  75                  80

Ile Pro Val Pro Glu Phe Gln Ala Leu Ser Glu Ser Ala Thr Met Val
                85                  90                  95

Tyr Asn Glu Arg Glu Phe Val Asn Arg Lys Leu Tyr His Ile Ala
            100                 105                 110
```

<210> SEQ ID NO 15
<211> LENGTH: 111
<212> TYPE: PRT
<213> ORGANISM: Artificial Sequence
<220> FEATURE:
<223> OTHER INFORMATION: chimeric nsp2

<400> SEQUENCE: 15

```
Glu Ala Gly Ala Gly Ser Val Glu Thr Pro Arg Gly Leu Ile Lys Val
 1               5                  10                  15

Thr Ser Tyr Ala Gly Glu Asp Lys Ile Gly Ser Tyr Ala Val Ile Ser
            20                  25                  30

Pro Gln Ala Val Leu Lys Ser Glu Lys Leu Ser Cys Ile His Pro Ile
        35                  40                  45

Ala Glu Gln Val Ile Val Ile Thr His Ser Gly Arg Lys Gly Arg Tyr
    50                  55                  60

Ala Val Glu Pro Tyr His Gly Lys Val Val Val Pro Glu Gly His Ala
65                  70                  75                  80

Ile Pro Val Gln Asp Phe Gln Ala Leu Ser Glu Ser Ala Thr Ile Val
                85                  90                  95

Tyr Asn Glu Arg Phe Phe Val Asn Arg Tyr Leu His His Ile Ala
            100                 105                 110
```

<210> SEQ ID NO 16
<211> LENGTH: 111
<212> TYPE: PRT
<213> ORGANISM: Sindbis virus

<400> SEQUENCE: 16

Asp Ile Gly Ala Ala Leu Val Glu Thr Pro Arg Gly His Val Arg Ile
1               5                   10                  15

Ile Pro Gln Ala Asn Asp Arg Met Ile Gly Gln Tyr Ile Val Val Ser
            20                  25                  30

Pro Asn Ser Val Leu Lys Asn Ala Lys Leu Ala Pro Ala His Pro Leu
        35                  40                  45

Ala Asp Gln Val Lys Ile Ile Thr His Ser Gly Arg Ser Gly Arg Tyr
50                  55                  60

Ala Val Glu Pro Tyr Asp Ala Lys Val Leu Met Pro Ala Gly Gly Ala
65                  70                  75                  80

Val Pro Trp Pro Glu Phe Leu Ala Leu Ser Glu Ser Ala Thr Leu Val
                85                  90                  95

Tyr Asn Asn Glu Arg Phe Val Asn Arg Lys Leu Tyr His Ile Ala
            100                 105                 110

<210> SEQ ID NO 17
<211> LENGTH: 111
<212> TYPE: PRT
<213> ORGANISM: Eastern equine encephalitis virus

<400> SEQUENCE: 17

Glu Ala Gly Ala Gly Ser Val Glu Thr Pro Arg Arg His Ile Lys Val
1               5                   10                  15

Thr Thr Tyr Pro Gly Glu Glu Met Ile Gly Ser Tyr Ala Val Ile Ser
            20                  25                  30

Pro Gln Ala Val Leu Asn Ser Glu Lys Leu Ala Cys Ile His Pro Ile
        35                  40                  45

Ala Glu Gln Val Leu Val Met Thr His Lys Gly Arg Ala Gly Arg Tyr
50                  55                  60

Lys Val Glu Pro Tyr His Asp Arg Val Ile Val Pro Ser Gly Thr Ala
65                  70                  75                  80

Ile Pro Ile Pro Asp Phe Gln Ala Leu Ser Glu Ser Ala Thr Ile Val
                85                  90                  95

Phe Asn Glu Arg Phe Phe Val Asn Arg Tyr Leu His His Ile Ala
            100                 105                 110

<210> SEQ ID NO 18
<211> LENGTH: 111
<212> TYPE: PRT
<213> ORGANISM: Artificial Sequence
<220> FEATURE:
<223> OTHER INFORMATION: consensus sequence

<400> SEQUENCE: 18

Glu Ala Gly Ala Gly Ser Val Glu Thr Pro Arg Gly His Ile Lys Val
1               5                   10                  15

Thr Ser Tyr Pro Asn Asp Met Ile Gly Ser Tyr Ala Val Ile Ser
            20                  25                  30

Pro Gln Ala Val Leu Lys Ser Glu Lys Leu Ala Pro Ile His Phe Leu
        35                  40                  45

Ala Glu Gln Val Lys Ile Ile Thr His Ser Gly Arg Ala Gly Arg Tyr
50                  55                  60

Ala Val Glu Pro Tyr His Gly Lys Val Leu Val Phe Ala Gly Ser Ala
65                  70                  75                  80

Ile Pro Val Pro Asp Phe Gln Ala Leu Ser Glu Ser Ala Thr Ile Val
                85                  90                  95

-continued

```
Tyr Asn Glu Arg Glu Phe Val Asn Arg Tyr Leu His His Ile Ala
            100                 105                 110
```

<210> SEQ ID NO 19
<211> LENGTH: 7507
<212> TYPE: DNA
<213> ORGANISM: Venezuelan encephalitis virus

<400> SEQUENCE: 19

```
tcgaggaaga cagcccattc ctcagagctt tgcagcggag cttcccgcag tttgaggtag     60
aagccaagca ggtcactgat aatgaccatg ctaatgccag agcgttttcg catctggctt    120
caaaactgat cgaaacggag gtggacccat ccgacacgat ccttgacatt ggaagtgcgc    180
ccgcccgcag aatgtattct aagcacaagt atcattgtat ctgtccgatg agatgtgcgg    240
aagatccgga cagattgtat aagtatgcaa ctaagctgaa gaaaaactgt aaggaaataa    300
ctgataagga attggacaag aaaatgaagg agctcgccgc cgtcatgagc gaccctgacc    360
tggaaactga gactatgtgc ctccacgacg acgagtcgtg tcgctacgaa gggcaagtcg    420
ctgtttacca ggatgtatac gcggttgacg gaccgacaag tctctatcac caagccaata    480
agggagttag agtcgcctac tggataggct ttgacaccac cccttttatg tttaagaact    540
tggctggagc atatccatca tactctacca actgggccga cgaaaccgtg ttaacggctc    600
gtaacatagg cctatgcagc tctgacgtta tggagcggtc acgtagaggg atgtccattc    660
ttagaaagaa gtatttgaaa ccatccaaca atgttctatt ctctgttggc tcgaccatct    720
accacgagaa gagggactta ctgaggagct ggcacctgcc gtctgtattt cacttacgtg    780
gcaagcaaaa ttacacatgt cggtgtgaga ctatagttag ttgcgacggg tacgtcgtta    840
aaagaatagc tatcagtcca ggcctgtatg ggaagccttc aggctatgct gctacgatgc    900
accgcgaggg attcttgtgc tgcaaagtga cagacacatt gaacggggag agggtctctt    960
ttcccgtgtg cacgtatgtg ccagctacat tgtgtgacca aatgactggc atactggcaa   1020
cagatgtcag tgcggacgac gcgcaaaaac tgctggttgg gctcaaccag cgtatagtcg   1080
tcaacggtcg cacccagaga aacaccaata ccatgaaaaa ttaccttttg cccgtagtgg   1140
cccaggcatt tgctaggtgg gcaaaggaat ataaggaaga tcaagaagat gaaaggccac   1200
taggactacg agatagacag ttagtcatgg ggtgttgggc ttttagaagg cacaagataa   1260
catctattta taagcgcccg gatacccaaa ccatcatcaa agtgaacagc gatttccact   1320
cattcgtgct gcccaggata ggcagtaaca cattggagat cgggctgaga acaagaatca   1380
ggaaaatgtt agaggagcac aaggagccgt cacctctcat taccgccgag gacgtacaag   1440
aagctaagtg cgcagccgat gaggctaagg aggtgcgtga agccgaggag ttgcgcgcag   1500
ctctaccacc tttggcagct gatgttgagg agcccactct ggaagccgat gtcgacttga   1560
tgttacaaga ggctggggcc ggctcagtgg agacacctcg tggcttgata aaggttacca   1620
gctacgctgg cgaggacaag atcggctctt acgctgtgct ttctccgcag gctgtactca   1680
agagtgaaaa attatcttgc atccaccctc tcgctgaaca agtcatagtg ataacacact   1740
ctggccgaaa agggcgttat gccgtggaac cataccatgg taaagtagtg gtgccagagg   1800
gacatgcaat acccgtccag gactttcaag ctctgagtga aagtgccacc attgtgtaca   1860
acgaacgtga gttcgtaaac aggtacctgc accatattgc cacacatgga ggagcgctga   1920
acactgatga agaatattac aaaactgtca agcccagcga gcacgacggc gaatacctgt   1980
acgacatcga caggaaacag tgcgtcaaga aagaactagt cactgggcta gggctcacag   2040
```

```
gcgagctggt ggatcctccc ttccatgaat tcgcctacga gagtctgaga acacgaccag    2100
ccgctcctta ccaagtacca accataggg tgtatggcgt gccaggatca ggcaagtctg     2160
gcatcattaa aagcgcagtc accaaaaaag atctagtggt gagcgccaag aaagaaaact    2220
gtgcagaaat tataagggac gtcaagaaaa tgaaagggct ggacgtcaat gccagaactg    2280
tggactcagt gctcttgaat ggatgcaaac accccgtaga gaccctgtat attgacgaag    2340
cttttgcttg tcatgcaggt actctcgagg cgctcatagc cattataaga cctaaaaagg    2400
cagtgctctg cggggatccc aaacagtgcg gttttttaa catgatgtgc ctgaaagtgc      2460
attttaacca cgagatttgc acacaagtct tccacaaaag catctctcgc cgttgcacta    2520
aatctgtgac ttcggtcgtc tcaaccttgt tttacgacaa aaaaatgaga acgacgaatc    2580
cgaaagagac taagattgtg attgacacta ccggcagtac caaacctaag caggacgatc    2640
tcattctcac ttgtttcaga gggtgggtga agcagttgca aatagattac aaaggcaacg    2700
aaataatgac ggcagctgcc tctcaagggc tgacccgtaa aggtgtgtat gccgttcggt    2760
acaaggtgaa tgaaaatcct ctgtacgcac ccacctcaga acatgtgaac gtcctactga    2820
cccgcacgga ggaccgcatc gtgtggaaaa cactagccgg cgacccatgg ataaaaacac    2880
tgactgccaa gtaccctggg aatttcactg ccacgataga ggagtggcaa gcagagcatg    2940
atgccatcat gaggcacatc ttggagagac cggaccctac cgacgtcttc cagaataagg    3000
caaacgtgtg ttgggccaag gctttagtgc cggtgctgaa gaccgctggc atagacatga    3060
ccactgaaca atggaacact gtggattatt ttgaaacgga caaagctcac tcagcagaga    3120
tagtattgaa ccaactatgc gtgaggttct ttggactcga tctggactcc ggtctatttt    3180
ctgcacccac tgttccgtta tccattagga ataatcactg gataactcc ccgtcgccta    3240 acatgtacgg gctgaataaa gaagtggtcc gtcagctctc tcgcaggtac ccacaactgc    3300
ctcgggcagt tgccactgga agagtctatg acatgaacac tggtacactg cgcaattatg    3360
atccgcgcat aaacctagta cctgtaaaca gaagactgcc tcatgcttta gtcctccacc    3420
ataatgaaca cccacagagt gacttttctt cattcgtcag caaattgaag gcagaactg    3480 tcctggtggt cggggaaaag ttgtccgtcc caggcaaaat ggttgactgg ttgtcagacc    3540
ggcctgaggc taccttcaga gctcggctgg atttaggcat cccaggtgat gtgcccaaat    3600
atgacataat atttgttaat gtgaggaccc catataaata ccatcactat cagcagtgtg    3660
aagaccatgc cattaagctt agcatgttga ccaagaaagc ttgtctgcat ctgaatcccg    3720
gcggaacctg tgtcagcata ggttatggtt acgctgacag ggccagcgaa agcatcattg    3780
gtgctatagc gcggcagttc aagttttccc gggtatgcaa accgaaatcc tcacttgaag    3840
agacggaagt tctgtttgta ttcattgggt acgatcgcaa ggcccgtacg cacaatcctt    3900
acaagctttc atcaaccttg accaacattt atacaggttc cagactccac gaagccggat    3960
gtgcaccctc atatcatgtg gtgcgagggg atattgccac ggccaccgaa ggagtgatta    4020
taaatgctgc taacagcaaa ggacaacctg gcggaggggt gtgcggagcg ctgtataaga    4080
aattcccgga aagcttcgat ttacagccga tcgaagtagg aaaagcgcga ctggtcaaag    4140
gtgcagctaa acatatcatt catgccgtag gaccaaactt caacaaagtt tcggaggttg    4200
aaggtgacaa acagttggca gaggcttatg agtccatcgc taagattgtc aacgataaca    4260
attacaagtc agtagcgatt ccactgttgt ccaccgcgcat cttttccggg aacaaagatc    4320
gactaaccca atcattgaac catttgctga cagctttaga caccactgat gcagatgtag    4380
```

```
ccatatactg cagggacaag aaatgggaaa tgactctcaa ggaagcagtg gctaggagag    4440
aagcagtgga ggagatatgc atatccgacg actcttcagt gacagaacct gatgcagagc    4500
tggtgagggt gcatccgaag agttctttgg ctggaaggaa gggctacagc acaagcgatg    4560
gcaaaacttt ctcatatttg gaagggacca agtttcacca ggcggccaag gatatagcag    4620
aaattaatgc catgtggccc gttgcaacgg aggccaatga gcaggtatgc atgtatatcc    4680
tcggagaaag catgagcagt attaggtcga aatgccccgt cgaagagtcg gaagcctcct    4740
caccacctag cacgctgcct tgcttgtgca tccatgccat gactccagaa agagtacagc    4800
gcctaaaagc ctcacgtcca gaacaaatta ctgtgtgctc atcctttcca ttgccgaagt    4860
atagaatcac tggtgtgcag aagatccaat gctcccagcc tatattgttc tcaccgaaag    4920
tgcctgcgta tattcatcca aggaagtatc tcgtggaaac accaccggta gacgagactc    4980
cggagccatc ggcagagaac caatccacag agggacacc tgaacaacca ccacttataa    5040
ccgaggatga gaccaggact agaacgcctg agccgatcat catcgaagag aagaagagg    5100
atagcataag tttgctgtca gatggcccga cccaccaggt gctgcaagtc gaggcagaca    5160
ttcacgggcc gccctctgta tctagctcat cctggtccat tcctcatgca tccgactttg    5220
atgtggacag tttatccata cttgacaccc tggagggagc tagcgtgacc agcggggcaa    5280
cgtcagccga gactaactct tacttcgcaa agagtatgga gtttctggcg cgaccggtgc    5340
ctgcgcctcg aacagtattc aggaaccctc cacatcccgc tccgcgcaca agaacaccgt    5400
cacttgcacc cagcagggcc tgctcgagag ggatcacggg agaaaccgtg ggatacgcgg    5460
ttacacacaa tagcgagggc ttcttgctat gcaaagttac tgacacagta aaaggagaac    5520
gggtatcgtt ccctgtgtgc acgtacatcc cggccaccat aaactcgaga accagcctgg    5580
tctccaaccc gccaggcgta aatagggtga ttacaagaga ggagtttgag gcgttcgtag    5640
cacaacaaca atgacggttt gatgcgggtg catacatctt ttcctccgac accggtcaag    5700
ggcatttaca acaaaaatca gtaaggcaaa cggtgctatc cgaagtggtg ttggagagga    5760
ccgaattgga gatttcgtat gccccgcgcc tcgaccaaga aaaagaagaa ttactacgca    5820
agaaattaca gttaaatccc acacctgcta acagaagcag ataccagtcc aggaaggtgg    5880
agaacatgaa agccataaca gctagacgta ttctgcaagg cctagggcat tatttgaagg    5940
cagaaggaaa agtggagtgc taccgaaccc tgcatcctgt tcctttgtat tcatctagtg    6000
tgaaccgtgc cttttcaagc cccaaggtcg cagtggaagc ctgtaacgcc atgttgaaag    6060
agaactttcc gactgtggct tcttactgta ttattccaga gtacgatgcc tatttggaca    6120
tggttgacgg agcttcatgc tgcttagaca ctgccagttt ttgccctgca aagctgcgca    6180
gctttccaaa gaaacactcc tatttggaac ccacaatacg atcggcagtg ccttcagcga    6240
tccagaacac gctccagaac gtcctggcag ctgccacaaa aagaaattgc aatgtcacgc    6300
aaatgagaga attgcccgta ttggattcgg cggcctttaa tgtggaatgc ttcaagaaat    6360
atgcgtgtaa taatgaatat tgggaaacgt ttaaagaaaa ccccatcagg cttactgaag    6420
aaaacgtggt aaattacatt accaaattaa aaggaccaaa agctgctgct cttttttgcga    6480
agacacataa tttgaatatg ttgcaggaca taccaatgga caggtttgta atggacttaa    6540
agagagacgt gaaagtgact ccaggaacaa acatactgaa gaacggccc aaggtacagg    6600
tgatccaggc tgccgatccg ctagcaacag cgtatctgtg cggaatccac cgagagctgg    6660
ttaggagatt aaatgcggtc ctgcttccga acattcatac actgtttgat atgtcggctg    6720
aagactttga cgctattata gccgagcact tccagcctgg ggattgtgtt ctggaaactg    6780
```

```
acatcgcgtc gtttgataaa agtgaggacg acgccatggc tctgaccgcg ttaatgattc    6840
tggaagactt aggtgtggac gcagagctgt tgacgctgat tgaggcggct ttcggcgaaa    6900
tttcatcaat acatttgccc actaaaacta aatttaaatt cggagccatg atgaaatctg    6960
gaatgttcct cacactgttt gtgaacacag tcattaacat tgtaatcgca agcagagtgt    7020
tgagagaacg gctaaccgga tcaccatgtg cagcattcat tggagatgac aatatcgtga    7080
aaggagtcaa atcggacaaa ttaatggcag acaggtgcgc cacctggttg aatatggaag    7140
tcaagattat agatgctgtg gtgggcgaga aagcgcctta tttctgtgga gggtttattt    7200
tgtgtgactc cgtgaccggc acagcgtgcc gtgtggcaga ccccctaaaa aggctgttta    7260
agcttggcaa acctctggca gcagacgatg aacatgatga tgacaggaga agggcattgc    7320
atgaagagtc aacacgctgg aaccgagtgg gtattctttc agagctgtgc aaggcagtag    7380
aatcaaggta tgaaaccgta ggaacttcca tcatacttcc atcatagtta tggccatgac    7440
tactctagct agcagtgtta aatcattcag ctacctgaga ggggccccta taactctcta    7500
cggctaa                                                              7507

<210> SEQ ID NO 20
<211> LENGTH: 7506
<212> TYPE: DNA
<213> ORGANISM: Artificial Sequence
<220> FEATURE:
<223> OTHER INFORMATION: consensus sequence
<221> NAME/KEY: misc_feature
<222> LOCATION: (1)...(7506)
<223> OTHER INFORMATION: n = A,T,C or G

<400> SEQUENCE: 20
tnganganga nnnnccattn ctnngngctn tncagcgnnn cttnccncag ttngangtng      60
angcnaanca ggtnactgan aatgancang cnaangcnag agcnttnnnn catctngcnt     120
caaanctnat nganacngan gtngancent cngacacnat cctnganatn ggnagngcnc     180
cngcnngnng natgtannnn aancacaant ancantgnat ntgnccnatg ngntgngcng     240
angaccngna nagnntntan aantangcna cnaanctnaa gaanaantgn aanganatna     300
cnganaanga nnntnganaan aanatgaang anctngcngc ngtnatgnnc ganccnganc     360 tngananga gacnatgtgc ntncacgang angagnnntg ncgctangan ggncangtng     420
cngtntacca ggangtntan gcngtngang gnccacnnn tctntancan caagcnaana     480
anggngtnng ngtcgcntan tggatnggnt ttganacnac nccnttnatg ttnaagaann     540
tggcnggngc ntanccannn tacnnnacna antgggcnga cganacngtg ttaacggcnc     600
gnaanatngg nctntgnnnn tctgacgtna tggancgnnn nngnngaggn atgnnnatnn     660
tnngnaanaa ntannntnaan ccntcnaana atgtnctntt ntctgtnggn tcnaccatct     720
ancangagaa gagngacntn ctnnggagnt ggcacctgcc nnnngtnttt cacntncgng     780
gcaagcanaa ttanacntgt nggtgngana cnnatngtnn nttgnacggg ntacgtngtn     840
aanngnatng cnatcnnncc nggnctgtan gggaagccnn nnggntatgc tgcnacnatg     900
cancgngagg gattcntntg ctgnaangtn acnganacnt tgaangnga gagggtntcn     960 tttccngtnt gcacntatgt nccngcnacn ntntgnganc anatgacngg natnctggcn    1020
acngangtnn nngcnganga cgcncaaaan ctgctngtng gnctaaanca gngatngtn    1080 gtnaacggnn gnacccanag aaaacacnaat acnatgaaaa antanctnnt nccngtngtn    1140
gcccangcnt tngcnagntg ggcnaaggaa tanaangang ancangaaga tgannngnccn    1200
```

```
ctnggnctnn gngatngaca gttngtnatg ggntgntggg cnttnagnng ncacaanatn    1260
acanntatnt anaanngncc nganacncaa acnatnatna aagtgaannn cganttncac    1320
tcnttngtnc tgccnagnat naggnagnaa cacnntggan atcgggctna gnacnagaat    1380
nngnaaaatg ntngangnc acaaggancc ntcncctntn atnacngcng aggacgtnca    1440
ngaagcnaan tgcgcngcng angangctaa ngangtncgn gangcngang anntgcgngc    1500
ngctctncca ccnntggcng ctgangtnga ggancccacn ctggangcng atgtngannt    1560
gatgntncan gangcnggng ccggntcngt ggagacnccn ngnggnttga tnaangtnac    1620
nnnctangcn ggngangaca anatcggnnn tangcgtnn tntcnccnca ggctgtnctn    1680
aannntgana aantntcntg catncanccn ctcgcngaac angtcatngt gatnacacan    1740
nnnggncgna aggnngntat gcngtggaac cntancangg naaagtagtn gtgccngagg    1800
gacangcnat nccngtncan ganttncang cnctnagnga annngccacn atngtntaca    1860
angaacgnga gttngtnaac aggtacctnc ancanatngc cacacatggn ggngcgctna    1920
anacnganga ngantantan aanacngtna anccnagnga gcangacggn gantacntgt    1980
acganatnga nagnaancan tgcgtnaaga anganctngt nacnggntn gggctnacag    2040 gnganctggt ngancncncn ttccangant tngcntanga nnntctnagn acnngaccag    2100
cngcnccnta ccangtaccn acnatnggng tntanggngt nccnggannn ggcaantctg    2160
gnatnatnaa annngcagtn acnaanaaag anctngtngt nnncgcnaag aangaaaact    2220
gtgcnganat natnngngac gtnaanaaaa tgaangngct ggangtnaat gccagaacng    2280
tngantcngt nctnntgaat ggntgcaanc accngtnga nacnctntan atngangang    2340
cntttgcntg ccangcnggn acnctnagng cnctcatngc cattatnaga ccnaanaagg    2400
cagtgctntg nggngancc aancantgcg gnttttnaa natgatgtgn ctnaangtnc    2460
antttaanca nganatntgn acncangtnt tccacaaaag natctcnngn cgntgcacna    2520
antctgtnac ntcngtcgtc nnnaccntnt tntanganaa naanatgagn acgacnaanc    2580
cnaaaganac naagatngtg attgacacna cnggnagtac naaacctaan caggnganc    2640 tnattctnac ntgnttnagn ggntgggtna agcanntnca natngattan aaaggnaacg    2700
anatnatgac ngcngctgcc nnncanggnc ggacncgnaa aggtgtgtan gcngtncgnt    2760
acaangggaa nganaanccn ctntangcnc cnacntcnga ncangtnaan gtnctnntga    2820
cnngnacnga ggancgnatc gtgtggaana cantngccgg ngancntgg atnaanacnc    2880 tnacngcnaa gtanccnggn aanttnactg cnacnatnga ggagtggcan gcngagcang    2940
atgcnatnat gngncacatn ntngagngnc cngaccctac ngangtnttn canaanaagg    3000
cnaangtntg ntgggcnaag gcnntngtgc cngtnctgaa gacngcnggc atngacatga    3060
ccacnganca ntggaanacn gtngantant ttganacnga naangcncac nnngcagaga    3120
tngtnttgaa ncanctntgn gtgagnttct tnggcctnga tctggannnn ggnctntttt    3180
ctgcaccnac ngttccgntn tccatnagna anaatcantg gganaacnnn cctcnccna    3240 anatgtangg nctgaataan gangggntc gncagctntc ncgnnggtan ccacanctgc    3300
ctcgngcngt ngccacnggn ngngtctang acatgaacac nggacncnt cgnaattatg    3360 anccnngnat naacntngtn cctgtnaann gnngnctgcc tcatgcnntn gtnctncanc    3420
anaanganca nccncagagn ganttntcnt cnttcgtnnn naanntgaag ggcngnactg    3480
tnctngtngt nggnganaan ntgtcngtnc cnggnaanat ggtngactgg ntnnnnganc    3540
```

```
ggcctgaggc nacnttnngn gcncgnctgg anntnggnat cccnggngat gtgccnaant    3600
anganatnat ntttgtnaag gtnaggaccc cntataaata ccancantan cagcagtgng    3660
aagancangc natnaagntn nnnatgntna cnaagaangc ntgnctncan ntgaanccng    3720
gnggnacntg tgtcagnatn ggntanggnt angctgacng ngcnnnngaa nnnatnattg    3780
gtgcnatngc nnggcagttc aanttnnnnn gngtntgcaa nccnaannnc tcantngang    3840
anacngangt tctgtttgtn ttcatnggnt angancgnaa ngcncgnacn canaanccnt    3900
anaagctntc atcnacnntg accaanattt anacnggnnn cngnctncan gangcnggnt    3960
gtgcncccnn ntaccangtg gtgngnggng atattgcnac ngcnacngan ggngtnatta    4020
taaangcngc naacnncaan ggcaaccng gcggnggngt gtgcggngcn ctntanaana    4080
anttnccnga nagnttcgan ntncagccna tngangtagg naaagcncgn ctggtnaaag    4140
gngcngcnaa ncanatnatn catgcngtng gaccnaactt caacaangtt nnngaggtng    4200
anggtganaa acagntngcn gaggcntaga ntccatngcn aagatngtna anganaanaa    4260
ntanaantcn gtagcnatnc cnntgntntc nacnggnatn ttnnncggna anaaagatcg    4320
nctnacccaa nnnntgaacc atntgctnac ngctntngac acnacngatg cagatgtngc    4380
catntantgc ngngacaana antgggnanat gacnctnaag gangcngtng cagnngnga    4440
ngcngtngag gagatntgna tnnnnganga cnnttcngtg acngnccng angcngnact    4500
ngtnngngtn canccnaann ntntnnttggc nggaagnaag ggctacnna cnagcgangg    4560
naanacnttn tcntanntgg anggnacnaa gatncaccag gcggcnaagg anatngcnga    4620
natnaangcn atgtggccng tngcnacnga ngcnaangan cangtntgna tgtatatnnt    4680
nggngaannn atgagcnnna tnaggnnnaa ntgncccgtn gaagagnnng angcctcntc    4740
accnccnagc acnctgccnt gcntgtgnat ccatgcnatg acnccngana gagtncagng    4800
nctnaangcc tcncgnccng aacanatnac ngtgtgcnnn tccttccnn tgccnaanta    4860
nagaatcacn gggntcnaga agatncaatg ntcccagccn atnntnttnn nnccgaangt    4920
gccngcntan atncatccna ggaantanct ngtgganacn ccnccngtng anganacncc    4980
ngagccntcn gcnganaacc aanncacaga gggnacnccn gancanccnc cnctnatnac    5040
cgaggangan acnnggactn gaacnccnga nccgatnagc atnnnganga ngangaagag    5100
ganagcatnt ntnctntcng atggcccnac ccaccangtn ntgcangtcg angcnganat    5160
ncacggnccn ccntcngtnt cnagnnnnnn ctggnnnatn ccncangcnn ncgactttga    5220
ngtggacagn ntntcnatnc tngacaccct ngagggngcn nncgtnaccn nnggngcnac    5280
nnnngccgag acnaacnnnt anttcgcnaa nnnnatggan tttctggcnn gnccngtgcc    5340
tgcnccncgn acngtnttca gnaaccctcc ncatcccgcn ccncgnacnn gnacaccnnn    5400
nntngcaccn nncgggcct gntcnngngg natnacnggn ganacngtng gntacgcngt    5460
nacncacaat nncganggnt tnttgctntg caangtnacn gacacngtna angngnanng    5520
ngtntcnttn ccngtgtgna cntanacccc ngccaccatn aactcnagaa ccagcctggt    5580
ctccaacccg ccaggcgtaa ataggtgat tacaagagag gagtttgagg cgttcgtagc    5640
acaacaacaa tgacggtttg atgcgggtgc atacatcttt tcctccgaca ccggtcaagg    5700
gcatttacaa caaaaatcag taaggcaaac ggtnctntcc gangtngtnn tggagaggac    5760
ngaantngan atntcntang cnccnngnct ngaccangan aangaagaan tnntncgnaa    5820
naanntncag ntnaaccna cncctgcnaa nagnagnngn tancannnnn gnaangtnga    5880
naanatgaan gcnatnacag ctngacgnat tntgcaaggc ctgggcant anntnaaggc    5940
```

-continued

```
ngangqnaan  gtngantgnt  anngaacnct  ncanccngtn  ccnntntatn  ncanctnntg   6000
tnaaccgngc  nttttcnagc  ccnaangtng  cagtngangc  ntgnaangcn  atgntgaang   6060
agaanttncc  nactgtggcn  tcntactgna  ttatnccnga  gaangatgcn  tanttggaca   6120
tggtngacgg  ngcnnnntgc  tgcntngaca  ctgcnagttt  ntgnccngcn  aagctncgcn   6180
nnttnccnaa  naancannnn  tanttnganc  cnacnatnng  ntcgcngtn   cctgcngcna   6240 tncagaacac  nctncagaan  gtnntggcng  cngcnacnaa  nagaaantgc  aatgtnacnc   6300
anatgagnga  antnccngtn  ntngantcng  cngccttnaa  ngtngantgn  ttcaagaant   6360
angcntgnaa  gaagaatan   tggganacnt  tnaanganaa  ncccatcngn  ctnacgaag    6420 anaacgtngt  naattacatn  acnaaantna  anggnccnaa  agcngcngcn  ntnttngcna   6480
anacncanaa  nnttaaatg   ntgcangana  tnccnatgga  nnggttngtn  atggannta    6540 angagacgtn  aanngtnacn  ccnggnacna  aacatacnga  ngaacgnccn  aaggtacagg   6600
tnatncaggc  ngccgancon  ctngcnacng  cntatctntg  cggnatncac  ngagagctgg   6660
ttagnngant  naangcngtn  ctnctnccga  anatncanac  nctnttngan  atgtcngcng   6720
anganttnga  ngcnatnatn  gccgagcact  tncanccngg  ngattgtgtn  ctgganacng   6780
anatngcntc  ntttgataan  agtgaggacg  angcnatggc  nctnaccgcn  ntnatgatnc   6840
tggaagacnt  nggtgtngan  gcngagctnn  tgacnctnat  ngaggcngcn  ttcggngaaa   6900
tnnnntcnat  ncanntgccc  acnaaacna   anttnaantt  nggngcnatg  atgaantcng   6960
gaatgttnct  nacnctgttn  gtnaanacag  tnatnaanat  ngtnatngcn  nnngngtnnt   7020
gngnganngn  ctnacnggan  nnccntgngc  ngcnttcatn  ggngangana  anatngtnaa   7080
nggngtnaan  tcnganaaan  tnatggcnga  cngntgngcn  acntggntga  anatggangt   7140
naanatnatn  gangcngtng  tnggcgagaa  ngcnccntan  ttctgtgggng gntttatnnt   7200 ntgngantcc  gtnacnggca  cngcntgccg  ngtngcngan  cccctnaana  ggctgttnaa   7260
gctnggcaan  cccctngcng  cagangatga  acangangan  gacnggngnn  gngcantgca   7320
ngangantca  acnngntgga  acngagtggg  natnctntcn  ganctgtgca  aggcngtnga   7380
aacnagntan  gaaacgtng   gnacntccat  catncntcca  tcatngtnat  ggcnatgacn   7440 acnntgcna   gcnnngtnaa  atcnttnnnn  tanctgngng  gngcnccnat  nactntntac   7500 ggntna                                                                   7506
```

<210> SEQ ID NO 21
<211> LENGTH: 105
<212> TYPE: PRT
<213> ORGANISM: Semliki Forest virus

<400> SEQUENCE: 21

Pro Asn Val Cys Trp Ala Lys Ser Ile Val Pro Val Leu Asp Thr Ala
1               5                   10                  15

Gly Ile Arg Leu Thr Ala Glu Glu Trp Ser Thr Ile Ile Thr Ala Phe
            20                  25                  30

Lys Glu Asp Arg Ala Tyr Ser Pro Val Val Ala Leu Asn Glu Ile Cys
        35                  40                  45

Thr Lys Tyr Tyr Gly Val Asp Ile Asp Ser Gly Ile Phe Ser Ala Pro
    50                  55                  60

Lys Tyr Ser Leu Tyr Tyr Glu Asn Asn His Trp Asp Asn Arg Pro Gly
65                  70                  75                  80

Gly Arg Met Tyr Gly Phe Asn Ala Ala Thr Ala Ala Arg Leu Glu Ala

```
                    85                  90                  95

Arg His Thr Phe Leu Lys Gly Gln Trp
            100                 105

<210> SEQ ID NO 22
<211> LENGTH: 104
<212> TYPE: PRT
<213> ORGANISM: Artificial Sequence
<220> FEATURE:
<223> OTHER INFORMATION: chimeric nsp2

<400> SEQUENCE: 22

Pro Asn Val Cys Trp Ala Lys Ala Leu Val Pro Val Leu Lys Thr Ala
1               5                   10                  15

Gly Ile Asp Met Thr Thr Glu Gln Trp Asn Thr Val Asp Tyr Phe Glu
            20                  25                  30

Thr Asp Lys Ala His Ser Ala Glu Ile Val Leu Asn Gln Leu Cys Val
        35                  40                  45

Arg Phe Phe Gly Leu Asp Leu Asp Ser Gly Leu Phe Ser Ala Pro Thr
    50                  55                  60

Val Pro Leu Ser Ile Arg Asn Asn His Trp Asp Asn Ser Pro Ser Pro
65                  70                  75                  80

Asn Met Tyr Gly Leu Asn Lys Glu Val Val Arg Gln Leu Ser Arg Arg
                85                  90                  95

Tyr Pro Gln Leu Pro Arg Ala Val
            100

<210> SEQ ID NO 23
<211> LENGTH: 112
<212> TYPE: PRT
<213> ORGANISM: Sindbis virus

<400> SEQUENCE: 23

Pro Asn Val Cys Trp Ala Lys Ala Leu Glu Pro Ile Leu Ala Thr Ala
1               5                   10                  15

Gly Ile Val Leu Thr Gly Cys Gln Trp Ser Glu Leu Phe Pro Gln Phe
            20                  25                  30

Ala Asp Asp Lys Pro His Ser Ala Ile Tyr Ala Leu Asp Val Ile Cys
        35                  40                  45

Ile Lys Phe Phe Gly Met Asp Leu Thr Ser Gly Leu Phe Ser Lys Gln
    50                  55                  60

Ser Ile Pro Leu Thr Tyr His Pro Ala Asp Ser Ala Arg Pro Val Ala
65                  70                  75                  80

His Trp Asp Asn Ser Pro Gly Thr Arg Lys Tyr Gly Tyr Asp His Ala
                85                  90                  95

Ile Ala Ala Glu Leu Ser Arg Arg Phe Pro Val Phe Gln Leu Ala Gly
            100                 105                 110

<210> SEQ ID NO 24
<211> LENGTH: 104
<212> TYPE: PRT
<213> ORGANISM: Eastern equine encephalitis virus

<400> SEQUENCE: 24

Pro Asn Val Cys Trp Ala Lys Ala Leu Glu Pro Val Leu Ala Thr Ala
1               5                   10                  15

Asn Ile Thr Leu Thr Arg Ser Gln Trp Glu Thr Ile Pro Ala Phe Lys
            20                  25                  30
```

```
Asp Asp Lys Ala Tyr Ser Pro Glu Met Ala Leu Asn Phe Phe Cys Thr
        35                  40                  45

Arg Phe Phe Gly Val Asp Ile Asp Ser Gly Leu Phe Ser Ala Pro Thr
    50                  55                  60

Val Pro Leu Ser Tyr Thr Asn Glu His Trp Asp Asn Ser Pro Gly Pro
65                  70                  75                  80

Asn Met Tyr Gly Leu Cys Met Arg Asn Ala Lys Glu Ile Ala Arg Arg
                85                  90                  95

Tyr Pro Gln Ile Leu Lys Ala Val
            100

<210> SEQ ID NO 25
<211> LENGTH: 110
<212> TYPE: PRT
<213> ORGANISM: Artificial Sequence
<220> FEATURE:
<223> OTHER INFORMATION: consensus sequence
<221> NAME/KEY: VARIANT
<222> LOCATION: (1)...(110)
<223> OTHER INFORMATION: Xaa = Any Amino Acid
<221> NAME/KEY: VARIANT
<222> LOCATION: (1)...(110)
<223> OTHER INFORMATION: Xaa = Any Amino Acid

<400> SEQUENCE: 25

Pro Asn Val Cys Trp Ala Lys Ala Leu Val Pro Val Leu Ala Thr Ala
 1               5                  10                  15

Gly Ile Xaa Ile Thr Ala Glu Gln Trp Ser Xaa Thr Ile Pro Ala Phe
            20                  25                  30

Lys Asp Asp Lys Ala His Ser Pro Glu Ile Ala Leu Asn Xaa Ile Cys
        35                  40                  45

Thr Lys Phe Phe Gly Val Asp Ile Asp Ser Gly Leu Phe Ser Ala Pro
    50                  55                  60

Thr Val Pro Leu Ser Tyr Xaa Xaa Xaa Xaa Xaa Xaa Asn Asn His Trp
65                  70                  75                  80

Asp Asn Ser Pro Gly Pro Arg Met Tyr Gly Leu Asn Xaa Ala Ile Ala
                85                  90                  95

Ala Glu Ile Ser Arg Arg Tyr Pro Xaa Leu Xaa Lys Ala Val
            100                 105                 110

<210> SEQ ID NO 26
<211> LENGTH: 113
<212> TYPE: PRT
<213> ORGANISM: Semliki Forest virus

<400> SEQUENCE: 26

Pro Ser Val Leu Asp Asn Val Ile Pro Ile Asn Arg Arg Leu Pro His
 1               5                  10                  15

Ala Leu Val Ala Glu Tyr Lys Thr Val Lys Gly Ser Arg Val Glu Trp
            20                  25                  30

Leu Val Asn Lys Val Arg Gly Tyr His Val Leu Leu Val Ser Glu Tyr
        35                  40                  45

Asn Leu Ala Leu Pro Arg Arg Arg Val Thr Trp Leu Ser Pro Leu Asn
    50                  55                  60

Val Val Thr Gly Ala Asp Arg Cys Tyr Asp Leu Ser Leu Gly Leu Pro
65                  70                  75                  80

Ala Asp Ala Gly Arg Phe Asp Leu Val Phe Val Asn Ile His Thr Glu
                85                  90                  95

Phe Arg Ile His His Tyr Gln Gln Cys Val Asp His Ala Met Lys Leu
```

Gln

<210> SEQ ID NO 27
<211> LENGTH: 109
<212> TYPE: PRT
<213> ORGANISM: Artificial Sequence
<220> FEATURE:
<223> OTHER INFORMATION: chimeric nsp2

<400> SEQUENCE: 27

Pro Asp Pro Arg Ile Asn Leu Val Pro Val Asn Arg Arg Leu Pro His
1               5                   10                  15

Ala Leu Val Leu His His Asn Glu His Pro Gln Ser Asp Phe Ser Ser
            20                  25                  30

Phe Val Ser Lys Leu Lys Gly Arg Thr Val Leu Val Val Gly Glu Lys
        35                  40                  45

Leu Ser Val Pro Gly Lys Met Val Asp Trp Leu Ser Asp Arg Pro Glu
    50                  55                  60

Ala Thr Phe Arg Ala Arg Leu Asp Leu Gly Ile Pro Gly Asp Val Pro
65                  70                  75                  80

Lys Tyr Asp Ile Ile Phe Val Asn Val Arg Thr Pro Tyr Lys Tyr His
                85                  90                  95

His Tyr Gln Gln Cys Glu Asp His Ala Ile Lys Leu Ser
            100                 105

<210> SEQ ID NO 28
<211> LENGTH: 111
<212> TYPE: PRT
<213> ORGANISM: Sindbis virus

<400> SEQUENCE: 28

Pro Ser Ala Gln His Asn Leu Val Pro Val Asn Arg Asn Leu Pro His
1               5                   10                  15

Ala Leu Val Pro Glu Tyr Lys Glu Lys Gln Pro Gly Pro Val Lys Lys
            20                  25                  30

Phe Leu Asn Gln Phe Lys His His Ser Val Leu Val Val Ser Glu Glu
        35                  40                  45

Lys Ile Glu Ala Pro Arg Lys Arg Ile Glu Trp Ile Ala Pro Ile Gly
    50                  55                  60

Ile Ala Gly Ala Asp Lys Asn Tyr Asn Leu Ala Phe Gly Phe Pro Pro
65                  70                  75                  80

Gln Ala Arg Tyr Asp Leu Val Phe Ile Asn Ile Gly Thr Lys Tyr Arg
                85                  90                  95

Asn His His Phe Gln Gln Cys Glu Asp His Ala Ala Thr Leu Lys
            100                 105                 110

<210> SEQ ID NO 29
<211> LENGTH: 109
<212> TYPE: PRT
<213> ORGANISM: Eastern equine encephalitis virus

<400> SEQUENCE: 29

Pro Asn Pro Leu Ile Asn Val Val Leu Asn Arg Arg Leu Pro His
1               5                   10                  15

Ser Leu Val Val Thr Gln Arg Tyr Thr Gly Asn Gly Asp Tyr Ser Gln
            20                  25                  30

Leu Val Thr Lys Met Thr Gly Lys Thr Val Leu Val Val Gly Thr Pro

-continued

```
        35                  40                  45

Met Asn Ile Pro Gly Lys Arg Val Glu Thr Leu Gly Gln Ser Pro Gln
    50                  55                  60

Cys Thr Tyr Lys Ala Glu Leu Asp Leu Gly Ile Pro Ala Ala Leu Gly
65                  70                  75                  80

Lys Tyr Asp Ile Ile Phe Ile Asn Val Arg Thr Pro Tyr Arg His His
                85                  90                  95

His Tyr Gln Gln Cys Glu Asp His Ala Ile His His Ser
            100                 105

<210> SEQ ID NO 30
<211> LENGTH: 112
<212> TYPE: PRT
<213> ORGANISM: Artificial Sequence
<220> FEATURE:
<223> OTHER INFORMATION: consensus sequence
<221> NAME/KEY: VARIANT
<222> LOCATION: (1)...(112)
<223> OTHER INFORMATION: Xaa = Any Amino Acid
<221> NAME/KEY: VARIANT
<222> LOCATION: (1)...(112)
<223> OTHER INFORMATION: Xaa = Any Amino Acid

<400> SEQUENCE: 30

Pro Ser Pro Leu Ile Asn Leu Val Pro Val Asn Arg Arg Leu Pro His
 1               5                  10                  15

Ala Leu Val Leu Glu Tyr Lys Glu Xaa Xaa Asn Ser Asp Val Ser Xaa
            20                  25                  30

Leu Val Asn Lys Leu Lys Gly Arg Thr Val Leu Val Val Ser Glu Glu
        35                  40                  45

Lys Leu Ala Ile Pro Arg Lys Arg Val Glu Trp Leu Ser Pro Ile Xaa
    50                  55                  60

Ile Pro Gly Ala Thr Arg Lys Tyr Asp Leu Asp Leu Gly Ile Pro Ala
65                  70                  75                  80

Asp Leu Gly Lys Tyr Asp Ile Ile Phe Ile Asn Ile Arg Thr Pro Tyr
                85                  90                  95

Arg His His His Tyr Gln Gln Cys Glu Asp His Ala Ile Lys Leu Ser
            100                 105                 110

<210> SEQ ID NO 31
<211> LENGTH: 110
<212> TYPE: PRT
<213> ORGANISM: Semliki Forest virus

<400> SEQUENCE: 31

Pro His Tyr Gln Gln Cys Val Asp His Ala Met Lys Leu Gln Met Leu
 1               5                  10                  15

Gly Gly Asp Ala Ile Arg Leu Leu Lys Pro Gly Gly Ile Leu Met Arg
            20                  25                  30

Ala Tyr Gly Tyr Ala Asp Lys Ile Ser Glu Ala Val Val Ser Ser Leu
        35                  40                  45

Ser Arg Lys Phe Ser Ser Ala Arg Val Ile Arg Pro Asp Cys Val Thr
    50                  55                  60

Ser Asn Thr Glu Val Phe Leu Leu Phe Ser Asn Phe Asp Asn Gly Lys
65                  70                  75                  80

Arg Pro Ser Thr Leu His Gln Met Asn Thr Lys Leu Ser Ala Val Tyr
                85                  90                  95

Ala Gly Glu Ala Met His Thr Ala Gly Cys Ala Pro Ser Tyr
            100                 105                 110
```

```
<210> SEQ ID NO 32
<211> LENGTH: 111
<212> TYPE: PRT
<213> ORGANISM: Artificial Sequence
<220> FEATURE:
<223> OTHER INFORMATION: chimeric nsp2

<400> SEQUENCE: 32

Pro His Tyr Gln Gln Cys Glu Asp His Ala Ile Lys Leu Ser Met Leu
 1               5                  10                  15

Thr Lys Lys Ala Cys Leu His Leu Asn Pro Gly Gly Thr Cys Val Ser
            20                  25                  30

Ile Gly Tyr Gly Tyr Ala Asp Arg Ala Ser Glu Ser Ile Ile Gly Ala
        35                  40                  45

Ile Ala Arg Gln Phe Lys Phe Ser Arg Val Cys Lys Pro Lys Ser Ser
    50                  55                  60

Leu Glu Glu Thr Glu Val Leu Phe Val Phe Ile Gly Tyr Asp Arg Lys
65                  70                  75                  80

Ala Arg Thr His Asn Pro Tyr Lys Leu Ser Ser Thr Leu Thr Asn Ile
                85                  90                  95

Tyr Thr Gly Ser Arg Leu His Glu Ala Gly Cys Ala Pro Ser Tyr
            100                 105                 110

<210> SEQ ID NO 33
<211> LENGTH: 111
<212> TYPE: PRT
<213> ORGANISM: Sindbis virus

<400> SEQUENCE: 33

Pro His Phe Gln Gln Cys Glu Asp His Ala Ala Thr Leu Lys Thr Leu
 1               5                  10                  15

Ser Arg Ser Ala Ile Asn Cys Leu Asn Pro Gly Gly Thr Leu Val Val
            20                  25                  30

Lys Ser Tyr Gly Tyr Ala Asp Arg Asn Ser Glu Asp Val Val Thr Ala
        35                  40                  45

Leu Ala Arg Lys Phe Val Arg Val Ser Ala Ala Arg Pro Asp Cys Val
    50                  55                  60

Ser Ser Asn Thr Glu Met Tyr Leu Ile Phe Arg Gln Leu Asp Asn Ser
65                  70                  75                  80

Arg Thr Arg Gln Phe Thr Pro His His Leu Asn Cys Val Ile Ser Ser
                85                  90                  95

Val Tyr Glu Gly Thr Arg Asp Gly Val Gly Ala Ala Pro Ser Tyr
            100                 105                 110

<210> SEQ ID NO 34
<211> LENGTH: 111
<212> TYPE: PRT
<213> ORGANISM: Eastern equine encephalitis virus

<400> SEQUENCE: 34

Pro His Tyr Gln Gln Cys Glu Asp His Ala Ile His His Ser Met Leu
 1               5                  10                  15

Thr Arg Lys Ala Val Asp His Leu Asn Lys Gly Gly Thr Cys Ile Ala
            20                  25                  30

Leu Gly Tyr Gly Thr Ala Asp Arg Ala Thr Glu Asn Ile Ile Ser Ala
        35                  40                  45

Val Ala Arg Ser Phe Arg Phe Ser Arg Val Cys Gln Pro Lys Cys Ala
```

```
    50                  55                  60

Trp Glu Asn Thr Glu Val Ala Phe Val Phe Phe Gly Lys Asp Asn Gly
65                  70                  75                  80

Asn His Leu Gln Asp Gln Asp Arg Leu Ser Val Val Leu Asn Asn Ile
                85                  90                  95

Tyr Gln Gly Ser Thr Gln His Glu Ala Gly Arg Ala Pro Ala Tyr
            100                 105                 110

<210> SEQ ID NO 35
<211> LENGTH: 112
<212> TYPE: PRT
<213> ORGANISM: Artificial Sequence
<220> FEATURE:
<223> OTHER INFORMATION: consensus sequence
<221> NAME/KEY: VARIANT
<222> LOCATION: (1)...(112)
<223> OTHER INFORMATION: Xaa = Any Amino Acid
<221> NAME/KEY: VARIANT
<222> LOCATION: (1)...(112)
<223> OTHER INFORMATION: Xaa = Any Amino Acid

<400> SEQUENCE: 35

Pro His Tyr Gln Gln Cys Glu Asp His Ala Ile Lys Leu Ser Met Leu
 1              5                   10                  15

Thr Arg Lys Ala Ile Xaa His Leu Asn Pro Gly Gly Thr Cys Val Ser
            20                  25                  30

Leu Gly Tyr Gly Tyr Ala Asp Arg Ala Ser Glu Ala Ile Ile Ser Ala
        35                  40                  45

Leu Ala Arg Lys Phe Lys Phe Ser Arg Val Cys Arg Pro Lys Cys Val
    50                  55                  60

Ser Ser Asn Thr Glu Val Phe Leu Val Phe Xaa Gly Phe Asp Asn Gly
65                  70                  75                  80

Lys Xaa Arg Xaa Xaa Thr Pro His Lys Leu Ser Ser Val Leu Ser Asn
                85                  90                  95

Ile Tyr Xaa Gly Ser Thr Leu His Glu Ala Gly Cys Ala Pro Ser Tyr
            100                 105                 110

<210> SEQ ID NO 36
<211> LENGTH: 1245
<212> TYPE: PRT
<213> ORGANISM: Sindbis virus

<400> SEQUENCE: 36

Met Asn Arg Gly Phe Phe Asn Met Leu Gly Arg Arg Pro Phe Pro Ala
 1              5                   10                  15

Pro Thr Ser Met Trp Arg Pro Arg Arg Arg Arg Gln Ala Ala Pro Met
            20                  25                  30

Pro Ala Arg Asn Gly Leu Ala Ser Gln Ile Gln Gln Leu Thr Thr Ala
        35                  40                  45

Val Ser Ala Leu Val Ile Gly Gln Ala Ala Arg Pro Gln Gln Pro Arg
    50                  55                  60

Pro Arg Pro Pro Pro Arg Gln Lys Lys Gln Pro Pro Lys Gln Leu Pro
65                  70                  75                  80

Lys Pro Lys Lys Pro Lys Thr Gln Asp Lys Lys Lys Arg Gln Pro Ala
                85                  90                  95

Lys Pro Lys Pro Gly Lys Arg Gln Arg Met Ala Leu Lys Leu Glu Ala
            100                 105                 110

Asp Arg Leu Phe Asp Val Lys Asn Glu Asn Gly Asp Val Ile Gly His
        115                 120                 125
```

-continued

```
Ala Leu Ala Met Glu Gly Lys Val Met Lys Pro Leu His Val Lys Gly
            130                 135                 140

Thr Ile Asp His Pro Val Leu Ser Lys Leu Lys Phe Thr Lys Ser Ser
145                 150                 155                 160

Ala Tyr Asp Met Glu Phe Ala Gln Leu Pro Val Asn Met Arg Ser Glu
                165                 170                 175

Ala Phe Thr Tyr Thr Ser Glu His Pro Glu Gly Phe Tyr Asn Trp His
            180                 185                 190

His Gly Ala Val Gln Tyr Ser Gly Arg Phe Thr Ile Pro Arg Gly
        195                 200                 205

Val Gly Gly Arg Gly Asp Ser Gly Arg Pro Ile Met Asp Asn Ala Gly
210                 215                 220

Arg Val Val Ala Ile Val Leu Gly Gly Ala Asp Glu Gly Thr Arg Thr
225                 230                 235                 240

Ala Leu Ser Val Val Thr Trp Asn Ser Lys Gly Lys Thr Ile Lys Thr
            245                 250                 255

Ser Pro Glu Gly Thr Glu Trp Ser Ala Ala Pro Leu Val Thr Ala
                260                 265                 270

Met Cys Leu Leu Gly Asn Val Ser Phe Pro Cys Asn Arg Pro Pro Thr
        275                 280                 285

Cys Tyr Thr Arg Glu Pro Ser Arg Ala Leu Asp Ile Leu Glu Glu Asn
    290                 295                 300

Val Asn His Glu Asp Tyr Asp Thr Leu Leu Asp Ala Ile Leu Arg Cys
305                 310                 315                 320

Asp Phe Ser Gly Arg Asn Lys Arg Ser Val Thr Gly Asp Phe Thr Leu
            325                 330                 335

Thr Ser Pro Tyr Leu Gly Thr Cys Pro Tyr Cys His His Thr Glu Pro
                340                 345                 350

Cys Phe Ser Pro Ile Lys Ile Glu Gln Val Trp Asp Glu Pro Asp Asp
        355                 360                 365

Thr Thr Ile Arg Ile Gln Thr Ser Ala Gln Phe Gly Tyr Asp Gln Ser
    370                 375                 380

Gly Ala Thr Ser Val Asn Lys Tyr Arg Tyr Met Ser Phe Asp Gln Asp
385                 390                 395                 400

His Thr Val Lys Glu Gly Gln Met Asp Asp Ile Lys Ile Ser Thr Ser
            405                 410                 415

Gly Pro Cys Arg Arg Leu Gly His Lys Gly Tyr Phe Leu Leu Ala Lys
                420                 425                 430

Cys Pro Pro Gly Asp Ser Val Thr Val Ser Ile Val Ser Ser Ser Ser
        435                 440                 445

Thr Thr Ser Cys Thr Leu Ala Arg Lys Ile Lys Pro Lys Phe Val Gly
    450                 455                 460

Arg Glu Arg Tyr Asp Leu Pro Pro Val Tyr Gly Lys Asn Ile Pro Cys
465                 470                 475                 480

Arg Met Tyr Asp Arg Leu Lys Glu Thr Ser Ala Gly Tyr Ile Thr Met
            485                 490                 495

His Arg Pro Gly Pro His Ala Tyr Thr Ser Tyr Leu Glu Glu Ala Ser
                500                 505                 510

Gly Lys Ile Tyr Ala Lys Pro Pro Ser Gly Lys Asn Ile Thr Tyr Glu
        515                 520                 525

Cys Lys Cys Gly Asp Tyr Lys Thr Gly Thr Val Lys Thr Arg Thr Glu
    530                 535                 540
```

-continued

```
Ile Thr Gly Cys Thr Ala Ile Lys Gln Cys Val Ala Tyr Lys Ser Asp
545                 550                 555                 560

Gln Thr Lys Trp Val Phe Asn Ser Pro Asp Leu Ile Arg His Ala Asp
                565                 570                 575

His Ala Ala Gln Gly Lys Leu His Leu Pro Phe Arg Leu Val Pro Ser
            580                 585                 590

Ser Cys Lys Val Pro Val Ala His Ala Pro Ser Val Val His Gly Phe
        595                 600                 605

Lys His Ile Ser Leu Gln Leu Asp Thr Asp His Leu Thr Leu Leu Thr
    610                 615                 620

Thr Arg Arg Leu Gly Ala Asn Pro Glu Pro Thr Ser Glu Trp Ile Ile
625                 630                 635                 640

Gly Lys Thr Val Arg Asn Phe Ser Val Gly Arg Asp Gly Leu Glu Tyr
                645                 650                 655

Thr Trp Gly Asn His Asp Pro Val Arg Val Tyr Ala Gln Glu Ser Ala
            660                 665                 670

Pro Gly Asp Pro His Gly Trp Pro His Glu Ile Gln His Tyr Tyr
        675                 680                 685

His Arg His Pro Ala Tyr Thr Ile Leu Thr Val Val Ser Ala Ala Val
    690                 695                 700

Ala Val Leu Ile Gly Leu Thr Val Ala Ala Leu Cys Thr Cys Lys Ala
705                 710                 715                 720

Arg Arg Glu Cys Leu Thr Pro Tyr Ala Leu Ala Pro Asn Ala Val Val
                725                 730                 735

Pro Thr Ser Ile Ala Leu Leu Cys Cys Ile Arg Ser Ala Asn Ala Glu
            740                 745                 750

Thr Phe Ser Glu Thr Met Ser Tyr Leu Trp Ser Asn Ser Gln Pro Phe
        755                 760                 765

Phe Trp Ala Gln Leu Cys Ile Pro Leu Ala Ala Val Val Ile Leu Val
    770                 775                 780

Arg Cys Cys Ser Cys Cys Leu Pro Phe Leu Val Val Ala Gly Val Tyr
785                 790                 795                 800

Leu Gly Lys Val Asp Ala Tyr Glu His Ala Thr Thr Ile Pro Asn Val
                805                 810                 815

Pro Lys Ile Pro Tyr Lys Ala Leu Val Glu Arg Ser Gly Tyr Ala Pro
            820                 825                 830

Leu Asn Leu Glu Ile Thr Val Val Ser Ser Gln Val Leu Pro Ser Thr
        835                 840                 845

Asn Gln Glu Tyr Ile Thr Cys Lys Phe Thr Thr Val Val Pro Ser Pro
    850                 855                 860

Lys Val Lys Cys Cys Gly Ser Leu Glu Cys Gln Pro Ala Ala His Ala
865                 870                 875                 880

Asp Tyr Asn Cys Lys Val Phe Gly Gly Val Tyr Pro Phe Met Trp Gly
                885                 890                 895

Gly Ala Gln Cys Phe Cys Asp Ser Glu Asn Thr Gln Met Ser Glu Ala
            900                 905                 910

Tyr Val Lys Leu Ser Ala Asp Cys Val Thr Asp Tyr Ala Gln Ala Val
        915                 920                 925

Asn Val His Thr Ala Ala Met Lys Val Gly Leu Arg Ile Val Tyr Gly
    930                 935                 940

Asn Thr Thr Ser Tyr Leu Asp Val Tyr Val Asn Gly Val Thr Pro Gly
945                 950                 955                 960

Thr Ser Lys Asp Leu Lys Val Ile Ala Gly Pro Val Ser Ser Ser Phe
```

```
                    965                 970                 975

Thr Pro Phe Asn His Lys Val Val Ile Tyr Arg Gly Leu Val Tyr Asn
                    980                 985                 990

Tyr Asp Phe Pro Glu Tyr Gly Ala Met Lys Pro Gly Val Phe Gly Asp
                995                1000                1005

Ile Gln Ala Thr Ser Leu Thr Ser Arg Asp Leu Ile Ala Ser Thr Asp
            1010                1015                1020

Ile Arg Leu Leu Lys Pro Ser Val Lys Asn Val His Val Pro Tyr Thr
1025                1030                1035                1040

Gln Ala Ala Ser Gly Phe Glu Met Trp Lys Asn Asn Ser Gly Arg Pro
                1045                1050                1055

Leu Gln Glu Thr Ala Pro Phe Gly Cys Lys Ile Ala Val Asn Pro Leu
            1060                1065                1070

Arg Ala Val Asp Cys Ser Tyr Gly Asn Ile Pro Ile Ser Ile Asp Ile
        1075                1080                1085

Pro Asn Ala Ala Phe Ile Arg Ile Ser Asp Ala Pro Leu Val Ser Thr
        1090                1095                1100

Val Lys Cys Glu Val Ser Gly Cys Thr Tyr Ser Ala Asp Phe Gly Gly
1105                1110                1115                1120

Met Ala Thr Leu Gln Tyr Val Ser Asp Arg Glu Gly Gln Cys Pro Val
            1125                1130                1135

His Ser His Ser Ser Thr Ala Thr Leu Gln Glu Ser Thr Val His Val
        1140                1145                1150

Leu Glu Lys Gly Ala Val Thr Val His Phe Ser Thr Ala Ser Pro Gln
            1155                1160                1165

Ala Asn Phe Ile Ile Ser Leu Cys Gly Lys Lys Thr Thr Cys Asn Ala
        1170                1175                1180

Glu Cys Lys Pro Pro Ala Asp His Ile Val Ser Thr Pro His Lys Ile
1185                1190                1195                1200

Asp Gln Glu Phe Gln Thr Ala Ile Ser Lys Thr Ser Trp Ser Trp Leu
                1205                1210                1215

Leu Ala Leu Phe Gly Gly Ala Ser Ser Leu Leu Ile Ile Gly Leu Met
            1220                1225                1230

Ile Phe Thr Cys Ser Met Leu Leu Thr Ser Thr Arg Arg
        1235                1240                1245

<210> SEQ ID NO 37
<211> LENGTH: 1254
<212> TYPE: PRT
<213> ORGANISM: Semliki Forest virus

<400> SEQUENCE: 37

Pro Met Asn Tyr Ile Pro Thr Gln Thr Phe Tyr Gly Arg Arg Trp Arg
1               5                   10                  15

Pro Arg Pro Ala Ala Arg Pro Trp Pro Leu Gln Ala Thr Pro Val Ala
                20                  25                  30

Pro Val Val Pro Asp Phe Gln Ala Gln Gln Met Gln Gln Leu Ile Ser
            35                  40                  45

Ala Val Asn Ala Leu Thr Met Arg Gln Asn Ala Ile Ala Pro Ala Arg
        50                  55                  60

Pro Pro Lys Pro Lys Lys Lys Lys Thr Thr Lys Pro Lys Pro Lys Thr
65                  70                  75                  80

Gln Pro Lys Lys Ile Asn Gly Lys Thr Gln Gln Gln Lys Lys Lys Asp
                85                  90                  95
```

-continued

Lys Gln Ala Asp Lys Lys Lys Lys Pro Gly Lys Arg Glu Arg Met
            100                 105                 110

Cys Met Lys Ile Glu Asn Asp Cys Ile Phe Glu Val Lys His Glu Gly
            115                 120                 125

Lys Val Thr Gly Tyr Ala Cys Leu Val Gly Asp Lys Val Met Lys Pro
            130                 135                 140

Ala His Val Lys Gly Val Ile Asp Asn Ala Asp Leu Ala Lys Leu Ala
145                 150                 155                 160

Phe Lys Lys Ser Ser Lys Tyr Asp Leu Glu Cys Ala Gln Ile Pro Val
                165                 170                 175

His Met Arg Ser Asp Ala Ser Lys Tyr Thr His Glu Lys Pro Glu Gly
            180                 185                 190

His Tyr Asn Trp His His Gly Ala Val Gln Tyr Ser Gly Gly Arg Phe
            195                 200                 205

Thr Ile Pro Thr Gly Ala Gly Lys Pro Gly Asp Ser Gly Arg Pro Ile
            210                 215                 220

Phe Asp Asn Lys Gly Arg Val Val Ala Ile Val Leu Gly Gly Ala Asn
225                 230                 235                 240

Glu Gly Ser Arg Thr Ala Leu Ser Val Val Thr Trp Asn Lys Asp Met
                245                 250                 255

Val Thr Arg Val Thr Pro Glu Gly Ser Glu Glu Trp Ser Ala Pro Leu
            260                 265                 270

Ile Thr Ala Met Cys Val Leu Ala Asn Ala Thr Phe Pro Cys Phe Gln
            275                 280                 285

Pro Pro Cys Val Pro Cys Cys Tyr Glu Asn Asn Ala Glu Ala Thr Leu
290                 295                 300

Arg Met Leu Glu Asp Asn Val Asp Arg Pro Gly Tyr Tyr Asp Leu Leu
305                 310                 315                 320

Gln Ala Ala Leu Thr Cys Arg Asn Gly Thr Arg His Arg Arg Ser Val
                325                 330                 335

Ser Gln His Phe Asn Val Tyr Lys Ala Thr Arg Pro Tyr Ile Ala Tyr
            340                 345                 350

Cys Ala Asp Cys Gly Ala Gly His Ser Cys His Ser Pro Val Ala Ile
            355                 360                 365

Glu Ala Val Arg Ser Glu Ala Thr Asp Gly Met Leu Lys Ile Gln Phe
370                 375                 380

Ser Ala Gln Ile Gly Ile Asp Lys Ser Asp Asn His Asp Tyr Thr Lys
385                 390                 395                 400

Ile Arg Tyr Ala Asp Gly His Ala Ile Glu Asn Ala Val Arg Ser Ser
                405                 410                 415

Leu Lys Val Ala Thr Ser Gly Asp Cys Phe Val His Gly Thr Met Gly
            420                 425                 430

His Phe Ile Leu Ala Lys Cys Pro Pro Gly Glu Phe Leu Gln Val Ser
            435                 440                 445

Ile Gln Asp Thr Arg Asn Ala Val Arg Ala Cys Arg Ile Gln Tyr His
            450                 455                 460

His Asp Pro Gln Pro Val Gly Arg Glu Lys Phe Thr Ile Arg Pro His
465                 470                 475                 480

Tyr Gly Lys Glu Ile Pro Cys Thr Thr Tyr Gln Gln Thr Thr Ala Glu
                485                 490                 495

Thr Val Glu Glu Ile Asp Met His Met Pro Pro Asp Thr Pro Asp Arg
            500                 505                 510

Thr Leu Leu Ser Gln Gln Ser Gly Asn Val Lys Ile Thr Val Gly Gly

```
            515                 520                 525
Lys Lys Val Lys Tyr Asn Cys Thr Cys Gly Thr Gly Asn Val Gly Thr
        530                 535                 540

Thr Asn Ser Asp Met Thr Ile Asn Thr Cys Leu Ile Glu Gln Cys His
545                 550                 555                 560

Val Ser Val Thr Asp His Lys Lys Trp Gln Phe Asn Ser Pro Phe Val
                565                 570                 575

Pro Arg Ala Asp Glu Pro Ala Arg Lys Gly Lys Val His Ile Pro Phe
                580                 585                 590

Pro Leu Asp Asn Ile Thr Cys Arg Val Pro Met Ala Arg Glu Pro Thr
                595                 600                 605

Val Ile His Gly Lys Arg Glu Val Thr Leu His Leu His Pro Asp His
        610                 615                 620

Pro Thr Leu Phe Ser Tyr Arg Thr Leu Gly Asp Pro Gln Tyr His
625                 630                 635                 640

Glu Glu Trp Val Thr Ala Ala Val Glu Arg Thr Ile Pro Val Pro Val
                645                 650                 655

Asp Gly Met Glu Tyr His Trp Gly Asn Asn Asp Pro Val Arg Leu Trp
                660                 665                 670

Ser Gln Leu Thr Thr Glu Gly Lys Pro His Gly Trp Pro His Gln Ile
        675                 680                 685

Val Gln Tyr Tyr Gly Leu Tyr Pro Ala Ala Thr Val Ser Ala Val
        690                 695                 700

Val Gly Met Ser Leu Leu Ala Leu Ile Ser Ile Phe Ala Ser Cys Tyr
705                 710                 715                 720

Met Leu Val Ala Ala Arg Ser Lys Cys Leu Thr Pro Tyr Ala Leu Thr
                725                 730                 735

Pro Gly Ala Ala Val Pro Trp Thr Leu Gly Ile Leu Cys Cys Ala Pro
                740                 745                 750

Arg Ala His Ala Ala Ser Val Ala Glu Thr Met Ala Tyr Leu Trp Asp
        755                 760                 765

Gln Asn Gln Ala Leu Phe Trp Leu Glu Phe Ala Ala Pro Val Ala Cys
        770                 775                 780

Ile Leu Ile Ile Thr Tyr Cys Leu Arg Asn Val Leu Cys Cys Cys Lys
785                 790                 795                 800

Ser Leu Ser Phe Leu Val Leu Leu Ser Leu Gly Ala Thr Ala Arg Ala
                805                 810                 815

Tyr Glu His Ser Thr Val Met Pro Asn Val Val Gly Phe Pro Tyr Lys
                820                 825                 830

Ala His Ile Glu Arg Pro Gly Tyr Ser Pro Leu Thr Leu Gln Met Gln
        835                 840                 845

Val Val Glu Thr Ser Leu Glu Pro Thr Leu Asn Leu Glu Tyr Ile Thr
        850                 855                 860

Cys Glu Tyr Lys Thr Val Val Pro Ser Pro Tyr Val Lys Cys Cys Gly
865                 870                 875                 880

Ala Ser Glu Cys Ser Thr Lys Glu Lys Pro Asp Tyr Gln Cys Lys Val
                885                 890                 895

Tyr Thr Gly Val Tyr Pro Phe Met Trp Gly Gly Ala Tyr Cys Phe Cys
                900                 905                 910

Asp Ser Glu Asn Thr Gln Leu Ser Glu Ala Tyr Val Asp Arg Ser Asp
                915                 920                 925

Val Cys Arg His Asp His Ala Ser Ala Tyr Lys Ala His Thr Ala Ser
        930                 935                 940
```

Leu Lys Ala Lys Val Arg Val Met Tyr Gly Asn Val Asn Gln Thr Val
945                 950                 955                 960

Asp Val Tyr Val Asn Gly Asp His Ala Val Thr Ile Gly Gly Thr Gln
                965                 970                 975

Phe Ile Phe Gly Pro Leu Ser Ser Ala Trp Thr Pro Phe Asp Asn Lys
            980                 985                 990

Ile Val Val Tyr Lys Asp Glu Val Phe Asn Gln Asp Phe Pro Pro Tyr
        995                 1000                1005

Gly Ser Gly Gln Pro Gly Arg Phe Gly Asp Ile Gln Ser Arg Thr Val
    1010                1015                1020

Glu Ser Asn Asp Leu Tyr Ala Asn Thr Ala Leu Lys Leu Ala Arg Pro
1025                1030                1035                1040

Ser Pro Gly Met Val His Val Pro Tyr Thr Gln Thr Pro Ser Gly Phe
                1045                1050                1055

Lys Tyr Trp Leu Lys Glu Lys Gly Thr Ala Leu Asn Thr Lys Ala Pro
            1060                1065                1070

Phe Gly Cys Gln Ile Lys Thr Asn Pro Val Arg Ala Met Asn Cys Ala
        1075                1080                1085

Val Gly Asn Ile Pro Val Ser Met Asn Leu Pro Asp Ser Ala Phe Thr
    1090                1095                1100

Arg Ile Val Glu Ala Pro Thr Ile Ile Asp Leu Thr Cys Thr Val Ala
1105                1110                1115                1120

Thr Cys Thr His Ser Ser Asp Phe Gly Gly Val Leu Thr Leu Thr Tyr
                1125                1130                1135

Lys Thr Asn Lys Asn Gly Asp Cys Ser Val His Ser His Ser Asn Val
            1140                1145                1150

Ala Thr Leu Gln Glu Ala Thr Ala Lys Val Lys Thr Ala Gly Lys Val
        1155                1160                1165

Thr Leu His Phe Ser Thr Ala Ser Ala Ser Pro Ser Phe Val Val Ser
    1170                1175                1180

Leu Cys Ser Ala Arg Ala Thr Cys Ser Ala Ser Cys Glu Pro Pro Lys
1185                1190                1195                1200

Asp His Ile Val Pro Tyr Ala Ala Ser His Ser Asn Val Val Phe Pro
                1205                1210                1215

Asp Met Ser Gly Thr Ala Leu Ser Trp Val Gln Lys Ile Ser Gly Gly
            1220                1225                1230

Leu Gly Ala Phe Ala Ile Gly Ala Ile Leu Val Leu Val Val Val Thr
        1235                1240                1245

Cys Ile Gly Leu Arg Arg
    1250

<210> SEQ ID NO 38
<211> LENGTH: 1255
<212> TYPE: PRT
<213> ORGANISM: Venezuelan equine encephalitis virus

<400> SEQUENCE: 38

Pro Met Phe Pro Tyr Gln Pro Ser Met Tyr Pro Met Gln Pro Ala Pro
1               5                   10                  15

Tyr Arg Pro Tyr Pro Ala Pro Arg Arg Pro Trp Tyr Pro Arg Thr Asp
            20                  25                  30

Pro Phe Leu Ala Leu Gln Val Gln Glu Leu Ala Arg Ser Met Ala Asn
        35                  40                  45

Leu Thr Phe Lys Gln Arg Arg Glu Ser Pro Pro Glu Gly Pro Pro Ala

```
                50                  55                  60
Lys Lys Lys Lys Arg Glu Pro Gln Ala Ala Thr Pro Ile Lys Asn
 65                  70                  75                  80

Ala Gln Lys Lys Asn Gly Lys Gly Lys Lys Pro Lys Gly Ala
                 85                  90                  95

Val Gln Pro Lys Asn Gln Pro Ala Ser Lys Lys Pro Asn Lys Lys
                100                 105                 110

Pro Gly Lys Arg Gln Arg Met Val Met Lys Leu Glu Ser Asp Lys Thr
                115                 120                 125

Phe Pro Ile Met Leu Asp Gly Lys Ile Asn Gly Tyr Ala Cys Val Val
                130                 135                 140

Gly Gly Lys Leu Phe Arg Pro Met His Val Glu Gly Lys Ile Asp Asn
145                 150                 155                 160

Glu Thr Leu Ala Ala Leu Lys Thr Lys Ala Thr Lys Tyr Asp Leu
                165                 170                 175

Glu Tyr Ala Asp Val Pro Gln Ser Met Arg Ala Asp Thr Phe Arg Tyr
                180                 185                 190

Thr His Glu Lys Pro Gln Gly Tyr Tyr Asn Trp His His Gly Ala Val
                195                 200                 205

Gln Tyr Glu Asn Gly Arg Phe Thr Val Pro Lys Gly Val Gly Ala Lys
                210                 215                 220

Gly Asp Ser Gly Arg Pro Ile Leu Asp Asn Gln Gly Arg Val Val Ala
225                 230                 235                 240

Ile Val Leu Gly Gly Val Asn Glu Gly Ser Arg Thr Ala Leu Ser Val
                245                 250                 255

Val Met Trp Thr Glu Lys Gly Val Thr Val Lys Tyr Thr Pro Glu Asn
                260                 265                 270

Cys Glu Gln Trp Ser Leu Val Thr Ala Val Cys Leu Leu Ala Asn Val
                275                 280                 285

Thr Phe Pro Cys Ser Gln Pro Pro Ile Cys Tyr Asp Arg Lys Pro Ser
                290                 295                 300

Glu Thr Leu Ala Met Leu Ser Glu Asn Ile Asp Asn Pro Gly Tyr Asp
305                 310                 315                 320

Val Leu Leu Asp Ser Val Leu Lys Cys Pro Gly Arg Gln Lys Arg Ser
                325                 330                 335

Thr Glu Glu Leu Phe Lys Glu Tyr Lys Leu Thr Lys Pro Tyr Met Ala
                340                 345                 350

Lys Cys Ile Arg Cys Ala Val Gly Ser Cys His Ser Pro Ile Ala Ile
                355                 360                 365

Glu Glu Val Arg Ser Asp Gly His Asp Gly Tyr Ile Arg Ile Gln Thr
370                 375                 380

Ser Ser Gln Tyr Gly Leu Asp Pro Ser Gly Gly Val Lys Ser Arg Thr
385                 390                 395                 400

Met Arg Tyr Asn Leu Gln Gly Asn Ile Glu Glu Ile Pro Leu His Glu
                405                 410                 415

Val Ser Leu His Thr Ser Arg Pro Cys His Ile Ile Asp Gly His Gly
                420                 425                 430

Tyr Phe Leu Leu Ala Arg Cys Pro Glu Gly Asp Ser Leu Thr Met Glu
                435                 440                 445

Phe Lys Lys Asp Thr Val Thr His Ser Cys Ser Val Pro Tyr Lys Val
                450                 455                 460

Lys Phe Ile Pro Val Gly Arg Glu Leu Tyr Thr His Pro Pro Glu His
465                 470                 475                 480
```

```
Gly Thr Asp His Pro Cys Arg Val Tyr Ala His Asp Ala Gln Lys Arg
                485                 490                 495

Gly Ala Tyr Val Glu Met His Leu Pro Gly Ser Glu Val Asp Ser Thr
                500                 505                 510

Leu Leu Ser Met Ser Gly Gly Ala Val Gln Val Asn Pro Pro Ala Gly
                515                 520                 525

Thr Asn Val Leu Val Glu Cys Asn Cys Gly Thr Gln Ile Ser Glu Thr
                530                 535                 540

Val Ser Thr Val Lys Lys Phe Asn Gln Cys Thr Gln Thr Asn Arg Cys
545                 550                 555                 560

Arg Ala Tyr Arg Leu Gln Ser Asp Lys Trp Val Phe Asn Ser Asp Lys
                565                 570                 575

Leu Pro Lys Ala Ser Gly Asp Thr Leu Lys Gly Lys Leu His Val Pro
                580                 585                 590

Phe Leu Leu Ser Glu Ala Lys Cys Thr Val Pro Leu Ala Pro Glu Pro
                595                 600                 605

Val Val Ser Phe Gly Phe Arg Ser Val Ser Leu Lys Leu His Pro Asn
                610                 615                 620

Asn Pro Thr Tyr Leu Thr Thr Arg His Leu Gly Gly Glu Pro Gln Tyr
625                 630                 635                 640

Thr His Glu Leu Ile Ser Glu Pro Val Val Lys Asn Phe Ser Ile Thr
                645                 650                 655

Glu Lys Gly Trp Glu Phe Val Trp Gly Asn His Pro Pro Gln Arg Phe
                660                 665                 670

Trp Ala Gln Glu Thr Ala Pro Gly Asn Pro His Gly Met Pro His Glu
                675                 680                 685

Ile Val Thr His Tyr Tyr Tyr Arg Tyr Pro Met Ser Thr Val Val Gly
                690                 695                 700

Leu Ser Ile Cys Ala Ala Ile Val Ile Ser Ile Ala Ala Ser Leu
705                 710                 715                 720

Cys Leu Leu Cys Lys Ser Arg Val Ser Cys Leu Thr Pro Tyr Arg Leu
                725                 730                 735

Thr Pro Asn Ala Arg Leu Pro Ile Cys Leu Ala Leu Leu Cys Cys Ala
                740                 745                 750

Arg Pro Thr Arg Ala Glu Thr Thr Trp Glu Thr Leu Asp His Leu Trp
                755                 760                 765

Asn Asn Asn Gln Gln Met Phe Trp Leu Gln Leu Leu Ile Pro Leu Ala
770                 775                 780

Ala Leu Ile Val Ile Thr Arg Ile Leu Lys Cys Val Cys Cys Phe Val
785                 790                 795                 800

Pro Phe Leu Val Leu Ala Gly Ala Ala Gly Ala Gly Ala Tyr Glu His
                805                 810                 815

Ala Thr Thr Met Pro Ser Gln Val Gly Ile Pro Phe Asn Thr Ile Val
                820                 825                 830

Asn Arg Ala Gly Tyr Ala Pro Leu Ala Ile Ser Ile Thr Pro Thr Lys
                835                 840                 845

Ile Gln Ile Ile Pro Thr Leu Asn Leu Glu Tyr Ile Thr Cys His Tyr
850                 855                 860

Lys Thr Gly Leu Asp Ser Pro Ala Val Lys Cys Cys Gly Thr Gln Glu
865                 870                 875                 880

Cys Ser Glu Val Thr Arg Pro Asp Glu Lys Cys Lys Val Phe Thr Gly
                885                 890                 895
```

Val Tyr Pro Phe Met Trp Gly Gly Ala Tyr Cys Phe Cys Asp Thr Glu
                900                 905                 910

Asn Ser Gln Val Ser Lys Ala Tyr Val Met Lys Ser Asp Asp Cys Ala
        915                 920                 925

Ala Asp His Ala Gln Ala Tyr Lys Ala His Thr Ala Ala Gln Ala
    930                 935                 940

Phe Leu Asn Ile Thr Val Ala Asp Gln Ser Thr Thr Thr Ile Val Tyr
945                 950                 955                 960

Val Asn Gly Glu Thr Pro Val Asn Phe Asn Gly Ile Arg Leu Thr Ala
                965                 970                 975

Gly Pro Leu Ser Thr Ala Trp Thr Pro Phe Asp Arg Lys Ile Val Gln
        980                 985                 990

Tyr Ala Glu Glu Val Tyr Asn Tyr Asp Phe Pro Glu Tyr Gly Ala Gly
        995                 1000                1005

Thr Ala Gly Ala Phe Gly Asp Ile Gln Ala Arg Thr Thr Ser Thr
    1010                1015                1020

Asp Leu Tyr Ala Asn Thr Asn Leu Val Leu Gln Arg Pro Lys Ser Gly
1025                1030                1035                1040

Thr Val His Val Pro Tyr Thr Gln Ala Pro Ser Gly Phe Glu Gln Trp
                1045                1050                1055

Lys Lys Asp Lys Pro Pro Ser Leu Lys Tyr Thr Ala Pro Phe Gly Cys
        1060                1065                1070

Glu Ile Lys Val Asn Pro Ile Arg Ala Glu Asn Cys Ala Val Gly Ser
        1075                1080                1085

Ile Pro Leu Ser Phe Asp Ile Pro Asp Ala Leu Phe Thr Arg Val Ser
        1090                1095                1100

Glu Thr Pro Thr Leu Ser Asn Ala Glu Cys Thr Leu Asn Glu Cys Val
1105                1110                1115                1120

Tyr Ser Ser Asp Phe Gly Gly Ile Ala Ser Val Lys Tyr Ser Ala Thr
                1125                1130                1135

Lys Ala Gly Lys Cys Ala Val His Ile Pro Ser Gly Thr Ala Thr Val
        1140                1145                1150

Arg Glu Ala Thr Val Asp Leu Val Glu Gln Gly Ser Leu Thr Val His
        1155                1160                1165

Phe Ser Thr Ala Asn Ile His Pro Glu Phe Arg Leu Gln Ile Cys Thr
    1170                1175                1180

Thr Tyr Val Thr Cys Lys Gly Asp Cys His Pro Pro Lys Asp His Ile
1185                1190                1195                1200

Val Thr His Pro Gln Tyr His Ala Gln Thr Phe Thr Ala Ala Val Ser
                1205                1210                1215

Lys Thr Ala Trp Thr Trp Ile Thr Ser Leu Leu Gly Gly Ser Ala Val
        1220                1225                1230

Leu Val Val Ile Gly Leu Ile Leu Ala Ile Ile Val Ala Thr Tyr Val
        1235                1240                1245

Leu Thr Gly Gln Arg Arg Tyr
    1250                1255

<210> SEQ ID NO 39
<211> LENGTH: 1242
<212> TYPE: PRT
<213> ORGANISM: Eastern equine encephalitis virus

<400> SEQUENCE: 39

Pro Met Phe Pro Tyr Pro Thr Leu Asn Tyr Pro Pro Met Ala Pro Ile
1               5                   10                  15

```
Asn Pro Met Ala Tyr Arg Asp Pro Asn Pro Arg Arg Trp Arg
             20                  25              30
Pro Phe Arg Pro Pro Leu Ala Ala Gln Ile Glu Asp Leu Arg Arg Ser
         35                  40                  45
Ile Ala Asn Leu Thr Leu Lys Gln Arg Ala Pro Asn Pro Ala Gly
 50                  55                  60
Pro Pro Ala Lys Arg Lys Lys Pro Ala Pro Ser Leu Ser Leu Arg Arg
 65                  70                  75                  80
Lys Lys Lys Arg Pro Pro Pro Ala Lys Lys Gln Lys Arg Lys Pro
             85                  90                  95
Lys Pro Gly Lys Arg Gln Arg Met Cys Met Lys Leu Glu Ser Asp Lys
            100                 105                 110
Thr Phe Pro Ile Met Leu Asn Gly Gln Val Asn Gly Tyr Ala Cys Val
            115                 120                 125
Val Gly Gly Arg Val Phe Lys Pro Leu His Val Glu Gly Arg Ile Asp
130                 135                 140
Asn Glu Gln Leu Ala Ala Ile Lys Leu Lys Lys Ala Ser Ile Tyr Asp
145                 150                 155                 160
Leu Glu Tyr Gly Asp Val Pro Gln Cys Met Lys Ser Asp Thr Leu Gln
                165                 170                 175
Tyr Thr Ser Asp Lys Pro Pro Gly Phe Tyr Asn Trp His His Gly Ala
            180                 185                 190
Val Gln Tyr Glu Asn Asn Arg Phe Thr Val Pro Arg Gly Val Gly Gly
            195                 200                 205
Lys Gly Asp Ser Gly Arg Pro Ile Leu Asp Asn Lys Gly Arg Val Val
            210                 215                 220
Ala Ile Val Leu Gly Gly Val Asn Glu Gly Ser Arg Thr Ala Leu Ser
225                 230                 235                 240
Val Val Thr Trp Asn Gln Lys Gly Val Thr Val Lys Asp Thr Pro Glu
                245                 250                 255
Gly Ser Glu Pro Trp Ser Leu Ala Thr Val Met Cys Val Leu Ala Asn
            260                 265                 270
Ile Thr Phe Pro Cys Asp Gln Pro Pro Cys Met Pro Cys Cys Tyr Glu
            275                 280                 285
Lys Asn Pro His Glu Thr Leu Thr Met Leu Glu Gln Asn Tyr Asp Ser
290                 295                 300
Arg Ala Tyr Asp Gln Leu Leu Asp Ala Ala Val Lys Cys Asn Ala Arg
305                 310                 315                 320
Arg Thr Arg Arg Asp Leu Asp Thr His Phe Thr Gln Tyr Lys Leu Ala
                325                 330                 335
Arg Pro Tyr Ile Ala Asp Cys Pro Asn Cys Gly His Ser Arg Cys Asp
            340                 345                 350
Ser Pro Ile Ala Ile Glu Glu Val Arg Gly Asp Ala His Ala Gly Val
            355                 360                 365
Ile Arg Ile Gln Thr Ser Ala Met Phe Gly Leu Lys Thr Asp Gly Val
            370                 375                 380
Asp Leu Ala Tyr Met Ser Phe Met Asn Gly Lys Thr Gln Lys Ser Ile
385                 390                 395                 400
Lys Ile Asp Asn Leu His Val Arg Thr Ser Ala Pro Cys Ser Leu Val
                405                 410                 415
Ser His His Gly Tyr Tyr Ile Leu Ala Gln Cys Pro Pro Gly Asp Thr
            420                 425                 430
```

```
Val Thr Val Gly Phe His Asp Gly Pro Asn Arg His Thr Cys Thr Val
            435                 440                 445

Ala His Lys Val Glu Phe Arg Pro Val Gly Arg Glu Lys Tyr Arg His
        450                 455                 460

Pro Pro Glu His Gly Val Glu Leu Pro Cys Asn Arg Tyr Thr His Lys
465                 470                 475                 480

Arg Ala Asp Gln Gly His Tyr Val Glu Met His Gln Pro Gly Leu Val
                485                 490                 495

Ala Asp His Ser Leu Leu Ser Ile His Ser Ala Lys Val Lys Ile Thr
            500                 505                 510

Val Pro Ser Gly Ala Gln Val Lys Tyr Tyr Cys Lys Cys Pro Asp Val
        515                 520                 525

Arg Glu Gly Thr Thr Ser Ser Asp Tyr Thr Thr Cys Thr Asp Val
530                 535                 540

Lys Gln Cys Arg Ala Tyr Leu Ile Asp Asn Lys Lys Trp Val Tyr Asn
545                 550                 555                 560

Ser Gly Arg Leu Pro Arg Gly Glu Gly Asp Thr Phe Lys Gly Lys Leu
                565                 570                 575

His Val Pro Phe Val Pro Val Lys Ala Lys Cys Ile Ala Thr Leu Ala
            580                 585                 590

Pro Glu Pro Leu Val Glu His Lys His Arg Thr Leu Ile Leu His Leu
        595                 600                 605

Tyr Pro Asp His Pro Thr Leu Leu Thr Thr Arg Ser Leu Gly Ser Asp
    610                 615                 620

Ala Asn Pro Thr Arg Gln Trp Ile Glu Arg Pro Thr Thr Val Asn Phe
625                 630                 635                 640

Thr Val Thr Gly Glu Gly Leu Glu Tyr Thr Trp Gly Asn His Pro Pro
                645                 650                 655

Lys Arg Val Trp Ala Gln Glu Ser Gly Glu Gly Asn Pro His Gly Trp
            660                 665                 670

Pro His Glu Val Val Val Tyr Tyr Tyr Asn Arg Tyr Pro Leu Thr Thr
        675                 680                 685

Ile Ile Gly Leu Cys Thr Cys Val Ala Ile Ile Met Val Ser Cys Val
    690                 695                 700

Thr Ser Val Trp Leu Leu Cys Arg Thr Arg Asn Leu Cys Ile Thr Pro
705                 710                 715                 720

Tyr Lys Leu Ala Pro Asn Ala Gln Val Pro Ile Leu Leu Ala Leu Leu
                725                 730                 735

Cys Cys Ile Lys Pro Thr Arg Ala Asp Asp Thr Leu Gln Val Leu Asn
            740                 745                 750

Tyr Leu Trp Asn Asn Asn Gln Asn Phe Phe Trp Met Gln Thr Leu Ile
        755                 760                 765

Pro Leu Ala Ala Leu Ile Val Cys Met Arg Met Leu Arg Cys Leu Phe
    770                 775                 780

Cys Cys Gly Pro Ala Phe Leu Leu Val Cys Gly Ala Leu Gly Ala Ala
785                 790                 795                 800

Ala Tyr Glu His Thr Ala Val Met Pro Asn Lys Val Gly Ile Pro Tyr
                805                 810                 815

Lys Ala Leu Val Glu Arg Pro Gly Tyr Ala Pro Val His Leu Gln Ile
            820                 825                 830

Gln Leu Val Asn Thr Arg Ile Ile Pro Ser Thr Asn Leu Glu Tyr Ile
        835                 840                 845

Thr Cys Lys Tyr Lys Thr Lys Val Pro Ser Pro Val Val Lys Cys Cys
```

```
                850                 855                 860
Gly Ala Thr Gln Cys Thr Ser Lys Pro His Pro Asp Tyr Gln Cys Gln
865                 870                 875                 880

Val Phe Thr Gly Val Tyr Pro Phe Met Trp Gly Gly Ala Tyr Cys Phe
                    885                 890                 895

Cys Asp Thr Glu Asn Thr Gln Met Ser Glu Ala Tyr Val Glu Arg Ser
                900                 905                 910

Glu Glu Cys Ser Ile Asp His Ala Lys Ala Tyr Lys Val His Thr Gly
            915                 920                 925

Thr Val Gln Ala Met Val Asn Ile Thr Tyr Gly Ser Val Ser Trp Arg
930                 935                 940

Ser Ala Asp Val Tyr Val Asn Gly Glu Thr Pro Ala Lys Ile Gly Asp
945                 950                 955                 960

Ala Lys Leu Ile Ile Gly Pro Leu Ser Ser Ala Trp Ser Pro Phe Asp
                965                 970                 975

Asn Lys Val Val His Gly His Glu Val Tyr Asn Tyr Asp Phe Pro
                980                 985                 990

Glu Tyr Gly Thr Gly Lys Ala Gly Ser Phe Gly Asp Leu Gln Ser Arg
            995                 1000                1005

Thr Ser Thr Ser Asn Asp Leu Tyr Ala Asn Thr Asn Leu Lys Leu Gln
1010                1015                1020

Arg Pro Gln Ala Gly Ile Val His Thr Pro Phe Thr Gln Ala Pro Ser
1025                1030                1035                1040

Gly Phe Glu Arg Trp Lys Arg Asp Lys Gly Ala Pro Leu Asn Asp Val
                1045                1050                1055

Ala Pro Phe Gly Cys Ser Ile Ala Leu Glu Pro Leu Arg Ala Glu Asn
                1060                1065                1070

Cys Ala Val Gly Ser Ile Pro Ile Ser Ile Asp Ile Pro Asp Ala Ala
                1075                1080                1085

Phe Thr Arg Ile Ser Glu Thr Pro Thr Val Ser Asp Leu Glu Cys Lys
                1090                1095                1100

Ile Thr Glu Cys Thr Tyr Ala Ser Asp Phe Gly Gly Ile Ala Thr Val
1105                1110                1115                1120

Ala Tyr Lys Ser Ser Lys Ala Gly Asn Cys Pro Ile His Ser Pro Ser
                1125                1130                1135

Gly Val Ala Val Ile Lys Glu Asn Asp Val Thr Leu Ala Glu Ser Gly
                1140                1145                1150

Ser Phe Thr Phe His Phe Ser Thr Ala Asn Ile His Pro Ala Phe Lys
                1155                1160                1165

Leu Gln Val Cys Thr Ser Ala Val Thr Cys Lys Gly Asp Cys Lys Pro
                1170                1175                1180

Pro Lys Asp His Ile Val Asp Tyr Pro Ala Gln His Thr Glu Ser Phe
1185                1190                1195                1200

Thr Ser Ala Ile Ser Ala Thr Ala Trp Ser Trp Leu Lys Val Leu Val
                1205                1210                1215

Gly Gly Thr Ser Ala Phe Ile Val Leu Gly Leu Ile Ala Thr Ala Val
                1220                1225                1230

Val Ala Leu Val Leu Phe Phe His Arg His
                1235                1240
```

US 9,234,181 B2

RNA EXPRESSION CASSETTE AND CELLS FOR MAKING ALPHAVIRUS PARTICLES

This application claims the benefit of and incorporates by reference Ser. No. 60/990,088 filed Nov. 26, 2007.

This invention was supported by Contract No. HHSN266200500007C from the National Institutes of Health. The U.S. Government may have certain rights in the invention.

This application incorporates by reference the contents of a 112 kb text file created on Apr. 22, 2011 and named "12744878sequencelisting.txt," which is the sequence listing for this application.

FIELD OF THE INVENTION

The invention relates to the preparation of recombinant alphavirus particles.

BACKGROUND OF THE INVENTION

Recombinant alphavirus particles (alphavirus replicon particles) have great potential for use in protein production, antigen delivery, and various therapeutic applications. Alphavirus packaging cell lines (PCL) are the most efficient and cost effective way to generate alphavirus replicon particles. One obstacle in the development of alphavirus packaging cell lines, however, is the low particle yield. On the other hand, generation of RCV (replication competent viral particles) is a potential problem when generating large numbers of recombinant alphavirus particles. The probability of recombination can be greatly reduced by dividing the defective helpers in two separate cassettes, because multiple switches would be required to produce an infectious RNA. However, it is possible that large-scale production could still generate RCV. Thus, there is a need in the art for methods of increasing the productivity of PCL and of reducing the possibility that replication competent virus may be generated during large scale production of recombinant alphavirus particles.

BRIEF DESCRIPTION OF THE FIGURES

FIG. 2A, SFV Nsp2, SEQ ID NO:14; Nsp2 VCR-Chim, SEQ ID NO:15; Sindbis Nsp2, SEQ ID NO:16; EEE Nsp2, SEQ ID NO:17; consensus, SEQ ID NO:18. FIG. 2B, SFV Nsp2, SEQ ID NO:21; Nsp2 VCR-Chim, SEQ ID NO:22; Sindbis Nsp2, SEQ ID NO:23; EEE Nsp2, SEQ ID NO:24; consensus, SEQ ID NO:25. FIG. 2C, SFV Nsp2, SEQ ID NO:26; Nsp2 VCR-Chim, SEQ ID NO:27; Sindbis Nsp2, SEQ ID NO:28; EEE Nsp2, SEQ ID NO:29; consensus, SEQ ID NO:30. FIG. 2D, SFV Nsp2, SEQ ID NO:31; Nsp2 VCR-Chim, SEQ ID NO:32; Sindbis Nsp2, SEQ ID NO:33; EEE Nsp2, SEQ ID NO:34; consensus, SEQ ID NO:35. In the consensus sequences of FIGS. 2A-D provided as SEQ ID NOS:18, 25, 30, and 35 in the sequence listing, "Xaa" can be any amino acid or can be missing at the positions shown. Preferably the amino acids at positions indicated in SEQ ID NOS:18, 25, 30, and 35 with "Xaa" are selected from the amino acids shown at those positions in FIGS. 2A-D.

FIG. 3. Capsid cleavage sites, either at the 3' end of capsid protein (Trp) or at the 5' end of the glycoprotein serine residue (Met-Ser). 3' end of Sindbis capsid (Scap), SEQ ID NO:11; 5' end of Sindbis glycoprotein (Sgly), SEQ ID NO:12; RCV (replication competent viral particles), SEQ ID NO:13.

FIG. 4. BLAST alignment of capsid protein sequences SEQ ID NO:1 (Sindbis), SEQ ID NO:2 (SFV), SEQ ID NO:3 (EEE), and SEQ ID NO:4 (VEE). Consensus sequence, SEQ ID NO:5.

Figure 5E:
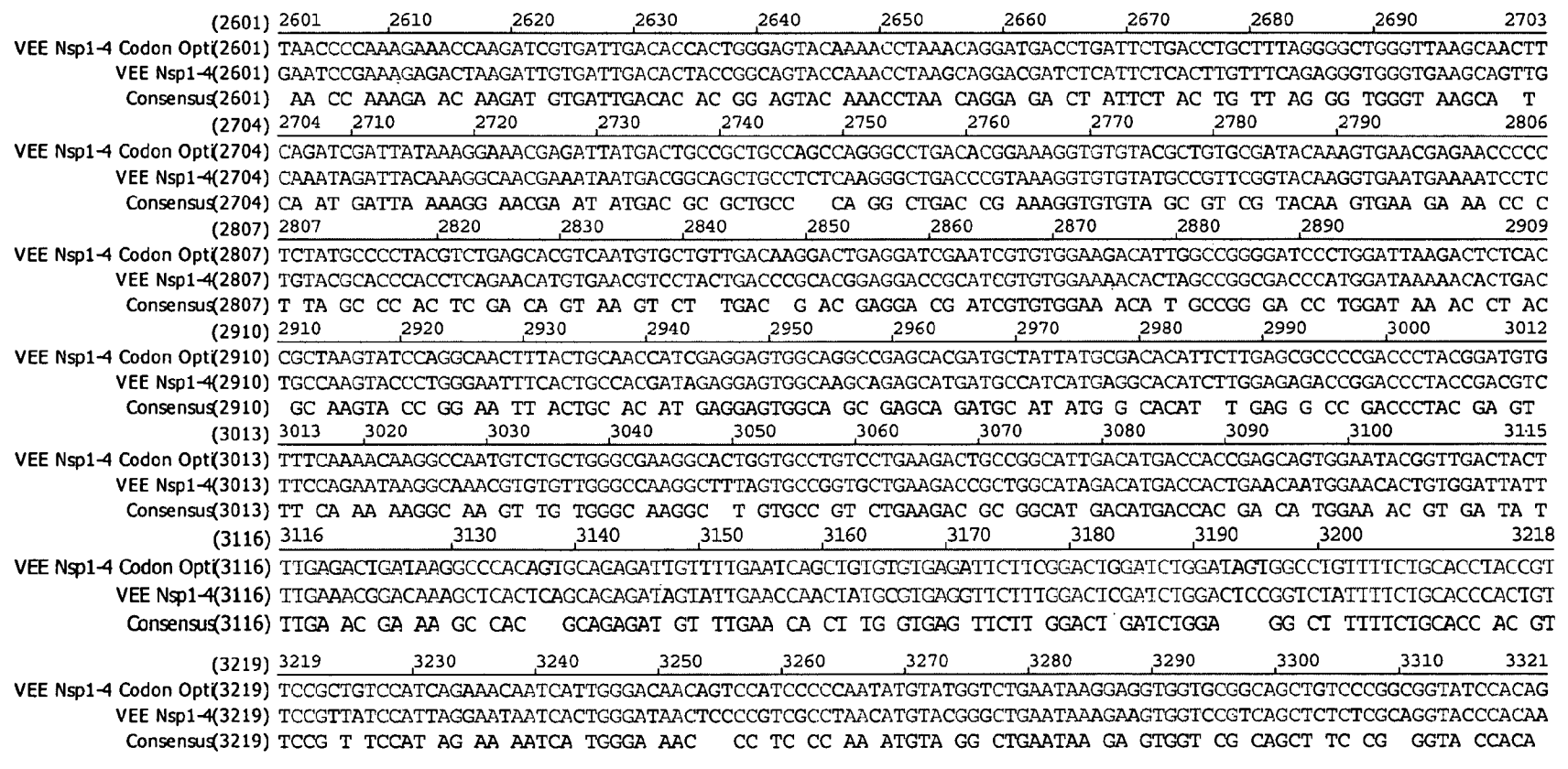
Figure 5F:
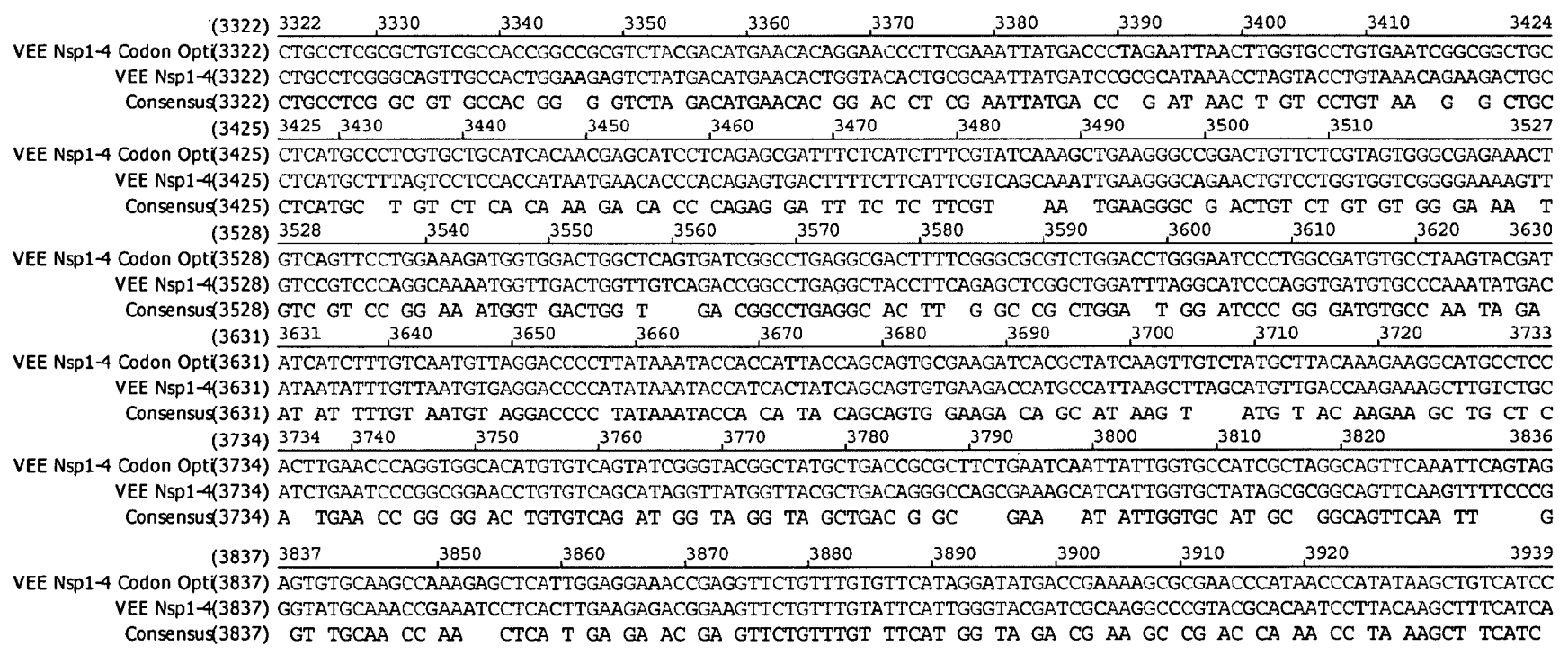
Figure 5G:
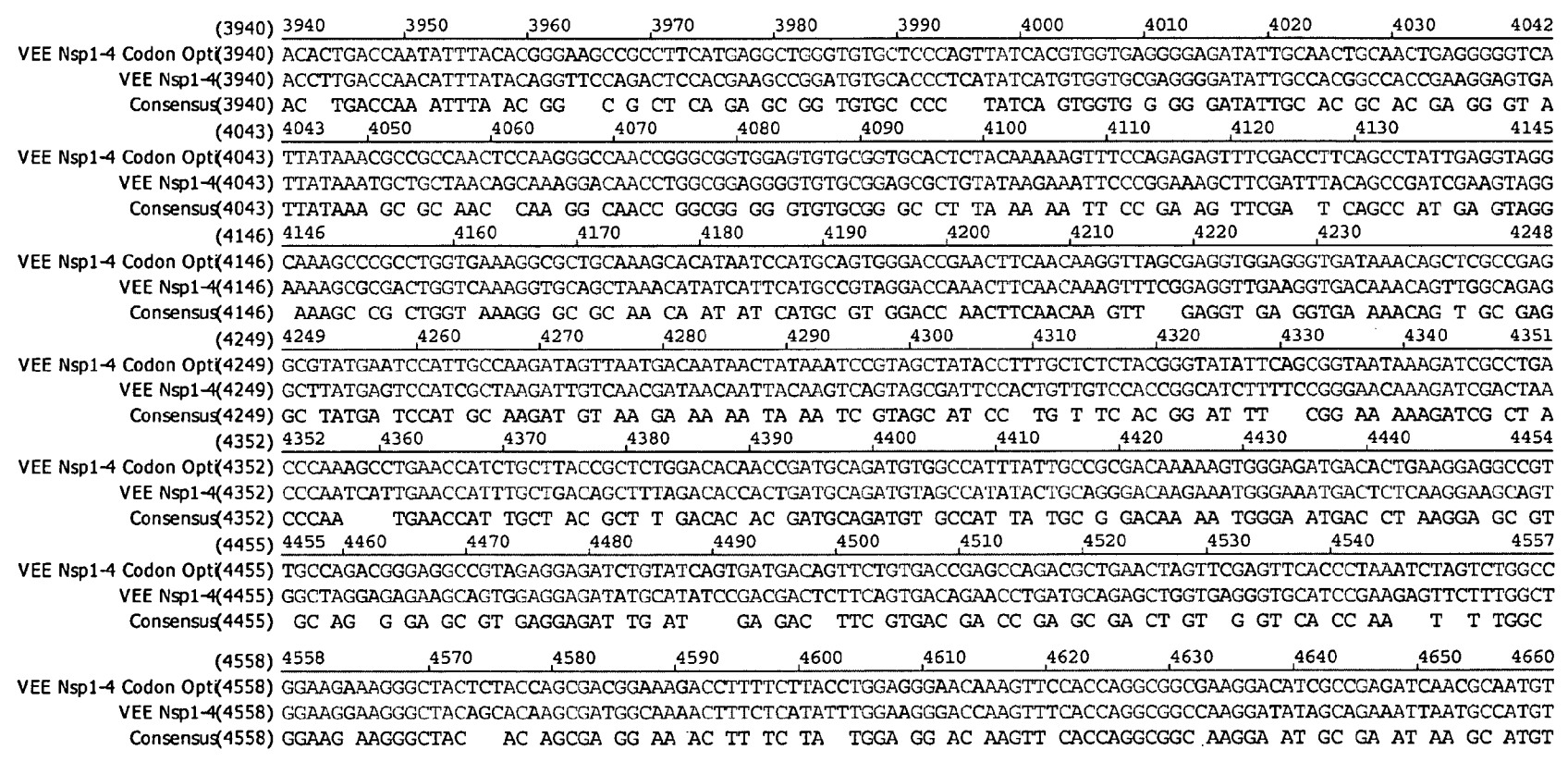
Figure 5H:
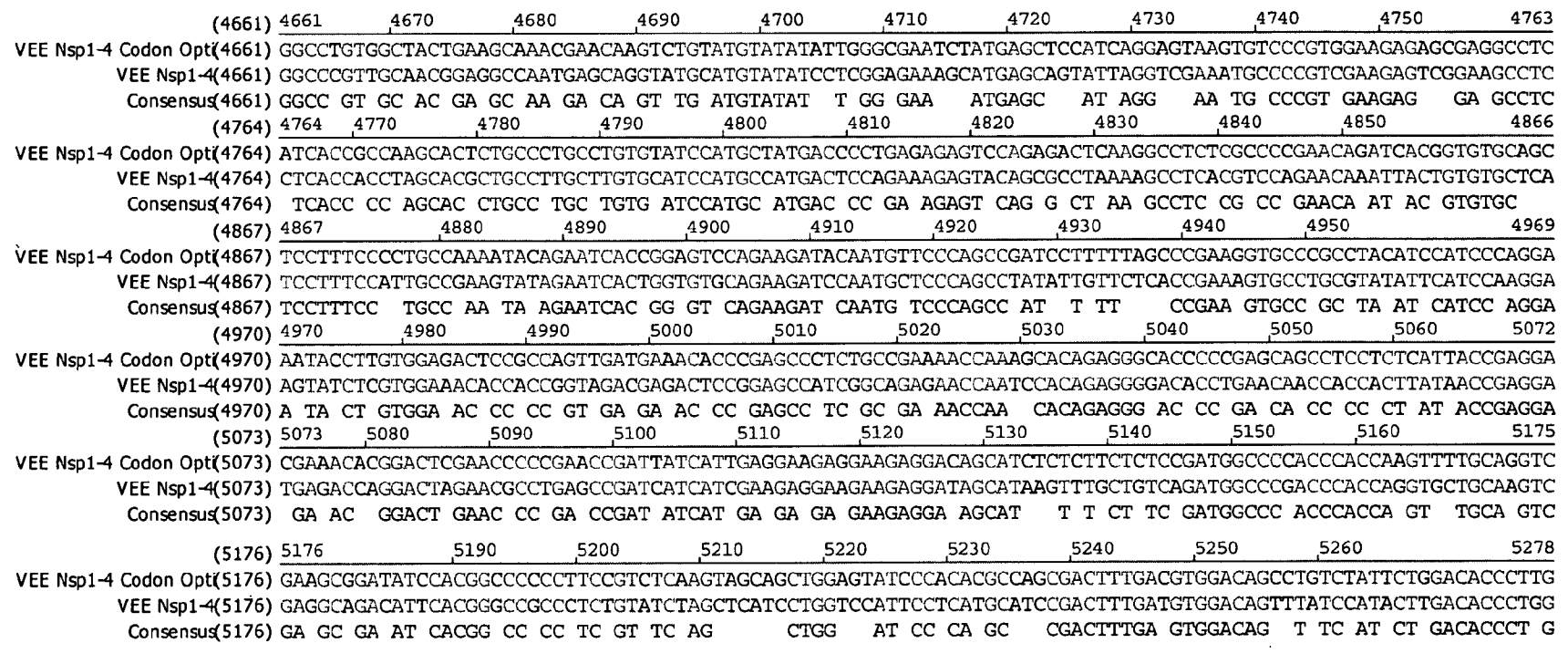
Figure 5I:
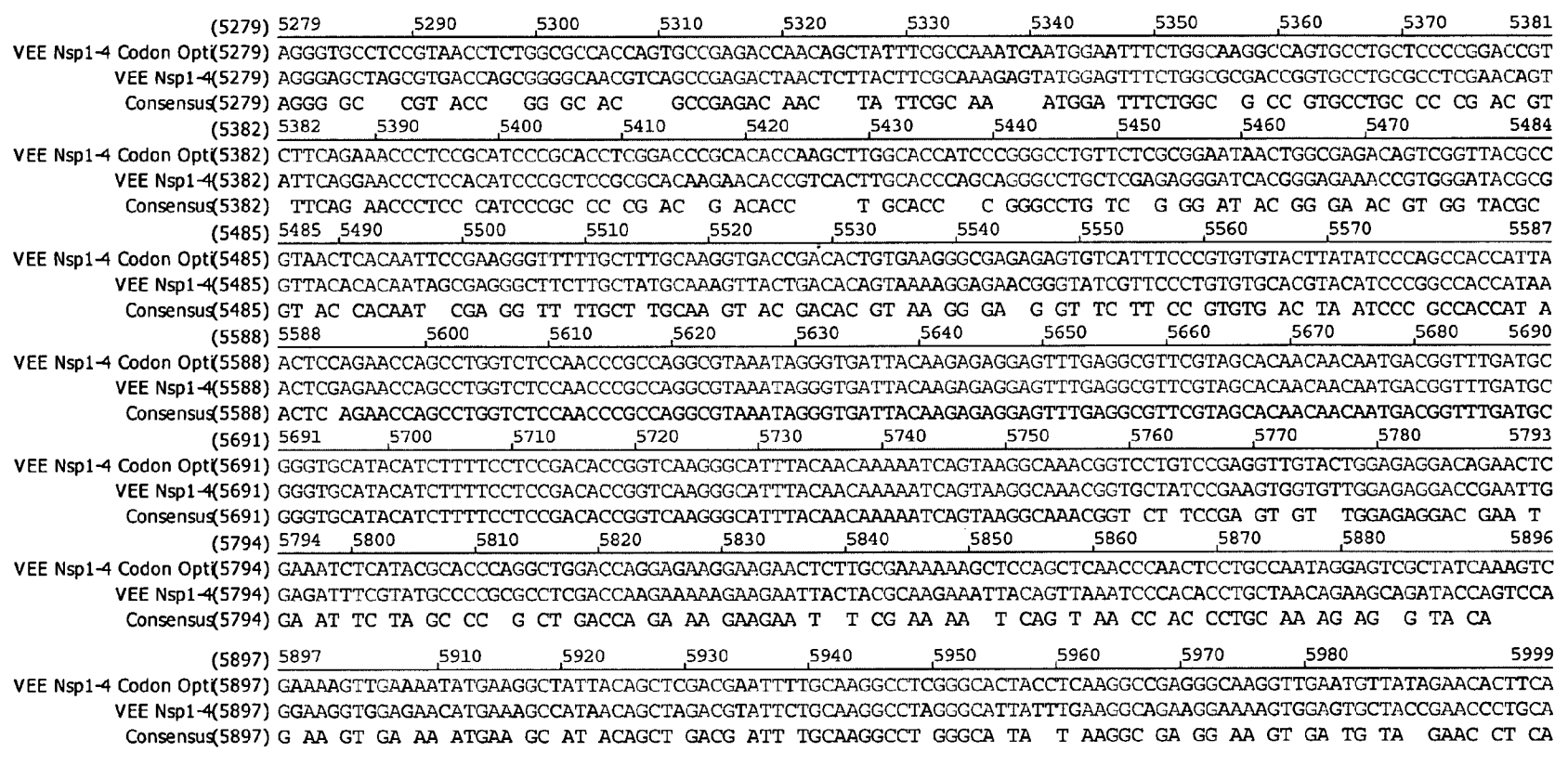
Figure 5J:
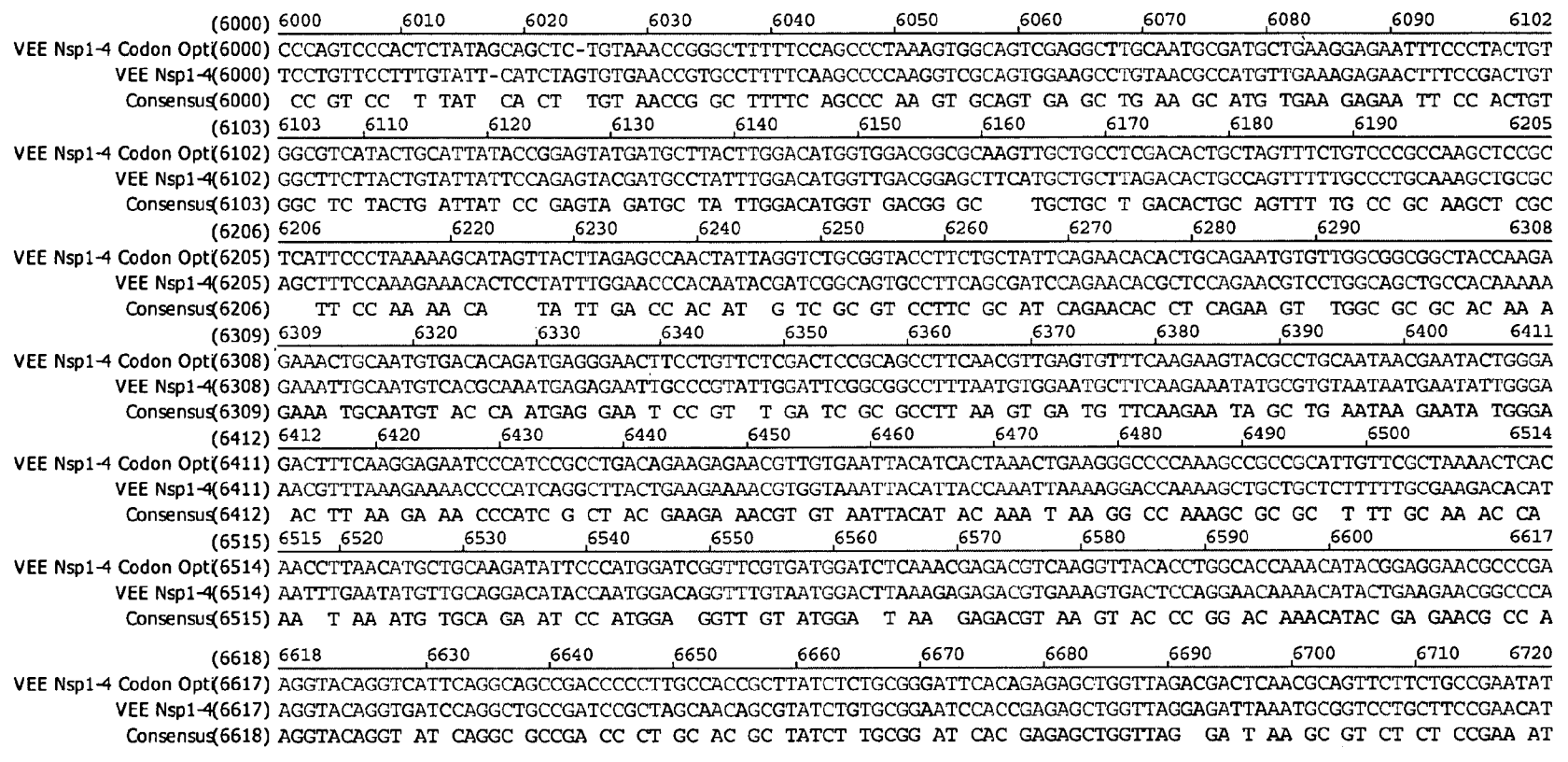
Figure 5K:
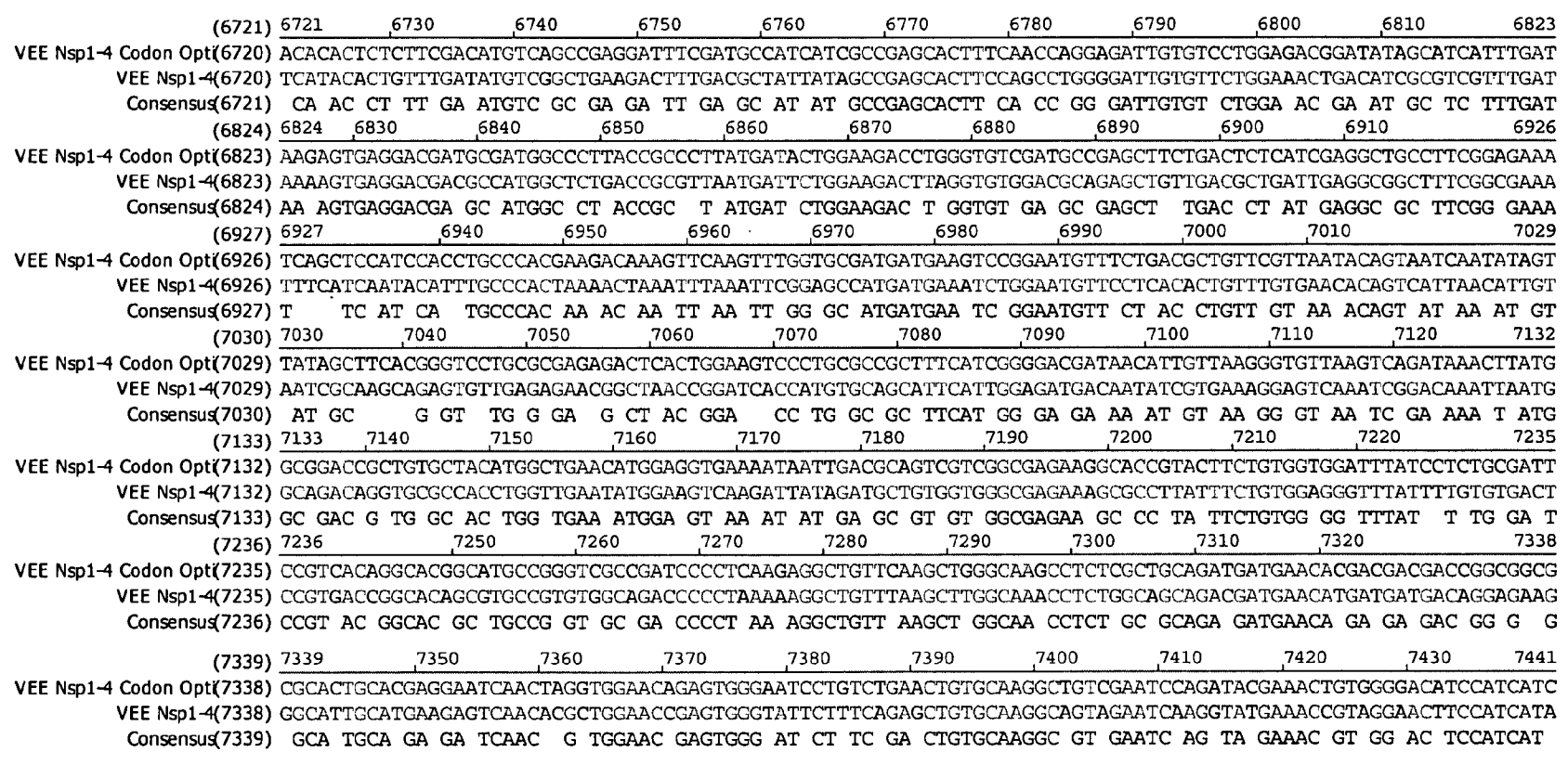

FIGS. 5A-L. BLAST alignment of VEE Nsp1-4 coding sequence with optimized coding sequence. VEE Nsp1-4 codon opt, SEQ ID NO:10; VEE Nsp1-4, SEQ ID NO:19; consensus, SEQ ID NO:20.

FIG. 6. Configuration of a double subgenomic promoter cassette. "CMV," cytomegalovirus promoter; "5'," 5' untranslated region and sequences from the N-terminus of the Nsp1 coding region that are necessary for replication; "JR," subgenomic promoter with the adjacent sequences (junction region); "Cap or Gly," capsid or glycoprotein; "Nsp1-3," non-structural proteins 1-3; "Nsp4," non-structural protein 4; "3'," 3' untranslated region; "ER," ribozyme cleavage site.

DETAILED DESCRIPTION OF THE INVENTION

Figure 1:
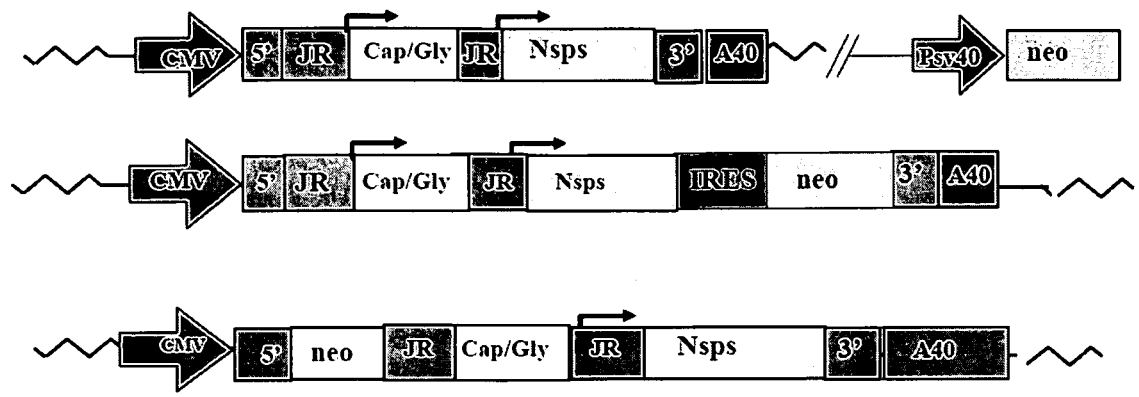
FIG. 1. Configurations of several double subgenomic promoter helper cassettes. "CMV," cytomegalovirus promoter; "5'," 5' untranslated region and sequences from the N-terminus of the Nsp1 coding region that are necessary for replication; "JR," subgenomic promoter with the adjacent sequences (junction region); "Cap/Gly," capsid or glycoprotein; "Nsps," non-structural proteins 1-4; "A40," 40-mer polyA tail; "3'," 3' untranslated region; "Psv40," SV40 promoter controlling transcription of neomycin resistance gene ("neo"); "IRES," internal ribosome entry site.
Figure 2:
FIGS. 2A-D. BLAST alignment showing cleavage sites in nonstructural proteins of various types of alphavirus.

In a split helper system, each structural protein is encoded in a separate defective helper (DH) cassette containing 5' and 3' cis elements necessary for replication (see, e.g., US 2006/0292175). Expression of the encoded structural protein depends on the successful replication of the DH cassette by a replicase complex translated from the replicon and the subsequent transcription of subgenomic RNA. The replicase complex is translated as a single polypeptide chain which then undergoes sequential self-cleavage events, with different cleavage complexes then performing distinctive replication functions. The functional replicase complexes, particularly minus strand replicases which are necessary for the very first step of DH replication, are available for a limited time and location.

The invention provides strategies which can be used to increase the amount and availability of effective replicase complexes, thereby increasing the replication efficiency of DH transcripts and the productivity of PCL. The invention also provides strategies for minimizing the generation of replication competent viral particles (RCV). Though described below in connection with alphavirus-based packaging cell-line systems, the concepts and methods of the invention can readily be applied to other protein expression systems or viral packaging cell line systems to obtain commercially viable yields.

Double Subgenomic Promoter Expression Cassettes

In some embodiments, coding sequences for alphavirus nonstructural proteins 1-4 (nsp1-4) are placed under the control of a second subgenomic promoter in the same expression cassette as a structural protein. Once induced by the replicon, these "double subgenomic promoter expression constructs" have the property of self-sustained replication but have virtually no expression without induction.

An expression cassette of the invention comprises two transcription units as well as a promoter and control elements needed for expression. Typical control elements include, but are not limited to, transcription promoters, transcription enhancer elements, chromatin insulator, transcription termination signals, polyadenylation sequences (located 3' to the translation stop codon), sequences for optimization of initiation of translation (located 5' to the coding sequence), translation termination sequences, 5' sequences required for non-structural protein-mediated amplification, and 3' sequences required for nonstructural protein-mediated amplification.

Promoters for use in expression cassettes of the invention can be inducible or constitutive. Useful promoters include promoters include the CMV, MMTV, MoMLV, adenovirus VA1RNA promoters, and PolI promoters.

In some embodiments the first transcription unit is 5' to the second transcription unit. In other embodiments the first transcription unit is 3' to the second transcription unit. In either case, the first transcription unit comprises an alphavirus subgenomic promoter operably linked to a first coding sequence which encodes an alphavirus structural protein. The second transcription unit comprises another alphavirus subgenomic promoter operably linked to a second coding sequence which encodes alphavirus non-structural proteins 1-4. Elements of a transcription unit are "operably linked" when they are configured so as to perform their usual function; i.e., expression of the structural protein and non-structural proteins is under the control of the subgenomic promoters.

Alphavirus subgenomic promoters (also referred to as "junction region promoters" or JR) are derived generally from the region between the nonstructural and structural protein open reading frames. Typically, an alphavirus subgenomic promoter contains a core sequence that provides most promoter-associated activity, as well as flanking regions that further enhance the promoter-associated activity. For example, the HR strain Sindbis virus subgenomic junction region promoter typically begins at approximately nucleotide number 7579 and continues through at least nucleotide number 7612 (and possibly beyond). At a minimum, nucleotides 7579 to 7602 are believed to serve as the core sequence necessary for transcription of the subgenomic fragment.

The two subgenomic promoters in an expression cassette of the invention preferably are the same but can be derived from different alphaviruses. For example, at least one of the first and second subgenomic promoters is a Venezuelan encephalitis virus (VEE) subgenomic promoter, a Sindbis virus subgenomic promoter, an Eastern equine encephalitis virus (EEE) subgenomic promoter, or a Semliki Forest virus subgenomic promoter. In preferred embodiments both subgenomic promoters are Sindbis, VEE, SFV, or EEE promoters.

An "alphavirus structural protein" refers to either a capsid protein or a glycoprotein (which includes E1 and E2 and, where appropriate, E3). The capsid and glycoproteins can but need not be derived from the same type of alphavirus, e.g., Sindbis virus, SFV, VEE, or EEE. Thus, in some expression cassettes at least one of the first and second alphaviruses is a Sindbis virus. In other expression cassettes, at least one of the first and second alphaviruses is a VEE virus.

Examples of capsid protein sequences are provided in SEQ ID NO:1 (Sindbis), SEQ ID NO:2 (SFV), SEQ ID NO:3 (EEE), and SEQ ID NO:4 (VEE). Examples of structural polyprotein sequences are provided in SEQ ID NO:36 (Sindbis; capsid, amino acids 1-264; E3, amino acids 265-328; E2, amino acids 329-751; 6K, amino acids 752-806; E1, amino acids 807-1245), SEQ ID NO:37 (SFV; capsid, amino acids 1-267; E3, amino acids 268-333; E2, amino acids 334-755; 6K, amino acids 756-815; E1, amino acids 816-1253), SEQ ID NO:38 (VEE; capsid, amino acids 1-275; E3, amino acids 276-334; E2, amino acids 335-756; 6K, amino acids 757-812; E1, amino acids 813-1254), and SEQ ID NO:39 (EEE; capsid, amino acids 1-260; E3, amino acids 261-323; E2, amino acids 324-743; 6K, amino acids 744-800; E1, amino acids 801-1241).

In some embodiments, described in more detail below, the capsid protein comprises a capsid protein which comprises one or more mutations which reduce autoproteolytic activity of the capsid protein (e.g., His141Ala, Asp147Ala, Asp163A, Ser215Ala, and combinations thereof, numbered according to SEQ ID NO:1).

In some embodiments, the capsid protein and/or the glycoprotein are "hybrid" proteins. A hybrid protein contains at least one functional domain derived from a first alphavirus while the remaining portion of the protein is derived from one or more additional alphaviruses. For example, a hybrid capsid protein can comprise an RNA binding domain from the first alphavirus and an envelope interaction domain from a second alphavirus. Hybrid capsid proteins and glycoproteins are described in more detail in US 2006/0292175.

As is known in the art, nonstructural proteins include nsP1, nsP2, nsP3, and nsP4. Examples of nonstructural protein sequences are provided as SEQ ID NOS:6-9, respectively. A DNA sequence encoding VEE Nsp1-4 using optimized codons is provided in SEQ ID NO:10. One of ordinary skill in the art will realize that a wide variety of sequences which encode alphavirus nonstructural proteins, in addition to those disclosed herein, may be used in the present invention, and are therefore deemed to fall within the scope of the phrase "alphavirus nonstructural proteins." For example, within one embodiment of the invention, due to the degeneracy of the genetic code, more than one codon may code for a given amino acid. Therefore, a wide variety of nucleic acid sequences which encode alphavirus nonstructural proteins may be generated. Within other embodiments of the invention, a variety of other nonstructural protein derivatives may be made, including for example, various substitutions, insertions, or deletions, the net result of which do not alter the biological activity of the alphavirus nonstructural proteins. Within the context of the present invention, alphavirus non-structural proteins are deemed to be biologically active in toto if they promote the self-replication or trans-replication of the vector construct. Self-replication or trans-replication, which refers to replication of viral vector nucleic acids may be readily determined by metabolic labeling or RNase protection assays performed over a course of time.

Similarly, the capsid and glycoprotein proteins discussed above are not limited to polypeptides having the exact sequences disclosed herein. Alphaviral genomes are often in flux and contain several variable domains that exhibit relatively high degrees of variability between species and isolated. The terms "capsid," "glycoprotein," and "nonstructural protein(s)" encompass such proteins from any of the identified alphaviruses, as well as newly identified isolates, and subtypes of these isolates. In addition, amino acid sequences can be modified, particularly those in regions exhibiting high sequence homology.

Various nucleotide sequences can be used to encode the structural and nonstructural proteins. Optionally, as described below, sequences encoding nsp1-4 can be optimized to reduce the possibility of co-packaging into recombinant particles and to prevent recombination that could generate replication competent virus (RCVs).

In some embodiments expression cassettes of the invention comprise a selectable marker, such as Neo, SV2 Neo, hygromycin, puromycin, phleomycin, histidinol, or DHFR, which can be located at various points in the expression cassette as long as function of the transcription units is not disrupted.

Some expression cassettes of the invention comprise an internal ribosome entry site (IRES). The IRES can be placed between the 5' cis-replication element and subgenomic promoter, between two subgenomic promoters, or between subgenomic coding region and the 3' cis-replication element.

In another embodiment of the invention, all four non-structural proteins are produced from a single expression cassette, which has the advantage of more efficient assembly of replication complexes and increased expression of capsid and glycoproteins. See Vokova et al., *Virology* 344, 315-27, 2006; and U.S. Pat. No. 7,332,322. In some embodiments of the invention, transcription of nsp1-3 is under the control of an inducible or constitutive promoter as described above, transcription of the capsid or the glycoprotein is under the control of a first subgenomic promoter, and transcription of nsp4 is under the control of a second subgenomic promoter. Optionally, Nsp1-4 sequences are codon-optimized (see, e.g., SEQ ID NO:10). In some embodiments the capsid cassette has a puromycine marker and the glycoprotein cassette has no marker.

Examples of expression cassettes according to the invention are shown in FIG. 1 and FIG. 6.

Host Cells and Packaging Cell Lines

Expression cassettes of the invention can be introduced into host cells. In some cases, the host cell comprises a first expression cassette, which comprises (a) a first transcription unit comprising a first alphavirus subgenomic promoter operably linked to a first coding sequence which encodes a structural protein of a first alphavirus; and (b) a second transcription unit comprising a second alphavirus subgenomic promoter operably linked to a second coding sequence which encodes non-structural proteins 1-4 of a second alphavirus. Some host cells contain two such expression cassettes; in these embodiments the first expression cassette encodes a capsid protein and the second expression cassette encodes the glycoprotein. Such host cells can be used as packaging cells, which can be used to make recombinant alphavirus particles.

Host cells can be any eukaryotic cell which is suitable for recombinant protein production. These include avian cells, insect cells (e.g., C6/36, SF9), vertebrate, and mammalian cells. Examples of useful mammalian cell lines include Vero, MDBK, MDCK, MRC, NIH-3T3, BHK, PERC.6® (available from Crucell; see WO 01/38362 and WO 02/40665), EB cell lines, and HEK293 cells. Sources of avian cells include, but are not limited to, embryonic stem cells such as EBX® cells (Vivalis, FR), embryonic fibroblasts, and embryonic germ cells. Useful avian cells include the duck cell line AGE1.CR (ProBioGen). Other avian cell lines are disclosed, e.g., in U.S. Pat. No. 5,340,740; U.S. Pat. No. 5,656,479; U.S. Pat. No. 5,830,510; U.S. Pat. No. 6,114,168; U.S. Pat. No. 6,500,668; U.S. Pat. No. 6,872,561; EP 0787180B; EP03291813.8; WO 03/043415; and WO 03/076601.

Expression cassettes of the invention can be introduced into host cells using methods well known in the art, including, but not limited to, microinjection, liposome-mediated transfection, electroporation, and calcium phosphate precipitation. Alternatively, expression constructs of the invention can be incorporated into a polynucleotide delivery vehicle, such as a plasmid or a viral-based vector.

Once recombinant host cells, or "packaging cells," have been constructed they can be used to produce recombinant alphavirus particles upon introduction of a replicon comprising an alphavirus packaging signal and encoding a protein of interest. The protein of interest is typically an antigen. Antigens can be derived from any of several known viruses, bacteria, parasites and fungi, as well as any of the various tumor antigens or any other antigen to which an immune response is desired. Furthermore, for purposes of the present invention, an "antigen" refers to a protein that includes modifications, such as deletions, additions and substitutions (generally conservative in nature), to the native sequence, so long as the protein maintains the ability to elicit an immunological response. These modifications may be deliberate, as through site-directed mutagenesis, or may be accidental, such as through mutations of hosts that produce the antigens. See US 2006/0292175.

Non-limiting examples of bacterial pathogens from which antigens can be derived include diphtheria, staphylococcus, cholera, tuberculosis, tetanus, *S. pneumoniae, S. agalactiae, S. pyogenes*, pertussis, meningitis, *N. gonorrheae, H. pyloris, H. influenza*, and *P. gingivalis*.

Non-limiting examples of viral pathogens include meningitis virus, influenza virus, rhinovirus, respiratory syncytial virus, parainfluenza virus, Picornaviruses, human Papilloma virus, retroviruses, and hepatitis viruses.

Tumor antigens include, but are not limited to, MART-1, gp100, tyrosinase, tyrosinase related proteins 1 and 2, β-catenin, MUM-1, CDK-4, caspase-8, KIA 0205, HLA-A2-R1701; MAGE-1, MAGE-2, MAGE-3, MAGE-12, BAGE, GAGE, NY-ESO-1, alpha-fetoprotein, telomerase catalytic protein, G-250, MUC-1, carcinoembryonic antigen, p53, Her-2-neu, triosephosphate isomerase, CDC-27, and LDLR-FUT). See also WO 91/02062, U.S. Pat. No. 6,015,567, WO 01/08636, WO 96/30514, U.S. Pat. No. 5,846,538 and U.S. Pat. No. 5,869,445.

Sequential Amplification of DH Cassettes Involving Mutant Replicase Complexes

Other embodiments involve sequential amplification of DH cassettes. These embodiments take advantage of cell lines which constitutively express VEE nonstructural proteins and various alphavirus nonstructural protein mutants that have specific defects in subgenomic transcription but not in DH/replicon replication. Thus, these mutant nonstructural protein replicase complexes can be constitutively expressed to amplify the DH, but will not produce subgenomic transcripts coding alphavirus structural protein. Upon induction of the replicon, the amplified DH RNA is further amplified by wild type nsps from replicon. The wild type replicase complexes also produce subgenomic transcripts and lead to the expression of structural proteins. Several of theses mutants show over hundreds-fold decrease in subgenomic RNA transcription or particle production compared with wild type nonstructural proteins, providing a powerful inducible system.

One useful mutant is the nsP2 cleavage mutant. Alphavirus minus strand replication requires uncleaved P123 together with correctly cleaved nsP4 and is shut off approximately 4 hours after infection (Kaariainen and Ahola, *Prog. Nucleic Acid Res. Mol. Biol.* 71, 187-222, 2002). Thus, mutations at well-conserved alphavirus nsps cleavage sites will not be cleaved and the mutant replicase should be available for a longer time compared with wild type replicase. In addition, in Sindbis and SFV such mutants have very low level of subgenomic RNA transcription (Lemm et al., *EMBO J.* 13(12), 2925-34, 1994, Shirako & Strauss, *J Virol.* 68(3), 1874-85, 1994, Kim et al., *Virology* 323(1), 153-63, 2004). These cleavage sites are well conserved in VEE virus (FIG. 2), and several different mutants (such as mutations at nsP1/nsP2 and nsP2/nsP3 cleavage sites) can be made.

The other mutations include R331A and R332A mutations in the Sindbis Nsp4 protein (Li & Stollar, *Proc. Natl. Acad. Sci. USA* 101, 9429-34, 2004), which abolish the subgenomic promoter binding/transcription ability of replicase complexes but retain the ability to amplify viral/DH genome. These mutations are highly conserved among different alphavirus families. Alternatively, deletions or other substitutions at R331, R332 (numbered according to SEQ ID NO:9) or both can be used. These mutant Nsp1-4 replicase complexes can be expressed from same DH transcript (such as linked to an IRES sequence) or can be expressed in cell substrate from a separate transcript cassette. Suitable substitutions include:

at R331: glutamine, leucine, serine, asparagine, glutamic acid, lysine, threonine, glycine, methionine, tryptophan, aspartic acid, histidine, phenylalanine, tyrosine, cysteine, isoleucine, proline, alanine, or valine; or at R332: glutamine, leucine, serine, glutamic acid, lysine, threonine, glycine, methionine, tryptophan, aspartic acid, histidine, phenylalanine, tyrosine, cysteine, isoleucine, proline, alanine, or valine.

Several Sindbis and SFV temperature sensitive mutants show specific defects in subgenomic RNA synthesis (Lulla, *Virology* 80(6), 3108-11, 2006; Lastarza, *J. Virol.* 68(9), 5781-91, 1994). Such mutants also are useful for making Sindbis-, VEE-, and SFV-based PCL.

Optionally, alphavirus mutant nsp1-4 codons can be optimized to reduce the possibility of co-packaging into recombinant particles and to prevent recombination that could generate replication competent virus (RCVs). A DNA sequence encoding VEE Nsp1-4 using optimized codons is shown in SEQ ID NO:13.

Each of the strategies described above can be used in conjunction with one or more of the strategies described below.

Minimizing the Risk of Generating RCV Using Capsid Autoproteolysis Mutants

Generation of RCV (replication competent viral particles) is a potential problem for the application of alphavirus based replicon particles. The probability of recombination is greatly reduced by dividing the defective helpers into two separate cassettes because multiple switches would be required to produce an infectious RNA. However, it is conceivable that during large-scale production, RCV could be generated. The invention provides capsid autoproteolytic mutants which can be used to further reduce the possibility of generating RCV, providing an additional safeguard for the production of alphavirus based replicon particles. Using this strategy it is virtually impossible to generate wild type RCV.

Alphavirus structural proteins are translated in vivo from a 26S subgenomic RNA as a polyprotein that is processed both cotranslationally and posttranslationally. The capsid is postulated to be a serine protease that release itself from the N terminus of the nascent polyprotein by autoproteolysis. Several Sindbis virus autoproteolysis mutants have been identified (e.g., His141, Asp147, and Ser215) and all were lethal to the virus (Hahn & Strauss, 1990, *J. Virol.* 64, 3069-73, 1990). In a double helper system, the capsid is artificially separated from structural polyprotein, and the autoproteolysis function is probably not critical for alphavirus particle production. Thus, capsid autoprotease mutations can be used to minimize the risk of generating RCV. These mutations include changes at His141 (e.g., His141Ala), Asp147 (e.g., Asp147Ala), Asp163 (e.g., Asp163Ala), Ser215 (e.g., Ser215Ala), numbered according to SEQ ID NO:1, and combinations thereof. Other substitutions include:

at His141: glutamine, leucine, serine, arginine, glutamic acid, lysine, threonine, glycine, methionine, tryptophan, aspartic acid, histidine, phenylalanine, tyrosine, cysteine, isoleucine, proline, or valine;

at Asp147: glutamine, leucine, serine, arginine, glutamic acid, lysine, threonine, glycine, methionine, tryptophan, aspartic acid, histidine, phenylalanine, tyrosine, cysteine, isoleucine, proline, or valine;

at Asp163: glutamine, leucine, serine, arginine, glutamic acid, lysine, threonine, glycine, methionine, tryptophan, aspartic acid, histidine, phenylalanine, tyrosine, cysteine, isoleucine, proline, or valine; or at Ser215: glutamine, leucine, serine, arginine, glutamic acid, lysine, threonine, glycine, methionine, tryptophan, aspartic acid, histidine, phenylalanine, tyrosine, cysteine, isoleucine, proline, or valine.

Changes also include deletions (e.g., ΔHis141, ΔAsp147, ΔAsp163, ΔSer215, and ΔTrp264 and insertions. Capsid proteins for use in the invention can comprise one, two, three or more such mutations.

In some embodiments, mutations are introduced at the capsid cleavage sites, either at the 3' end of capsid protein (Trp) or at the 5' end of the glycoprotein serine residue (Met-Ser) or in combinations (see FIG. 3). Deletions of key residues (e.g., capsid W264 and Gly Ser2) also can be made. Because capsid autocatalytic sites are conserved among different strains, this strategy can be used for a variety of alphavirus-based systems (e.g., Sindbis, SFV, and VEE; see FIG. 4).

All patents, patent applications, and references cited in this disclosure are expressly incorporated herein by reference. The above disclosure generally describes the present invention. A more complete understanding can be obtained by reference to the following specific examples, which are provided for purposes of illustration only and are not intended to limit the scope of the invention.

Example 1

Improved Expression of Heterologous Protein Under the Control of a DH Cassette Comprising Two Subgenomic Promoters DH expression cassettes which encode alphavirus nsP1-4 under a subgenomic promoter have the property of self-sustained replication once induced by replicon. Preliminary results using green fluorescent protein (GFP) as reporter system showed that such constructs have provide a 3-4 fold increase in the percentage of GFP positive cells and a similar fold of increase in mean fluorescence intensity (see Table 1).

TABLE 1

| vector | mean GFP value | % cells positive |
|---|---|---|
| single subgenomic promoter | 85 | 0.8 |
| double subgenomic promoter (nsp1-neo fusion protein) | 307 | 2.68 |
| double subgenomic promoter (IRESneo) | 206 | 2.12 |

Example 2

Capsid Mutants

Site-directed mutagenesis was used to generate the following capsid mutants: His141Ala, Asp147Ala, Ser215Ala, Trp264Ala and various of compound mutants. Mutagenesis was confirmed by sequencing. Mutations were incorporated into two split cassette RNAs (VCR-DH-Scap, VCR-DH-Sgly) to test whether they interfere with recombinant alphavirus particle production. In vitro Sp6-transcribed RNAs (wild-type or mutant capsid RNA, glycoprotein RNA, and green fluorescent protein (GFP) replicon RNA) were electroporated into BHK-v cells. Twenty hours later the supernatants were harvested and used to infect naïve BHK cells. Eighteen hours later, FACS analysis was performed to determine the titer of replicon GFP particles. The results are shown in Tables 2 and 3.

TABLE 2

| capsid | Replicon particle titer (IU/ml) |
| --- | --- |
| wild-type capsid | 1.43E8 |
| capsid H141A mutant | 1.63E8 |
| capsid D147A mutant | 9.65E7 |
| capsid S215A mutant | 1.14E8 |
| capsid W264A mutant | 2.48E6 |

TABLE 3

| capsid | Replicon particle titer (IU/ml) |
| --- | --- |
| wild-type capsid | 3.17E8 |
| capsid H141A + D163A | 3.08E8 |
| capsid H141 + S215A | 3.84E8 |
| capsid D163 + S215A | 3.76E8 |
| capsid H141A + D163A + S215A | 4.89E8 |

The results show that the H141A, D147A, and S215A mutations do not affect the replicon particle titer, and the various compound mutants have a comparable level of particle production compared with wild type.

Example 3

Comparison of Single and Double Subgenomic Promoter Expression Constructs

Using green fluorescent protein (GFP) as the protein of interest, this example demonstrates that double subgenomic promoter expression constructs of the invention produce more protein of interest than constructs that employ only one subgenomic promoter.

BHK-v cells were propagated on 6-well plates and maintained in Dulbecco's modified Eagle medium (DMEM) (Cellgro, Vermont, Va.) supplemented with 10% gamma-irradiated fetal bovine serum, 1% antibiotic (penicillin and streptomycin), and 1% sodium pyruvate (Cellgro). VEE defective helper plasmid DNAs (VCP-nf3.1-GFP which codes for single subgenomic GFP transcript, and VCP-Psub-GFP-PsubNsp1-4 which codes for double subgenomic transcripts GFP and Nsp1-4) were transfected into BHK-v cells using LT1 transfection agent (Minis Bio) at 2 μg per well. Cells were expanded 48 hours post-transfection, and Geneticin (G418 sulfate, a neomycin sulfate analog; Cellgro) was added at 600 μg/ml in growth medium for selection and maintenance of stable recombinant BHK-v cell lines. Pools were collected from both transfections and propagated on 6-well plates. VCR-Chim2.1-gp120 replicon particles were used to infect the pool at MOI 5, and cells were collected 24 hours after infection. FACS analysis was performed to determine the GFP positive ratio. The results of duplicate (or quadruplicate) experiments for each construct are shown in Table 3.

The construct "VCP-nf3.1-GFP" listed in Table 3 contains only one subgenomic promoter. The construct "VCP-Pgfp-Pnsp-IRESneo" is the middle construct in FIG. 1. "VCP" stands for VEE CMV promoter plasmid; "Pgfp" stands for subgenomic promoter with GFP coding region; "Pnsp" stands for subgenomic promoter with Nsp1-4 coding region; and "IRES" stands for EMCV IRES driven neomycin.

TABLE 3

| Construct | Mean (not-induced)/SD/% (+) | Mean (induced)/SD/% |
| --- | --- | --- |
| VCP-nf3.1-GFP | 26.45/6.68/0.17 | 50.36/83.38/0.61 |
| | 28.34/8.64/0.17 | 149.60/476.88/0.61 |
| | 1.15/0.31/0 | 77.07/148.31/1.52 |
| | 1.32/0.58/0 | 64.56/87.55/0.60 |
| VCP-Pgfp-Pnsp-IRESneo | 235.52/977.35/0.71 | 249.03/450.47/1.92 |
| | 115.11/163.18/1.0 | 240.43/449.26/2.91 |
| | 105.35/158.29/0.78 | 281.36/540.27/2.65 |
| | 151.60/368.25/0.80 | 324.42/541.99/1.86 |
| | 266/397/0.23 | 394/1116/2.55 |
| | 253/208/1.03 | 319/447/4.65 |
| | 436/810/0.27 | 198/380/1.34 |
| | 471/513/1.13 | 451/541/3.59 |
| VCP-nf3.1Pgfp-Pnsp | 130/281/0.21 | 115/422/1.29 |
| | 448/837/0.5 | 299/989/3.65 |
| | 54/47/0.17 | 144/711/1.11 |
| | 247/492/0.41 | 269/789/2.45 |

The invention claimed is:
1. An RNA expression cassette comprising a first and second transcription unit, wherein:
   (a) the first transcription unit comprises a first alphavirus subgenomic promoter operably linked to a first coding sequence which encodes a mutant capsid protein of a first alphavirus, but not a glycoprotein of the first alphavirus, wherein the mutant capsid protein has reduced autoproteolytic activity;
   (b) the second transcription unit comprises a second alphavirus subgenomic promoter operably linked to a second coding sequence which encodes non-structural proteins 1-4 of a second alphavirus,
wherein the expression cassette enhances production of replicon particles while minimizing generation of replication competent viral particles (RCVs) when used in a suitable packaging cell line.

2. The expression cassette of claim 1 wherein the first transcription unit is 5' to the second transcription unit.

3. The expression cassette of claim 1 wherein the first transcription unit is 3' to the second transcription unit.

4. The expression cassette of claim 1 wherein said first coding sequence encodes a hybrid capsid protein.

5. The expression cassette of claim 1 wherein the mutation is selected from the group consisting of His141Ala, Asp147Ala, Asp163Ala, Ser215Ala, ΔHis141, ΔAsp147, ΔAsp163, ΔSer215, and ΔTrp264 and combinations thereof, numbered according to SEQ ID NO:1.

6. The expression cassette of claim 1 wherein at least one of the first and second alphaviruses is a Sindbis virus.

7. The expression cassette of claim 1 wherein at least one of the first and second alphaviruses is a Venezuelan equine encephalitis (VEE) virus.

8. The expression cassette of claim 1 wherein at least one of the first and second subgenomic promoters is a VEE subgenomic promoter, a Sindbis virus subgenomic promoter, an Eastern equine encephalitic (EEE) subgenomic promoter, or a Semliki Forest virus subgenomic promoter.

9. The expression cassette of claim 1 further comprising a selectable marker.

10. The expression cassette of claim 1 further comprising an internal ribosome entry site (IRES).

11. The expression cassette of claim 1 wherein the first coding sequence comprises a sequence encoding SEQ ID NO:2.

12. The expression cassette of claim 1 wherein the second transcription unit comprises a mutation in at least one of R331 or R332 in Nsp4 numbered according to SEQ ID NO:9.

13. An isolated host cell comprising a first RNA expression cassette, wherein the first expression cassette comprises:
   (a) a first transcription unit comprising a first alphavirus subgenomic promoter operably linked to a first coding sequence which encodes glycoprotein or a capsid protein, but not both, of a first alphavirus; and
   (b) a second transcription unit comprising a second alphavirus subgenomic promoter operably linked to a second coding sequence which encodes non-structural proteins 1-4 of a second alphavirus,
wherein the host cell is adapted for large-scale production of replicon particles and has enhanced production of replicon particles while minimizing generation of replication competent viral particles (RCVS).

* * * * *